(12) United States Patent
Manning et al.

(10) Patent No.: US 10,239,945 B2
(45) Date of Patent: Mar. 26, 2019

(54) THERAPEUTIC CD47 ANTIBODIES

(71) Applicant: Arch Oncology, Inc., St. Louis, MO (US)

(72) Inventors: Pamela T. Manning, Chesterfield, MO (US); Robyn Puro, St. Louis, MO (US); Juan C. Almagro, Cambridge, MA (US); Robert W. Karr, St. Louis, MO (US)

(73) Assignee: Arch Oncology, Inc., St. Louis, MO (US)

( * ) Notice: Subject to any disclaimer, the term of this patent is extended or adjusted under 35 U.S.C. 154(b) by 0 days.

(21) Appl. No.: 15/820,054

(22) Filed: Nov. 21, 2017

(65) Prior Publication Data

US 2018/0171014 A1  Jun. 21, 2018

Related U.S. Application Data

(63) Continuation of application No. PCT/US2016/052383, filed on Sep. 17, 2016.

(60) Provisional application No. 62/354,592, filed on Jun. 24, 2016, provisional application No. 62/263,544, filed on Dec. 4, 2015, provisional application No. 62/252,171, filed on Nov. 6, 2015, provisional application No. 62/232,681, filed on Sep. 25, 2015, provisional application No. 62/221,852, filed on Sep. 22, 2015, provisional application No. 62/220,725, filed on Sep. 18, 2015, provisional application No. 62/220,691, filed on Sep. 18, 2015.

(51) Int. Cl.
*A61K 39/00* (2006.01)
*C07K 16/28* (2006.01)

(52) U.S. Cl.
CPC ...... *C07K 16/2839* (2013.01); *C07K 16/2803* (2013.01); *A61K 2039/505* (2013.01); *C07K 2317/24* (2013.01); *C07K 2317/33* (2013.01); *C07K 2317/41* (2013.01); *C07K 2317/52* (2013.01); *C07K 2317/56* (2013.01); *C07K 2317/71* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,261,839 B1 | 7/2001 | Multhoff | |
| 7,514,229 B2 | 4/2009 | Jamieson | |
| 7,531,643 B2 | 5/2009 | Fukushima | |
| 7,696,325 B2 | 4/2010 | Fukushima | |
| 8,101,719 B2 | 1/2012 | Kikuchi | |
| 8,236,313 B2 | 8/2012 | Isenberg | |
| 8,562,997 B2 | 10/2013 | Jaiswal | |
| 8,728,476 B2 | 5/2014 | Van | |
| 8,758,750 B2 | 6/2014 | Weissman | |
| 8,759,495 B2 | 6/2014 | Boghaert | |
| 8,951,527 B2 | 2/2015 | Isenberg | |
| 9,017,675 B2 | 4/2015 | Liu | |
| 9,045,541 B2 | 6/2015 | Eckelman | |
| 9,221,908 B2 | 12/2015 | Frazier | |
| 9,382,320 B2 | 7/2016 | Liu | |
| 9,518,116 B2 | 12/2016 | Frazier | |
| 9,518,117 B2 | 12/2016 | Frazier | |
| 2001/0041670 A1 | 11/2001 | Simantov | |
| 2003/0108546 A1 | 6/2003 | Fukushima | |
| 2004/0213792 A1 | 10/2004 | Clemmons | |
| 2006/0088522 A1 | 4/2006 | Boghaert | |
| 2007/0111238 A1 | 5/2007 | Jamieson | |
| 2010/0173382 A1 | 7/2010 | Boghaert | |
| 2010/0203559 A1 | 8/2010 | Ester | |
| 2013/0142786 A1 | 6/2013 | Liu | |
| 2013/0224188 A1 | 8/2013 | Eckelman | |
| 2014/0065169 A1 | 3/2014 | Jaiswal | |
| 2014/0140989 A1 | 5/2014 | Eckelman | |
| 2014/0161799 A1 | 6/2014 | Frazier | |
| 2014/0161825 A1 | 6/2014 | Jaiswal | |
| 2014/0199308 A1 | 7/2014 | Van | |
| 2014/0363442 A1 | 12/2014 | Frazier | |
| 2014/0369924 A1 | 12/2014 | Weissman | |
| 2015/0030600 A1 | 1/2015 | Marks | |
| 2015/0274826 A1 | 10/2015 | Frazier | |

(Continued)

FOREIGN PATENT DOCUMENTS

AU  2014201010  3/2014
BY  6782 C1  3/2005

(Continued)

OTHER PUBLICATIONS

Mariuzza et al (Annu. Rev. Biophys. Biophys. Chem. 1987; 16: 139-159).*
Winkler et al (J. Imm., 265:4505-4514, 2000).*
Giusti et al (PNAS, 9: 2926-2930, 1987).*
Rudikoff et al (PNAS, 79:1979-1983, 1982).*
International Application No. PCT/US2013/074766; International Preliminary Report on Patentability, dated Jun. 16, 2015; 8 pages.
International Application No. PCT/US2015/035345; International Preliminary Report on Patentability, dated Dec. 15, 2016; 4 pages.
International Application No. PCT/US2015/035345; International Search Report and Written Opinion of the International Search Authority; dated Oct. 15, 2015; 6 pages.

(Continued)

*Primary Examiner* — Brad Duffy
(74) *Attorney, Agent, or Firm* — Dennis A. Bennett; Charles H. Rexer, Jr.

(57) ABSTRACT

Provided are anti-CD47 monoclonal antibodies (anti-CD47 mAbs) with distinct functional profiles as described herein, methods to generate anti-CD47 mAbs, and to methods of using these anti-CD47 mAbs as therapeutics for the prevention and treatment of solid and hematological cancers, ischemia-reperfusion injury, cardiovascular diseases, autoimmune diseases, inflammatory diseases or as diagnostics for determining the level of CD47 in tissue samples.

14 Claims, 20 Drawing Sheets
Specification includes a Sequence Listing.

(56) References Cited

U.S. PATENT DOCUMENTS

| | | |
|---|---|---|
| 2016/0130336 A1 | 5/2016 | Lai |
| 2016/0137733 A1 | 5/2016 | Frazier |
| 2016/0137734 A1 | 5/2016 | Frazier |
| 2016/0289326 A1 | 10/2016 | Chao |
| 2017/0151282 A1 | 6/2017 | Discher |
| 2017/0283498 A1 | 10/2017 | Frazier |
| 2018/0051081 A1 | 2/2018 | Frazier |
| 2018/0057592 A1 | 3/2018 | Frazier |
| 2018/0142019 A1 | 5/2018 | Manning |

FOREIGN PATENT DOCUMENTS

| | | |
|---|---|---|
| CN | 103665165 | 3/2014 |
| EP | 0256654 A2 | 2/1988 |
| EP | 1035132 | 9/2000 |
| EP | 1693385 | 8/2006 |
| EP | 2111869 | 10/2009 |
| JP | 2007008895 | 1/2007 |
| WO | 1999012973 | 3/1999 |
| WO | 199940940 A1 | 8/1999 |
| WO | 1999040940 | 8/1999 |
| WO | 200105968 A1 | 1/2001 |
| WO | 2003050295 | 6/2003 |
| WO | 2004096133 A2 | 11/2004 |
| WO | 2008043072 A2 | 4/2008 |
| WO | 2008060785 | 5/2008 |
| WO | 2008060785 A2 | 5/2008 |
| WO | 2009091547 | 7/2009 |
| WO | 2009091601 | 7/2009 |
| WO | 2009131453 A1 | 10/2009 |
| WO | 2011083140 | 7/2011 |
| WO | 2011143624 | 11/2011 |
| WO | 2011143624 A2 | 11/2011 |
| WO | 2013119714 | 8/2013 |
| WO | 2014093678 | 6/2014 |
| WO | 2014093678 A2 | 6/2014 |
| WO | 2014149477 A1 | 9/2014 |
| WO | 2014093678 A3 | 11/2014 |
| WO | 2014123580 | 10/2015 |
| WO | 2015191861 A1 | 12/2015 |
| WO | 2017049251 A2 | 3/2017 |
| WO | 2018075960 | 4/2018 |

OTHER PUBLICATIONS

International Application No. PCT/US2016/052383; International Preliminary Report on Patentability, dated Mar. 20, 2018; 11 pages.
International Application No. PCT/US2016/052383; International Search Report and Written Opinion of the International Search Authority, dated Mar. 1, 2017; 16 pages.
International Application No. PCT/US2017/057716; International Search Report and Written Opinion of the International Search Authority, dated Feb. 21, 2018; 22 pages.
U.S. Appl. No. 14/104,007; Examiner Initiated Interview Summary dated Aug. 14, 2015; 1 page.
U.S. Appl. No. 14/104,007; Notice of Allowance dated Aug. 14, 2015; 14 pages.
U.S. Appl. No. 14/302,348; Affidavit-traversing rejections or objections rule 132 dated Feb. 1, 2017; 17 pages.
U.S. Appl. No. 14/302,348; Final Office Action dated Mar. 13, 2017; 11 pages.
U.S. Appl. No. 14/302,348; Non-Final Office Action dated Aug. 1, 2016; 15 pages.
U.S. Appl. No. 14/302,348; Notice of Allowance dated Oct. 6, 2017; 2 pages.
U.S. Appl. No. 14/302,348; Notice of Allowance dated Sep. 27, 2017; 5 pages.
U.S. Appl. No. 14/737,053; Affidavit-traversing rejections or objections rule 132 dated Feb. 2, 2017; 17 pages.
U.S. Appl. No. 14/737,053; Final Office Action dated Mar. 14, 2017; 11 pages.
U.S. Appl. No. 14/737,053; Non-Final Office Action dated Aug. 2, 2016; 15 pages.
U.S. Appl. No. 14/737,053; Notice of Allowance dated Sep. 25, 2017; 5 pages.
U.S. Appl. No. 14/940,751; Notice of Allowance dated Aug. 4, 2016; 10 pages.
U.S. Appl. No. 14/940,755; Notice of Allowance dated Aug. 4, 2016; 10 pages.
U.S. Appl. No. 15/345,691; Non-Final Office Action dated Dec. 6, 2017; 16 pages.
U.S. Appl. No. 15/820,054; Application as filed dated Nov. 21, 2017; 106 pages.
U.S. Appl. No. 15/871,802; Application as filed dated Jan. 15, 2018; 170 pages.
U.S. Appl. No. 15/871,802; Non-Final Office Action dated Mar. 1, 2018; 15 pages.
"Chain L, Diels Alder Catalytic Antibody Germline Precursor", Database Protein, NCBIM Genbank Accession No. 1A4J_L, (Oct. 10, 2012).
"Chimeric Anti-Human Type VII Collagen Immunoglobulin G1 [Synthetic Construct]", Database Protein, NCBI, Genbank Accession No. ACN 59874.1, (Nov. 20, 2009).
Abcam anti-CD47 antibody [EPR 4150(2)] ab108415, available at www.abcam.com/cd47-antibody-epr41502-ab108415.html (last visited Jul. 20, 2015).
Ahmed et al., "Targeting Cd47 as an Apoptotic Trigger of Human Lung Carcinoma Tumors", Amer Inst Chem Eng. 2005 mtg abstract #457d.
Akewanlop, et al., "Phagocytosis of Breast Cancer Cells Mediated by Anti-Muc-1 Monoclonal Antibody, DF3, and its Bispecific Antibody", Cancer Research, vol. 61, (May 15, 2001).
Almagro, J. et al., Humanization of antibodies, Frontiers in Bioscience 13, 1619-1633, Jan. 1, 2008.
Almagro, J. et al., Progress and Challenges in the Design and Clinical Development of Antibodies for Cancer Therapy, Front Immunol. Jan. 4, 2018;8:1751.
Avent et al., "Monoclonal antibodies that recognize different membrane proteins that are deficient in Rh null, human erythrocytes", Biochem. J. (1988) 251, 499-505.
Baker, Monya, "Cancer and Stem Cells: Beckman Conference", Nature Reports Stem Cells, (Mar. 13, 2008).
Blazar, et al., "CD47 (Integrin-Associated Protein) Engagement of Dendritic Cell and Macrophage Counterreceptors is Required to Prevent the Clearance of Donor Lymphohematopoietic Cells", J. Exp. Med., 194:541-9, (Aug. 20, 2001).
Brown et al., 'Integrin-associated Protein: A 50-kD Plasma Membrane Antigen Physically and Functionally Associated with Integrins', The Journal of Cell Biology, vol. 111, Dec. 1, 1990, pp. 2785-2794.
Brown, Eric J. et al., "Integrin-Associated Protein (CD47) and it's Ligands", Trends in Cell Biology, 11(3):130-5, (2001).
Cameron, C. et al., "Myxoma Virus M128L is Expressed as a Cell Surface CD47-Like Virulence Factor that Contributes to the Downregulation of Macrophage Activation In Vivo", Virology, vol. 337, pp. 55-67 (2005).
Campbell et al., 'An Ovarian Tumor Marker with Homology to Vaccinia Virus Contains an IgV-like Region and Multiple Transmembrane Domains', Cancer Research, vol. 52, Oct. 1, 1992, pp. 5416-5420.
Carter, P., Potent antibody therapeutics by design, Nature Reviews Immunology, vol. 6, 343-357, May 2006.
Chao MP et al., Anti-CD47 antibody synergizes with Rituximab to promote phagocytosis and eradicate non-Hodgkin lymphoma, Cell 2010 plus supplemental info.
Chao, et al., "The CD47-SIRP alpha Pathway in Cancer Immune Evasion and Potential Therapeutic Implications," Curr Opin Immunol., Apr. 2012; 24(2): 225-232.
Chao, et al., "Targeting CD47 Eliminates Human Acute Myeloid Leu-Kemia Stem Cells", May 14, 2008, cited Jan 3, 2017.
Chen, Thomas T. et al., "Expression and Activation of Signal Regulatory Protein Alpha on Astrocytomas", Cancer Research, 64:117-27, (2004).
Cooper, G.M., "The Development and Causes of Cancer", The Cell: A Molecular Approach, (2000), cited Jan 3, 2017.

(56) References Cited

OTHER PUBLICATIONS

Danielsen et al., 'Dysregulation of CD47 and the ligands thrombospondin 1 and 2 in multiple myeloma', British Journal of Haematology, 138, 756-760. (2007).
Declaration of Henry Shelton Earp, with Exhibits HSE-1 and HSE-2.
Declaration of Kristy Richards, with Exhibit KR-1.
Declaration of Ravindra Majeti, with exhibits RM-1 to RM-3 (D3, D3a, D3b).
Edris B et al., Antibody therapy targeting the CD47 protein is effective in a model of aggressive metastatic leiomyosarcoma, PNAS, 2012, 6656-6661.
Epenetos et al., 'Monoclonal antibodies for imaging and therapy', Br. J. Cancer (1989), 59, 152-155.
EPO Register Extract for EP 2240780.
EPO Register Extract for EP 2282772.
Excerpt from the USPTO website relating to assignments of PCT/US09/00319 (WO Publication).
Excerpt from the USPTO website relating to assignments of U.S. Appl. No. 61/011,324 (P1).
Excerpt from the USPTO website relating to assignments of U.S. Appl. No. 61/189,786 (P2).
Finlay WJ et al., Natural and man-made V-gene repertoires for antibody discovery, Front Immunol. Nov. 15, 2012;3:342.
Florian et al., 'Evaluation of normal and neoplastic human mast cells for expression of CD172a (SIRP-alpha), CD47, and SHP-1', Journal of Leukocyte Biology vol. 77, Jun. 2005.
Frazier W A et al., Therapeutic CD47 Antibodies, Vasculox Inc., US20140161799A1, Examiner initiated interview summary, dated Aug. 14, 2015.
Frazier W A et al., Therapeutic CD47 Antibodies, Vasculox Inc., US20140161799A1, Notice of Allowance, dated Aug. 14, 2015.
Frazier W A et al., Therapeutic CD47 Antibodies, Vasculox Inc., WO0140293678A1, International Preliminary Report on Patentability Chapter I, dated Jun. 16, 2015.
Galluzzi, Lorenzo, et al, "Immunogenic cell death in cancer and infectious disease," Nature Reviews, Immunology, vol. 17, Feb. 2017.
Gardai et al., 'Cell-Surface Calreticulin Initiates Clearance of Viable or Apoptotic Cells through trans-Activation of LRP on the Phagocyte', Cell, vol. 123, 321-334, Oct. 21, 2005.
Gresham et al., 'A Novel Member of the Integrin Receptor Family Mediates Arg-Gly-Asp-stimulated Neutrophil Phagocytosis', The Journal of Cell Biology, vol. 108, May 1989, 1935-1943.
Han et al., 'CD47, a Ligand for the Macrophage Fusion Receptor, Participates in Macrophage Multinucleation', The Journal of Biological Chemistry, vol. 275, No. 48, Issue of Dec. 1, pp. 37984-37992, 2000.
Head, et al., "Ligation of CD47 Mediates Phosphatidylserine Expression on Erythrocytes and a Concomitant Loss of Viability in Vitro", British Journal of Haematology, 130:788-90, (2005).
Henson, Peter M. et al., "Apoptotic Cell Removal", Current Biology, 11:R795-R805, (2011).
Humana Press Inc., "Handbook of Cancer Vaccines", Humana Press Inc., 2004.
International Search Report and Written Opinion of the International Searching Authority for PCT/2017/057716 dated Feb. 21, 2018.
International Search Report, PCT Application No. PCT/US2013/074766, dated Oct. 10, 2014, 6 pgs.
Isenberg, J. et al., Treatment of Liver Ischemia/Reperfusion Injury by Limiting Thrombospondin-1/CD47 Signaling, Surgery 144(5), 752-761, 2008.
Isenberg, Jeff et al., "Differential Interactions of Thrombospondin-1, -2 and -4 with CD47 and Effects on cGMP Signaling and Ischemic Injury Response", The Journal of Biological Chemistry, vol. 284, No. 2, (Jan. 9, 2009).
Jaiswal S et al., CD47 is upregulated on circulating hematopoietic stem cells and leukemia cells to avoid phagocytosis, Jul. 24, 2009, Cell 138, 271-285.

Jamieson, Catriona et al., "Increased Expression of CD47 is a Constant Marker in Mouse and Human Myeloid Leukemias", Blood, vol. 106, (2005).
Jiang P et al., Integrin-associated Protein Is a Ligand for the P84 Neural Adhesion Molecule, The Journal of Biological Chemistry, vol. 274, No. 2, Issue of Jaunary 8, 1999, pp. 559-562.
Kaiser et al., 'Expression of insulin-like growth factor receptors I and II in normal human lung and in lung cancer', J Cancer Res Clin Oncol (1993) 119:665-668.
Kenemans, P., CA 125 and OA 3 as target antigens for immunodiagnosis and immunotherapy in ovarian cancer, European Journal of Obstetrics & Gynecology and Reproductive Biology, 36 (1990) 221-238.
Kikuchi et al., "A bivalent single-chain Fv fragment against CD47 induces apoptosis for leukemic cells", Biochemical and Biophysical Research Communications 315 (2004) 912-918.
Kikuchi et al., "Apoptosis inducing bivalent single-chain antibody fragments against CD47 showed antitumor potency for multiple myeloma", Leukemia Research 29 (2005) 445-450.
Kim, Min Jung et al., "Association of CD47 with Natural Killer Cell-Mediated Cytotoxicty of Head-and-Neck Squamous Cell Carcinoma Lines", Tumor Biology, 29:28-34, (2008).
Knapp et al., 'CD Antigens 1989', Blood, vol. 74, No. 4 Sep. 1989: pp. 1448-1450.
Kroemer, G. et al., "Classificatio of Cell Death", Cell Death Difference, 16(1):3-11, (Jan. 2009).
L'Esperance, Sylvain et al., "Gene Expression Profiling of Paired Ovarian Tumors Obtained Prior to and Following Adjuvant Chemotherapy: Molecular Signatures of Chemoresistant Tumors", International Journal of Oncology, 29:5-24, (2006).
Lamy et al., 'CD47 and the 19 kDa Interacting Protein-3 (BNIP3) in T Cell Apoptosis', The Journal of Biological Chemistry, vol. 278, No. 26, Issue of Jun. 27, pp. 23915-23921, 2003.
Latour et al., "Bidirectional Negative Regulation of Human T and Dendritic Cells by CD47 and Its Cognate Receptor Signal-Regulator Protein-alpha: Down-Regulation of IL-12 Responsiveness and Inhibition of Dendritic Cell Activation", The Journal of Immunology, 2001, 167: 2547-2554.
Legrand, et al., 'Functional CD47/Signal Regulatory Protein Alpha (SIRP(alpha)) Interaction is Required for Optimal Human T- and Natural Killer- (NK) Cell Homeostasis in Vivo', Proceedings of the National Academy of Sciences, vol. 108, No. 32, 2001, pp. 13224-13229.
Lindberg et al., 'Molecular Cloning of Integrin-associated Protein: An Immunoglobulin Family Member with Multiple Membrane-spanning Domains Implicated in CvB3-dependent Ligand Binding', The Journal of Cell Biology, vol. 123, No. 2, Oct. 1993, 485-496.
Lindberg et al., 'Rh-related Antigen CD47 Is the Signal-transducer Integrin-associated Protein', The Journal of Biological Chemistry, vol. 269, No. 3, Issue of Jan. 21, pp. 1567-1570, 1994.
Lindberg F P et al., Decreased resistance to bacterial infection and granulocyte defects in IAP-deficient mice, Science New Series, vol. 274, No. 5288 (Nov. 1, 1996), pp. 795-798.
Liu et al., 'Signal Regulatory Protein (SIRP-alpha), a Cellular Ligand for CD47, Regulates Neutrophil Transmigration', The Journal of Biological Chemistry, vol. 277, No. 12, Issue of Mar. 22, pp. 10028-10036, 2002.
Liu, A. 'Differential Expression of Cell Surface Molecules in Prostate Cancer Cells', Cancer Research 60, 3429-3434, Jul. 1, 2000.
Majeti R et al., CD47 is an adverse prognostic factor and therapeutic antibody target on human acute myeloid leukemia stem cells, Cell 2009, 138, p. 286-299.
Majeti, "Monoclonal antibody therapy directed against human acute myeloid leukemia stem cells.", Oncogene, (Nov. 15, 2010), vol. 30, No. 9, pp. 1009-1019, XP055094665.
Majeti, et al., "Acute Myeloid Leukemia—Therapy, Excluding Transplantation", Blood, vol. 112, (Nov. 16, 2008).
Majeti, Ravindra et al., "CD47 is an Independent Prognostic Factor and Therapeutic Antibody Target on Human Acute Myeloid Leukemia Stem Cells", Blood, vol. 112, (2008).
Manna et al, 'The Mechanism of CD47-Dependent Killing of T Cells: Heterotrimeric Gi-Dependent Inhibition of Protein Kinase A',

(56) References Cited

OTHER PUBLICATIONS

The Journal of Immunology, (Apr. 1, 2003), vol. 170, No. 7, doi:10.4049/jimmunol.170.7.3544, ISSN 0022-1767, pp. 3544-3553, XP055116597.
Manna et al., 'CD47 Mediates Killing of Breast Tumor Cells via Gi-Dependent Inhibition of Protein Kinase A', Cancer Research 64, 1026-1036, Feb. 1, 2004.
Mateo et al., 'CD47 ligation induces caspase-independent cell death in chronic lymphocytic leukemia', Nature Medicine, vol. 5, No. 11, Nov. 1999, pp. 1277-1284.
Mawby et al., "Isolation and characterization of CD47 glycoprotein: a multispanning membrane protein which is the same as integrin-associated protein (IAP) and the ovarian tumour marker OA3", Biochem. J. (1994) 304, 525-530.
Motegi et al., "Role of CD47-SHPS-1 system in regulation of cell migration", The EMBO Journal vol. 22, No. 11, pp. 2634-2644, 2003.
Mughal, Tariq I. et al., "Understanding Leukemias, Lymphomas and Myelomas", Taylor & Francis, pp. 47-48, 53, (2006).
Munn, "Phagocytosis of Tumor Cells by Human Monocytes Cultured in Recombinant Macrophage Colony-Stimulating Factor", J. Exp. Med., vol. 172, (Jul. 1990).
National Cancer Institute, "Cancer Classification", cited Jan 3, 2017.
Nishiyama et al., 'Overexpression of Integrin-associated Protein (CD47) in Rat Kidney Treated with a Renal Carcinogen, Ferric Nitrilotriacetate', Jpn. J. Cancer Res. 88, 120-128, Feb. 1997.
Obeid M et al., Ecto-calreticulin in immunogenic chemotherapy, Immunological Reviews 2007, vol. 220: 22-34.
Oldenborg PA et al., CD47-signal regulatory protein alpha (SIRPa) regulates Fcgamma and complement receptor-mediated phagocytosis, Journal Exp Med, vol. 193, No. 7, Apr. 2, 2001 p. 855-861.
Oldenborg, et al., "Role of CD47 in Erythroid Cells and in Autoimmunity", Leukemia & Lymphoma, 45(7):1319-27, (2004).
Olsson, et al., "Platelet Homeostasis is Regulated by Platelet Expression of CD47 Under Normal Conditions and in Passive Immune Thromocytopenia", Blood, 105(9):3577-82, (May 1, 2005).
Per-Arne Oldenborg et al., 'Role of CD47 as a Marker of Self on Red Blood Cells', Science vol. 288, Jun. 16, 2000, pp. 2051-2054.
Pettersen et al., 'CD99 Signals Caspase-Independent T Cell Death', The Journal of Immunology, 2001, 166: 4931-4942.
Pettersen et al., "CD47 Signals T Cell Death", The Journal of Immunology, 1999, 162: 7031-7040.
Pietsch, et al., "Anti-Leukemic Activity and Tolerability of Anti-Human CD47 Monoclonal Antibodies", American Association of Cancer Research Abstract 2470, (Jan. 2017).
Poels et al., "Monoclonal Antibody Against Human Ovarian Tumor-Associated Antigens", JNCI, vol. 76, 1986, 781-791.
Raetz, Elizabeth A. et al., "Gene Expression Profiling Reveals Intrinsic Differences Between T-cell Acute Lymphoblastic Leukemia and T-cell Lymphoblastic Lymphoma", Pediatr. Bllod Cancer, (47):130-40, (2006).
Rebres et al., "Novel CD47-Dependent Intercellular Adhesion Modulates Cell Migration", Journal of Cellular Physiology, 205:182-193 (2005).
Reichert, Janice M., "Marketed Therapeutic Antibodies Compendium", mAbs, Lades Bioscience, 4(3):413-5, (2012).
Request form for PCT/US2009/000319.
Roberts, D. et al., The Matricellular Protein Thrombospondin-1 Globally Regulates Cardiovascular Function and Responses to Stress via CD47, Matrix Biology 31(3), 162-169, 2012.
Roitt A. et al., Immunology (Published by "Mir" Publishing House, Moscow, 2000, p. 110-111.
Sagawa et al., 'A new disulfide-linked dimer of a single-chain antibody fragment against human CD47 induces apoptosis in lymphoid malignant cells via the hypoxia inducible factor-1 alpha pathway', Cancer Sci, Jun. 2011, vol. 102, No. 6, 1208-1215.
Samani et al., 'The Role of the IGF System in Cancer Growth and Metastasis: Overview and Recent Insights', Endocrine Reviews 28(1):20-47, (2007).

Science Daily, "Scientists Discover New Way to Distinguish Self from Other", cited Jan 22, 2017.
Seiffert et al., 'Human Signal-Regulatory Protein Is Expressed on Normal, But Not on Subsets of Leukemic Myeloid Cells and Mediates Cellular Adhesion Involving Its Counterreceptor CD47' Blood, vol. 94, No. 11 Dec. 1, 1999: pp. 3633-3643.
Sick E et al., CD47 update: a multifaceted actor in the tumour microenvironment of potential therapeutic interest, Br J Pharmacol. Dec. 2012;167(7): pp. 1415-1430.
Singer M. et al., Genes and Genomes (Published by "Mir" Publishing House, Moscow, 1998, vol. 1, p. 63-64.
Sonderegger S et al., Interleukin (IL)11 mediates protein secretion and modification in human extravillous trophoblasts, Hum Reprod. Oct. 2011;26(10):2841-9.
Soto-Pantoja, et al., "Inhibitory Signaling Through Signal Regulatory Protein-A is Not Sufficient to Explain the Antitumor Activities of CD47 Antibodies", PNAS, 109:E2842, (2012).
Strome, Scott et al., "A Mechanistic Perspective of Monoclonal Antibodies in Cancer Therapy Beyond Target-Related Effects", The Oncologist, vol. 12, (2007).
Submissions dated Jul. 21, 2011 filed during prosecution of U.S. Appl. No. 12/321,215, a continuation-in-part of U.S. Appl. No. 11/528,890.
Submissions of James Poole Limited of Dec. 22, 2016 on EP2282772.
Subramanian et al., 'Species- and cell type-specific interactions between CD47 and human SIRP-alpha', Blood, Mar. 15, 2006, 107(6):2548-56.
Subramanian S. et al., Phylogenetic divergence of CD47 interactions with human signal regulatory protein alpha reveals locus of species specificity. Implications for the binding site, J Biol Chem. Jan. 19, 2007;282(3):1805-1818.
Takizawa, Hitoshi et al., "Macrophage Tolerance: CD47-SIRP-Alpha-Mediated Signals Matter", Nature Immunology, (8):1287-9, (2007).
Tamoto et al., 'Gene-Expression Profile Changes Correlated with Tumor Progression and Lymph Node Metastasis in Esophageal Cancer', Clinical Cancer Research, vol. 10, 3629-3638, Jun. 1, 2004.
Ticchioni et al., "Integrin-Associated Protein (CD47) Is a Comitogenic Molecule on CD3-Activated Human T Cells", The Journal of Immunology, 1997, 158: 677-684.
Trounson, "Stem Cells, Plasticity and Cancer—Uncomfortable Bed Fellows", Development, vol. 131, (2004).
Uno et al., "Antitumor activity of a monoclonal antibody against CD47 in xenograft models of human leukemia", Oncology Reports 17: 1189-1194, 2007.
USPTO Assignment Database Extract.
Van Beek, Ellen M. et al., "Signal Regulatory Proteins in the Immune System", J. Immunol., ISSN: 175:7781-7, (Dec. 2005).
Van Den Berg, Timo K. et al., "Innate Immune 'Self' Recognition: A Role for CD47-SIRPa Interactions in Hemotopoietic Stem Transplantation", Trends Immunology, 29(5):203-6, (Apr. 3, 2008).
Van Ravenswaay Claasen et al., "Analysis of Production, Purification, and Cytolytic Potential of Bi-Specific Antibodies Reactive With Ovarian-Carcinoma-Associated Antigens and the T-Cell Antigen CD3", Int. J. Cancer: 55, 128-136 (1993).
Vermeer DW et al., Radiation-induced loss of cell surface CD47 enhances immune-mediated clearance of human papillomavirus-positive cancer, Int J Cancer. Jul. 2013;133(1):120-9.
Vernon-Wilson et al., 'CD47 is a ligand for rat macrophage membrane signal regulatory protein SIRP (0X41) and human SIRP alpha 1', Eur. J. Immunol. 2000. 30: 2130-2137.
Wang, Hui et al., "Attenuation of Phagocytosis of Xenogeneic Cells by Manipulating CD47", Blood, vol. 109, No. 2, (Jan. 15, 2007).
Webpage relating to the award of a grant for a study aimed at developing anti-CD47 antibodies for leukemia treatment.
Weiskopf and Weissman, "Macrophages are Critical Effectors of Antibody Therapies for Cancer", mAbs, vol. 7, No. 2, (2015).
Weiskopf, et al., "Engineered SIRPa Variants as Immunotherapeutic Adjuvants to Anticancer Antibodies", Science, 341:88-91, (Jul. 5, 2013).
Weissman, Irving et al., "The E. Donnall Thomas Lecture; Normal and Neoplastic Stem Cells", Biol. Blood Marrow Transplant, (2008).

(56) References Cited

OTHER PUBLICATIONS

Wikipedia, "Cancer Immunotherapy", cited Jan. 8, 2017.
Wikipedia, "Monoclonal Antibody", cited Jan. 8, 2017.
Willingham S B et al., The CD47-signal regulatory protein alpha (SIRPa) interaction is a therapeutic target for human solid tumors, PNAS, Apr. 24, 2012, vol. 109, No. 17, p. 6662-6667.
WO2015191861, International Search Report and Written Opinion, dated Oct. 15, 2015, 6 pages.
Yamao T et al., Negative regulation of platelet clearance and of the macrophage phagocytic response by the transmembrane glycoprotein SHPS-1, Journal of Biological Chemistry, vol. 277, No. 42, Issue of Oct. 18, 2002, pp. 39833-39839.
Yang Y et al., Wogonin induced calreticulin/annexin A1 exposure dictates the immunogenicity of cancer cells in a PERK/AKT dependent manner, PLoS One. 2012;7(12):e50811.
Zhan et al., 'Global gene expression profiling of multiple myeloma, monoclonal gammopathy of undetermined significance, and normal bone marrow plasma cells', Blood, Mar. 1, 2002, z vol. 99, No. 5.
Zhao, et al., "Is Targeting of CD47-SIRPa Enough for Treating Hematopoietic Malignancy", Blood, 119:4333-4, (May 3, 2012).
Zipin-Roitman A et al., CXCL10 promotes invasion-related properties in human colorectal carcinoma cells, Cancer Res. Apr. 1, 2007;67(7):3396-405.
U.S. Appl. No. 15/345,691; Final Office Action dated Jul. 12, 2018; 14 pages.
Chao, M. et al., "Anti-CD47 antibody synergizes with rituximab to promote phagocytosis and eradicate non-Hodgkin lymphoma", Cell, 142(5):699-713, (2010).
Cioffi, M. et al., "Inhibition of CD47 Effectively Targets Pancreatic Cancer Stem Cells via Dual Mechanisms", Clinical Cancer Research, 21(10):2325-37, (2015).
Hanahan, D. et al., "The hallmarks of cancer", Cell, 100(1):57-70, (2000).
Johnstone, R. et al., "Apoptosis: A Link between Cancer Genetics and Chemotherapy", Cell, 108:153-64, (2002).
Liu, J. et al., "Pre-Clinical Development of a Humanized Anti-CD47 Antibody with Anti-Cancer Therapeutic Potential", PLoS One, 10(9):e0137345, (2015).
McKenzie, S. et al., "Apoptosis evasion: the role of survival pathways in prostate cancer progression and therapeutic resistance.", J. Cell Biochem., 97(1):18-32, (2006).
Weiskopf, K. et al., "CD47-blocking immunotherapies stimulate macrophage-mediated destruction of small-cell lung cancer", J Clin Invest., 126(7):2610-20, (2016).
Written Submission of Opposition to EP2242512 Following Preliminary Opinion on Behalf of James Roger Wilding, (Jun. 27, 2018); 13 pages.
Written Submission of Opposition to EP2242512 Following Preliminary Opinion on Behalf of Opponent Avidity IP LTD, (Jun. 27, 2018); 29 pages.
Written Submission of Opposition to EP2242512 Following Preliminary Opinion on Behalf of Surface Oncology, Inc., (Jun. 27, 2018); 21 pages.
Written Submission of Opposition to EP2242512 Following Preliminary Opinion on Behalf of the Board of Trustees of the Leland Stanford Junior University, (Jun. 27, 2018); 16 pages.
Written Submission of Opposition to EP2242512 Following Preliminary Opinion on Behalf of Tioma Therapeutics, Inc., (Jun. 27, 2018); 21 pages.
Zhao, X. et al., "CD47-signal regulatory protein-(SIRP ) interactions form a barrier for antibody-mediated tumor cell destruction", Proceedings of the National Academy of Sciences, 108(45):18342-7, (2011).

\* cited by examiner

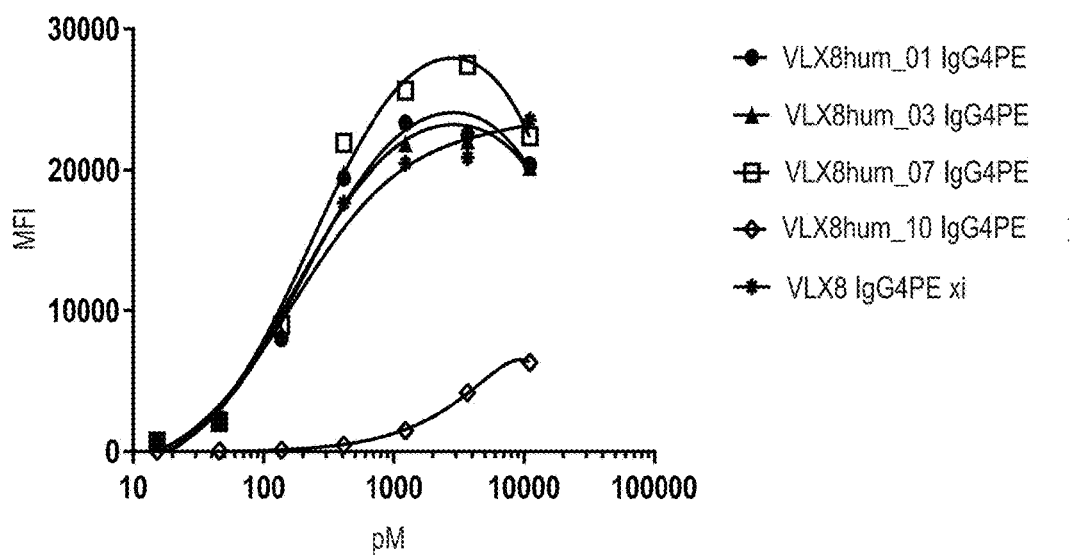
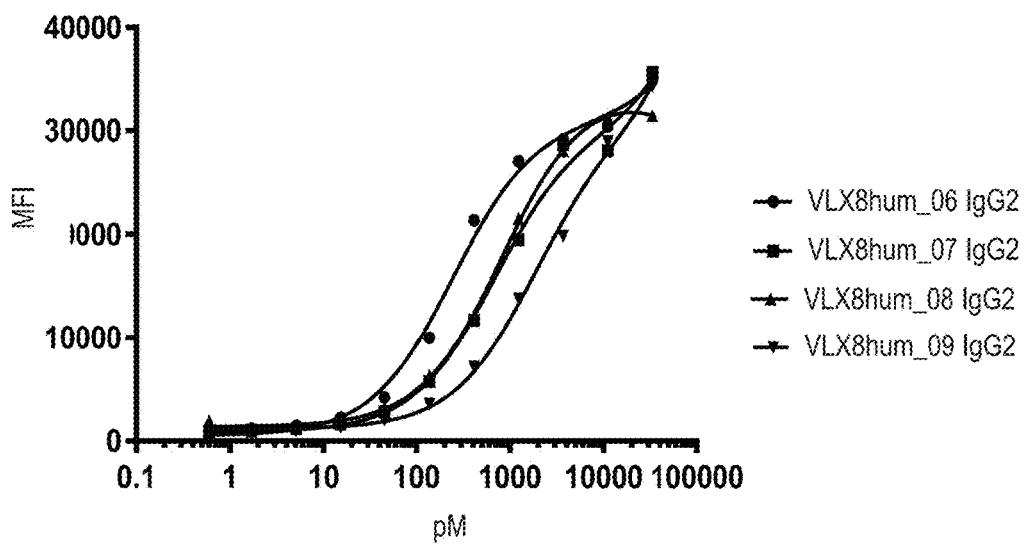

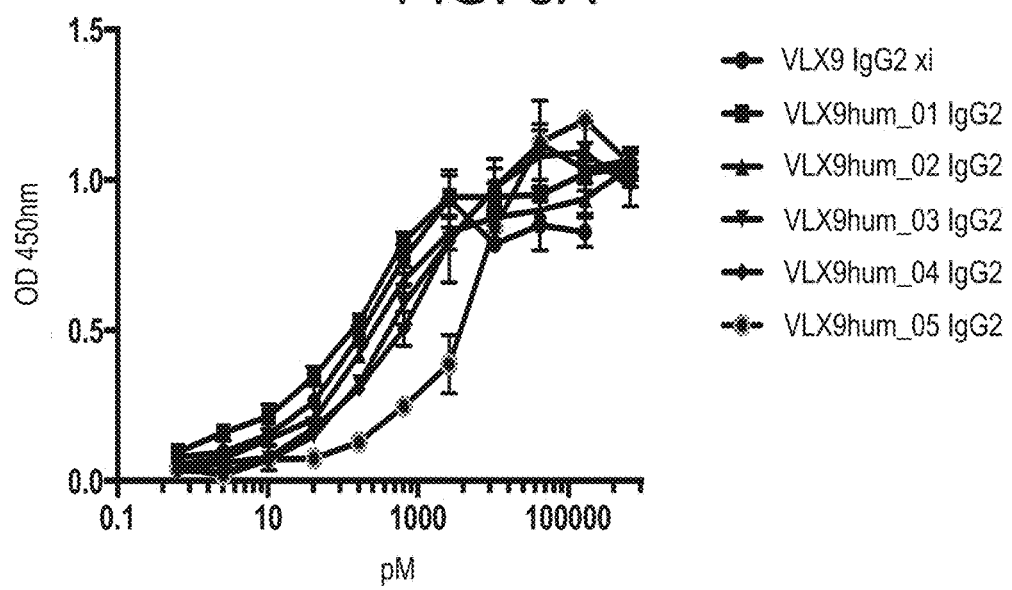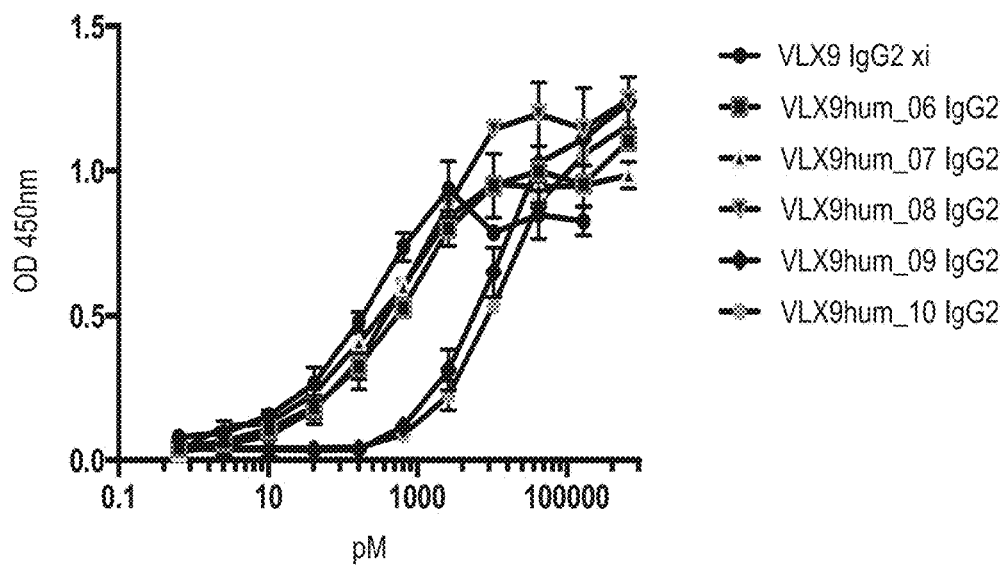

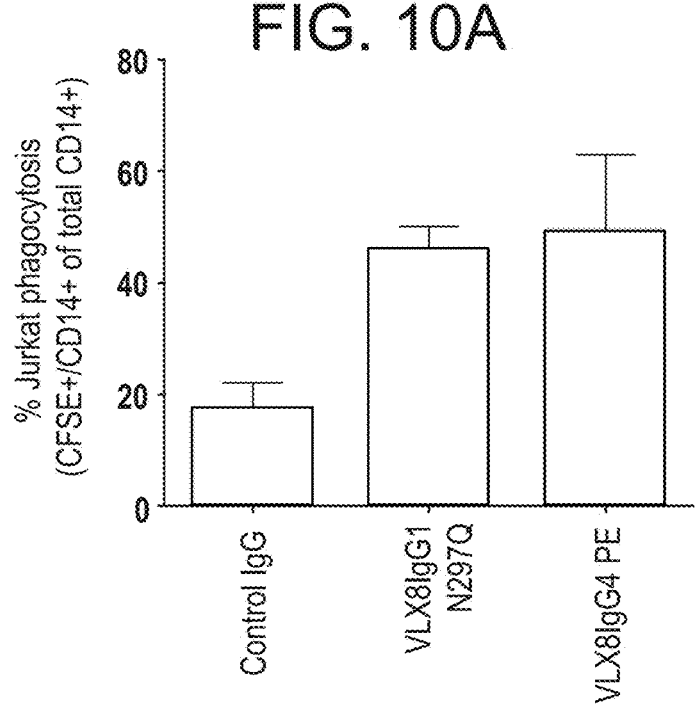
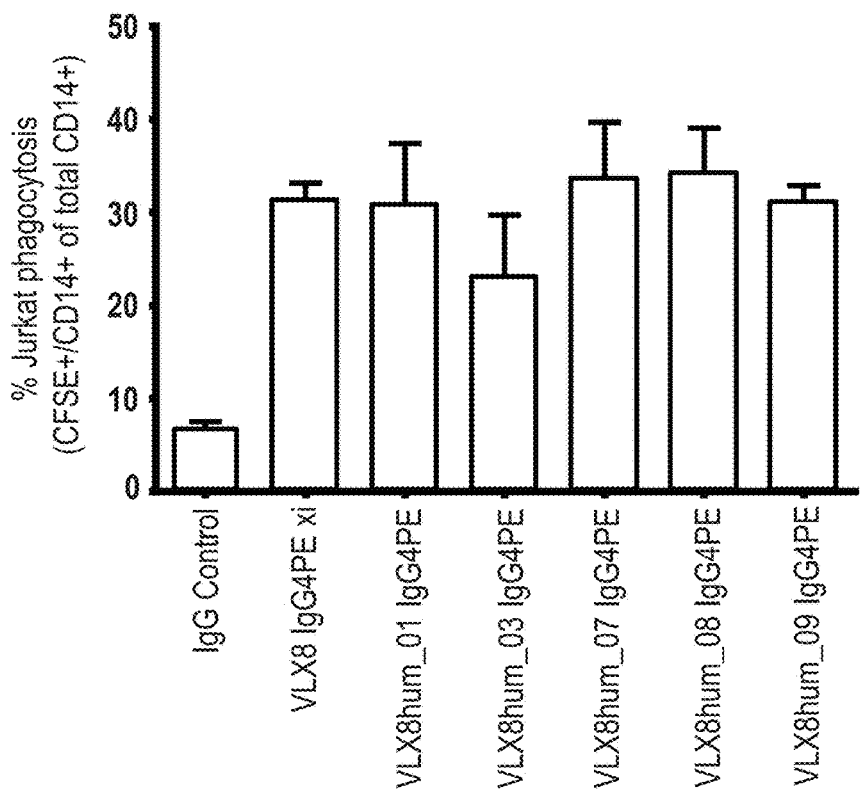

FIG. 22

SEQUENCE LISTING

```
<160> NUMBER OF SEQ ID NOS: 104

<210> SEQ ID NO 1
<211> LENGTH: 10
<212> TYPE: PRT
<213> ORGANISM: Artificial Sequence
<220> FEATURE:
<223> OTHER INFORMATION: Vx4-HCDR1

<400> SEQUENCE: 1

Gly Tyr Thr Phe Thr Asn Tyr Val Ile His
1               5                   10
```

<210> SEQ ID NO 2
<211> LENGTH: 10
<212> TYPE: PRT
<213> ORGANISM: Artificial Sequence
<220> FEATURE:
<223> OTHER INFORMATION: Vx8-HCDR1

<400> SEQUENCE: 2

Gly Tyr Ser Phe Thr Asn Tyr Tyr Ile His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Vx9-HCDR1

<400> SEQUENCE: 3

Gly Tyr Thr Phe Thr Asn Tyr Trp Ile His
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Vx4-HCDR2

<400> SEQUENCE: 4

Tyr Ile Tyr Pro Tyr Asn Asp Gly Ile Leu Tyr Asn Glu Lys Phe Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Vx8-HCDR2

<400> SEQUENCE: 5

Tyr Ile Asp Pro Leu Asn Gly Asp Thr Thr Tyr Asn Gln Lys Phe Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Vx9-HCDR2

<400> SEQUENCE: 6

Tyr Thr Asp Pro Arg Thr Asp Tyr Thr Glu Tyr Asn Gln Lys Phe Lys
1               5                   10                  15

Asp

<210> SEQ ID NO 7
<211> LENGTH: 8
<212> TYPE: PRT
<213> ORGANISM: Artificial Sequence
<220> FEATURE:
<223> OTHER INFORMATION: Vx4-HCDR3

```
<400> SEQUENCE: 7

Gly Gly Tyr Tyr Val Pro Asp Tyr
1               5

<210> SEQ ID NO 8
<211> LENGTH: 8
<212> TYPE: PRT
<213> ORGANISM: Artificial Sequence
<220> FEATURE:
<223> OTHER INFORMATION: Vx4-HCDR3

<400> SEQUENCE: 8

Gly Gly Tyr Tyr Val Tyr Asp Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: Vx8-HCDR3

<400> SEQUENCE: 9

Gly Gly Lys Arg Ala Met Asp Tyr
1               5

<210> SEQ ID NO 10
<211> LENGTH: 8
<212> TYPE: PRT
<213> ORGANISM: Artificial Sequence
<220> FEATURE:
<223> OTHER INFORMATION: Vx9-HCDR3

<400> SEQUENCE: 10

Gly Gly Arg Val Gly Leu Gly Tyr
1               5

<210> SEQ ID NO 11
<211> LENGTH: 16
<212> TYPE: PRT
<213> ORGANISM: Artificial Sequence
<220> FEATURE:
<223> OTHER INFORMATION: Vx4-LCDR1

<400> SEQUENCE: 11

Arg Ser Arg Gln Ser Ile Val His Thr Asn Gly Asn Thr Tyr Leu Gly
1               5                   10                  15

<210> SEQ ID NO 12
<211> LENGTH: 11
<212> TYPE: PRT
<213> ORGANISM: Artificial Sequence
<220> FEATURE:
<223> OTHER INFORMATION: Vx8-LCDR1

<400> SEQUENCE: 12

Arg Ala Ser Gln Asp Ile Ser Asn Tyr Leu Asn
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Vx8-LCDR1
```

```
<400> SEQUENCE: 13

Arg Ala Ser Gln Ser Ile Ser Asn Tyr Leu Asn
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Vx9-LCDR1

<400> SEQUENCE: 14

Arg Ser Ser Gln Asn Ile Val Gln Ser Asn Gly Asn Thr Tyr Leu Glu
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: KVSNRFS

<400> SEQUENCE: 15

Lys Val Ser Asn Arg Phe Ser
1               5

<210> SEQ ID NO 16
<211> LENGTH: 7
<212> TYPE: PRT
<213> ORGANISM: Artificial Sequence
<220> FEATURE:
<223> OTHER INFORMATION: Vx8-LCDR2

<400> SEQUENCE: 16

Tyr Thr Ser Arg Leu Tyr Ser
1               5

<210> SEQ ID NO 17
<211> LENGTH: 7
<212> TYPE: PRT
<213> ORGANISM: Artificial Sequence
<220> FEATURE:
<223> OTHER INFORMATION: Vx9-LCDR2

<400> SEQUENCE: 17

Lys Val Phe His Arg Phe Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Vx4-LCDR3

<400> SEQUENCE: 18

Phe Gln Gly Ser His Val Pro Tyr Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Vx8-LCDR3

<400> SEQUENCE: 19
```

Gln Gln Gly Asn Thr Leu Pro Trp Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Vx9-LCDR3

<400> SEQUENCE: 20

Phe Gln Gly Ser His Val Pro Trp Thr
1               5

<210> SEQ ID NO 21
<211> LENGTH: 117
<212> TYPE: PRT
<213> ORGANISM: Artificial Sequence
<220> FEATURE:
<223> OTHER INFORMATION: Vx4murH01

<400> SEQUENCE: 21

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Arg Arg Pro Gly Gln Gly Leu Glu Trp Ile
        35                  40                  45

Gly Tyr Ile Tyr Pro Tyr Asn Asp Gly Ile Leu Tyr Asn Glu Lys Phe
    50                  55                  60

Lys Gly Lys Ala Thr Val Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Gly Gly Tyr Tyr Val Pro Asp Tyr Trp Gly Gln Gly Thr Thr
            100                 105                 110

Leu Thr Val Ser Ser
        115

<210> SEQ ID NO 22
<211> LENGTH: 117
<212> TYPE: PRT
<213> ORGANISM: Artificial Sequence
<220> FEATURE:
<223> OTHER INFORMATION: Vx4mur-H02

<400> SEQUENCE: 22

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Arg Arg Pro Gly Gln Gly Leu Glu Trp Ile
        35                  40                  45

Gly Tyr Ile Tyr Pro Tyr Asn Asp Gly Ile Leu Tyr Asn Glu Lys Phe
    50                  55                  60

Lys Gly Lys Ala Thr Val Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Gly Gly Tyr Tyr Val Pro Asp Tyr Trp Gln Gly Thr Leu
                100                 105                 110

Val Thr Val Ser Ser
        115

<210> SEQ ID NO 23
<211> LENGTH: 117
<212> TYPE: PRT
<213> ORGANISM: Artificial Sequence
<220> FEATURE:
<223> OTHER INFORMATION: Vx4humH01

<400> SEQUENCE: 23

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
            20                  25                  30

Val Ile His Trp Leu Arg Gln Ala Pro Gly Gln Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Val Pro Asp Tyr Trp Gly Gln Ala Thr Leu
                100                 105                 110

Val Thr Val Ser Ser
        115

<210> SEQ ID NO 24
<211> LENGTH: 117
<212> TYPE: PRT
<213> ORGANISM: Artificial Sequence
<220> FEATURE:
<223> OTHER INFORMATION: Vx4humH02

<400> SEQUENCE: 24

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
            20                  25                  30

Val Ile His Trp Leu Arg Gln Ala Pro Gly Gln Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Tyr Tyr Val Tyr Asp Tyr Trp Gly Gln Ala Thr Leu
                100                 105                 110

Val Thr Val Ser Ser
        115

<210> SEQ ID NO 25
<211> LENGTH: 117
<212> TYPE: PRT
<213> ORGANISM: Artificial Sequence -continued

```
<220> FEATURE:
<223> OTHER INFORMATION: Vx4humH03

<400> SEQUENCE: 25

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn Tyr
            20                  25                  30

Val Ile His Trp Val Gln Gln Ala Pro Gly Lys Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Tyr Tyr Val Pro Asp Tyr Trp Gly Gln Gly Thr Thr
            100                 105                 110

Val Thr Val Ser Ser
        115

<210> SEQ ID NO 26
<211> LENGTH: 117
<212> TYPE: PRT
<213> ORGANISM: Artificial Sequence
<220> FEATURE:
<223> OTHER INFORMATION: Vx4humH04

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Val Ile His Trp Val Arg Gln Met Pro Gly Lys Gly Leu Glu Trp Met
        35                  40                  45

Gly Tyr Ile Tyr Pro Tyr Asn Asp Gly Ile Leu Tyr Asn Glu Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Tyr Val Pro Asp Tyr Trp Gly Gln Gly Thr Thr
            100                 105                 110

Val Thr Val Ser Ser
        115

<210> SEQ ID NO 27
<211> LENGTH: 117
<212> TYPE: PRT
<213> ORGANISM: Artificial Sequence
<220> FEATURE:
<223> OTHER INFORMATION: Vx4humH05

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

Val Ile His Trp Val Arg Gln Ala Pro Gly Gln Gly Leu Glu Trp Met
         35                  40                  45

Gly Tyr Ile Tyr Pro Tyr Asn Asp Gly Ile Leu Tyr Asn Glu Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Gly Tyr Tyr Val Pro Asp Tyr Trp Gly Gln Gly Thr Thr
                100                 105                 110

Val Thr Val Ser Ser
        115

<210> SEQ ID NO 28
<211> LENGTH: 117
<212> TYPE: PRT
<213> ORGANISM: Artificial Sequence
<220> FEATURE:
<223> OTHER INFORMATION: Vx8murH03

<400> SEQUENCE: 28

Glu Val Gln Leu Gln Gln Ser Gly Pro Glu Leu Met Lys Pro Gly Ala
 1               5                  10                  15

Ser Val Lys Ile Ser Cys Lys Ala Ser Gly Tyr Ser Phe Thr Asn Tyr
                 20                  25                  30

Tyr Ile His Trp Val Asn Gln Ser His Gly Lys Ser Leu Glu Trp Ile
         35                  40                  45

Gly Tyr Ile Asp Pro Leu Asn Gly Asp Thr Thr Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Arg Leu Ser Ser Leu Thr Ser Ala Asp Ser Ala Val Tyr Tyr Cys
                 85                  90                  95

Ala Arg Gly Gly Lys Arg Ala Met Asp Tyr Trp Gly Gln Gly Thr Ser
                100                 105                 110

Val Thr Val Ser Ser
        115

<210> SEQ ID NO 29
<211> LENGTH: 117
<212> TYPE: PRT
<213> ORGANISM: Artificial Sequence
<220> FEATURE:
<223> OTHER INFORMATION: Vx8humH06

<400> SEQUENCE: 29

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Asn Tyr
                 20                  25                  30

Tyr Ile His Trp Val Arg Gln Ala Pro Gly Gln Gly Leu Glu Trp Met
         35                  40                  45

Gly Tyr Ile Asp Pro Leu Asn Gly Asp Thr Thr Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

```
Ala Arg Gly Gly Lys Arg Ala Met Asp Tyr Trp Gln Gly Thr Leu
            100                 105                 110

Val Thr Val Ser Ser
        115

<210> SEQ ID NO 30
<211> LENGTH: 117
<212> TYPE: PRT
<213> ORGANISM: Artificial Sequence
<220> FEATURE:
<223> OTHER INFORMATION: Vx8humH07

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gln Gly Thr Leu
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<223> OTHER INFORMATION: Vx8humH08

<400> SEQUENCE: 31

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile His Trp Val Arg Gln Met Pro Gly Lys Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Lys Arg Ala Met Asp Tyr Trp Gln Gly Thr Leu
            100                 105                 110

Val Thr Val Ser Ser
        115

<210> SEQ ID NO 32
<211> LENGTH: 117
<212> TYPE: PRT
```

```
<213> ORGANISM: Artificial Sequence
<220> FEATURE:
<223> OTHER INFORMATION: >Vx8humH09

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
                100                 105                 110

Val Thr Val Ser Ser
            115

<210> SEQ ID NO 33
<211> LENGTH: 117
<212> TYPE: PRT
<213> ORGANISM: Artificial Sequence
<220> FEATURE:
<223> OTHER INFORMATION: Vx8humH10

<400> SEQUENCE: 33

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile His Trp Val Arg Gln Met Pro Gly Lys Gly Leu Glu Trp Met
        35                  40                  45

Gly Tyr Ile Asp Pro Leu Asn Gly Asp Thr Thr Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Lys Arg Ala Met Asp Tyr Trp Gly Arg Gly Thr Leu
                100                 105                 110

Val Thr Val Ser Ser
            115

<210> SEQ ID NO 34
<211> LENGTH: 117
<212> TYPE: PRT
<213> ORGANISM: Artificial Sequence
<220> FEATURE:
<223> OTHER INFORMATION: Vx8humH11

<400> SEQUENCE: 34

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Ser Phe Thr Asn Tyr
            20                  25                  30
```

Tyr Ile His Trp Leu Arg Gln Ala Pro Gly Gln Gly Leu Glu Trp Met
            35                  40                  45

Gly Tyr Ile Asp Pro Leu Asn Gly Asp Thr Thr Tyr Asn Gln Lys Phe
        50                  55                  60

Lys Gly Arg Val Thr Met Thr Ser Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Gly Lys Arg Ala Met Asp Tyr Trp Gly Gln Ala Thr Leu
                100                 105                 110

Val Thr Val Ser Ser
            115

<210> SEQ ID NO 35
<211> LENGTH: 117
<212> TYPE: PRT
<213> ORGANISM: Artificial Sequence
<220> FEATURE:
<223> OTHER INFORMATION: Vx9murH04

<400> SEQUENCE: 35

Gln Val Gln Leu Gln Gln Phe Gly Ala Glu Leu Ala Lys Pro Gly Ala
1               5                   10                  15

Ser Val Gln Met Ser Cys Lys Ala Ser Gly Tyr Thr Phe Thr Asn Tyr
            20                  25                  30

Trp Ile His Trp Val Lys Gln Arg Pro Gly Gln Gly Leu Glu Trp Ile
            35                  40                  45

Gly Tyr Thr Asp Pro Arg Thr Asp Tyr Thr Glu Tyr Asn Gln Lys Phe
        50                  55                  60

Lys Asp Lys Ala Thr Leu Ala Ala Asp Arg Ser Ser Ser Thr Ala Tyr
65                  70                  75                  80

Met Arg Leu Ser Ser Leu Thr Ser Glu Asp Ser Ala Val Tyr Tyr Cys
                85                  90                  95

Ala Gly Gly Gly Arg Val Gly Leu Gly Tyr Trp Gly His Gly Ser Ser
                100                 105                 110

Val Thr Val Ser Ser
            115

<210> SEQ ID NO 36
<211> LENGTH: 117
<212> TYPE: PRT
<213> ORGANISM: Artificial Sequence
<220> FEATURE:
<223> OTHER INFORMATION: Vx9humH12

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
            35                  40                  45

Gly Tyr Thr Asp Pro Arg Thr Asp Tyr Thr Glu Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                            85                  90                  95

Ala Arg Gly Gly Arg Val Gly Leu Gly Tyr Trp Gly Gln Gly Thr Leu
            100                 105                 110

Val Thr Val Ser Ser
        115

<210> SEQ ID NO 37
<211> LENGTH: 117
<212> TYPE: PRT
<213> ORGANISM: Artificial Sequence
<220> FEATURE:
<223> OTHER INFORMATION: Vx9humH13

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Tyr Thr Asp Pro Arg Thr Asp Tyr Thr Glu Tyr Asn Gln Lys Phe
    50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: Vx9humH14

<400> SEQUENCE: 38

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Ile His Trp Val Arg Gln Met Pro Gly Lys Gly Leu Glu Trp Met
        35                  40                  45

Gly Tyr Thr Asp Pro Arg Thr Asp Tyr Thr Glu Tyr Asn Gln Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser
        115

<210> SEQ ID NO 39
<211> LENGTH: 117
```

```
<212> TYPE: PRT
<213> ORGANISM: Artificial Sequence
<220> FEATURE:
<223> OTHER INFORMATION: Vx9humH15

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Tyr Thr Asp Pro Arg Thr Asp Tyr Thr Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser
            115

<210> SEQ ID NO 40
<211> LENGTH: 117
<212> TYPE: PRT
<213> ORGANISM: Artificial Sequence
<220> FEATURE:
<223> OTHER INFORMATION: Vx9humH16

<400> SEQUENCE: 40

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Ile His Trp Val Arg Gln Met Pro Gly Lys Gly Leu Glu Trp Met
        35                  40                  45

Gly Tyr Thr Asp Pro Arg Thr Asp Tyr Thr Glu Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser
            115

<210> SEQ ID NO 41
<211> LENGTH: 112
<212> TYPE: PRT
<213> ORGANISM: Artificial Sequence
<220> FEATURE:
<223> OTHER INFORMATION: Vx4murL01

<400> SEQUENCE: 41

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
```

```
            20                  25                  30
Asn Gly Asn Thr Tyr Leu Gly Trp Phe Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Vx4murL02

<400> SEQUENCE: 42

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
            20                  25                  30

Asn Gly Asn Thr Tyr Leu Gly Trp Phe Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Thr Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gln Gly Thr Lys Val Glu Ile Lys
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Vx4humL01

<400> SEQUENCE: 43

Asp Ile Val Met Thr Gln Ser Pro Leu Ser Leu Pro Val Thr Pro Gly
1               5                   10                  15

Glu Pro Ala Ser Ile Ser Cys Arg Ser Arg Gln Ser Ile Val His Thr
            20                  25                  30

Asn Gly Asn Thr Tyr Leu Gly Trp Tyr Leu Gln Lys Pro Gly Gln Ser
            35                  40                  45

Pro Arg Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Phe Gln Gly
                85                  90                  95

Ser His Val Pro Tyr Thr Phe Gly Gln Gly Thr Lys Leu Glu Ile Lys
            100                 105                 110
```

```
<210> SEQ ID NO 44
<211> LENGTH: 112
<212> TYPE: PRT
<213> ORGANISM: Artificial Sequence
<220> FEATURE:
<223> OTHER INFORMATION: Vx4humL02

<400> SEQUENCE: 44

Asp Val Val Met Thr Gln Ser Pro Leu Ser Leu Pro Val Thr Leu Gly
1               5                   10                  15

Gln Pro Ala Ser Ile Ser Cys Arg Ser Arg Gln Ser Ile Val His Thr
            20                  25                  30

Asn Gly Asn Thr Tyr Leu Gly Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 45
<211> LENGTH: 112
<212> TYPE: PRT
<213> ORGANISM: Artificial Sequence
<220> FEATURE:
<223> OTHER INFORMATION: Vx4humL03

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Arg Ser Arg Gln Ser Ile Val His Thr
            20                  25                  30

Asn Gly Asn Thr Tyr Leu Gly Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Gly
                85                  90                  95

Ser His Val Pro Tyr Thr Phe Gly Gln Gly Thr Lys Leu Glu Ile Lys
            100                 105                 110

<210> SEQ ID NO 46
<211> LENGTH: 107
<212> TYPE: PRT
<213> ORGANISM: Artificial Sequence
<220> FEATURE:
<223> OTHER INFORMATION: Vx8murL03

<400> SEQUENCE: 46

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
```

```
                35                  40                  45
Tyr Tyr Thr Ser Arg Leu Tyr Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                 85                  90                  95

Thr Phe Gly Gly Gly Thr Lys Leu Glu Ile Lys
                100                 105
```

<210> SEQ ID NO 47
<211> LENGTH: 107
<212> TYPE: PRT
<213> ORGANISM: Artificial Sequence
<220> FEATURE:
<223> OTHER INFORMATION: Vx8humL04

<400> SEQUENCE: 47

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
             35                  40                  45

Tyr Tyr Thr Ser Arg Leu Tyr Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Trp
                 85                  90                  95

Thr Phe Gly Gln Gly Thr Lys Val Glu Ile Lys
                100                 105
```

<210> SEQ ID NO 48
<211> LENGTH: 107
<212> TYPE: PRT
<213> ORGANISM: Artificial Sequence
<220> FEATURE:
<223> OTHER INFORMATION: Vx8humL05

<400> SEQUENCE: 48

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
                20                  25                  30

Leu Asn Trp Tyr Gln Gln Lys Pro Gly Lys Ala Pro Lys Leu Leu Ile
             35                  40                  45

Tyr Tyr Thr Ser Arg Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Val Glu Ile Lys
                100                 105
```

<210> SEQ ID NO 49
<211> LENGTH: 107

```
<212> TYPE: PRT
<213> ORGANISM: Artificial Sequence
<220> FEATURE:
<223> OTHER INFORMATION: Vx8humL06

<400> SEQUENCE: 49

Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Asp Ile Ser Asn Tyr
            20                  25                  30

Leu Asn Trp Tyr Leu Gln Lys Pro Gly Gln Ser Pro Arg Leu Leu Ile
        35                  40                  45

Tyr Tyr Thr Ser Arg Leu Tyr Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Asp Asp Val Gly Ile Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 50
<211> LENGTH: 112
<212> TYPE: PRT
<213> ORGANISM: Artificial Sequence
<220> FEATURE:
<223> OTHER INFORMATION: Vx9murL04

<400> SEQUENCE: 50

Asp Val Phe Met Thr Gln Thr Pro Leu Ser Leu Pro Val Ser Leu Gly
1               5                   10                  15

Asp Gln Ala Ser Ile Ser Cys Arg Ser Ser Gln Asn Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Phe His Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Val Glu Ile Lys
            100                 105                 110

<210> SEQ ID NO 51
<211> LENGTH: 112
<212> TYPE: PRT
<213> ORGANISM: Artificial Sequence
<220> FEATURE:
<223> OTHER INFORMATION: Vx9humL07

<400> SEQUENCE: 51

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val Gln Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Phe His Arg Phe Ser Gly Val Pro
```

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                     85                  90                  95

Ser His Val Pro Tyr Thr Phe Gly Gln Gly Thr Lys Leu Glu Ile Lys
                    100                 105                 110

<210> SEQ ID NO 52
<211> LENGTH: 112
<212> TYPE: PRT
<213> ORGANISM: Artificial Sequence
<220> FEATURE:
<223> OTHER INFORMATION: Vx9humL08

<400> SEQUENCE: 52

Asp Ile Val Met Thr Gln Ser Pro Asp Ser Leu Ala Val Ser Leu Gly
  1               5                  10                  15

Glu Arg Ala Thr Ile Asn Cys Arg Ser Ser Gln Asn Ile Val Gln Ser
                 20                  25                  30

Asn Gly Asn Thr Tyr Leu Glu Trp Tyr Gln Gln Lys Pro Gly Gln Pro
             35                  40                  45

Pro Lys Leu Leu Ile Tyr Lys Val Phe His Arg Phe Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Phe Gln Gly
                     85                  90                  95

Ser His Val Pro Tyr Thr Phe Gly Gln Gly Thr Lys Leu Glu Ile Lys
                    100                 105                 110

<210> SEQ ID NO 53
<211> LENGTH: 330
<212> TYPE: PRT
<213> ORGANISM: Homo sapiens

<400> SEQUENCE: 53

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 330
<212> TYPE: PRT
<213> ORGANISM: Artificial sequence
<220> FEATURE:
<223> OTHER INFORMATION: Human Fc IgG1-N297Q

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Gln Ser Thr Tyr Arg Val Val Ser Val Leu Thr Val Leu
            180                 185                 190
```

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 55
<211> LENGTH: 326
<212> TYPE: PRT
<213> ORGANISM: Homo sapiens

<400> SEQUENCE: 55

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
```

```
            225                 230                 235                 240

Gln Val Ser Leu Thr Cys Leu Val Lys Gly Phe Tyr Pro Ser Asp Ile
                    245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
    305                 310                 315                 320

Ser Leu Ser Pro Gly Lys
                    325

<210> SEQ ID NO 56
<211> LENGTH: 377
<212> TYPE: PRT
<213> ORGANISM: Homo sapiens

<400> SEQUENCE: 56

Ala Ser Thr Lys Gly Pro Ser Val Phe Pro Leu Ala Pro Cys Ser Arg
    1               5                   10                  15

Ser Thr Ser Gly Gly Thr Ala Ala Leu Gly Cys Leu Val Lys Asp Tyr
                    20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
    65                  70                  75                  80

Tyr Thr Cys Asn Val Asn His Lys Pro Ser Asn Thr Lys Val Asp Lys
                    85                  90                  95

Arg Val Glu Leu Lys Thr Pro Leu Gly Asp Thr Thr His Thr Cys Pro
                    100                 105                 110

Arg Cys Pro Glu Pro Lys Ser Cys Asp Thr Pro Pro Cys Pro Arg
                115                 120                 125

Cys Pro Glu Pro Lys Ser Cys Asp Thr Pro Pro Cys Pro Arg Cys
        130                 135                 140

Pro Glu Pro Lys Ser Cys Asp Thr Pro Pro Cys Pro Arg Cys Pro
    145                 150                 155                 160

Ala Pro Glu Leu Leu Gly Gly Pro Ser Val Phe Leu Phe Pro Pro Lys
                    165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
    225                 230                 235                 240

Gln Asp Trp Leu Asn Gly Lys Glu Tyr Lys Cys Lys Val Ser Asn Lys
                    245                 250                 255

Ala Leu Pro Ala Pro Ile Glu Lys Thr Ile Ser Lys Thr Lys Gly Gln
                260                 265                 270
```

```
Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 57
<211> LENGTH: 326
<212> TYPE: PRT
<213> ORGANISM: Homo sapiens

<400> SEQUENCE: 57

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270
```

```
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 58
<211> LENGTH: 326
<212> TYPE: PRT
<213> ORGANISM: Artificial Sequence
<220> FEATURE:
<223> OTHER INFORMATION: Human Fc-IgG4 S228P

<400> SEQUENCE: 58

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300
```

```
Cys Ser Val Met His Glu Ala Leu His Asn His Tyr Thr Gln Lys Ser
305                 310                 315                 320

Leu Ser Leu Ser Leu Gly
                325

<210> SEQ ID NO 59
<211> LENGTH: 326
<212> TYPE: PRT
<213> ORGANISM: Artificial Sequence
<220> FEATURE:
<223> OTHER INFORMATION: Human Fc-IgG4 PE

<400> SEQUENCE: 59

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325
```

<210> SEQ ID NO 60
<211> LENGTH: 107
<212> TYPE: PRT
<213> ORGANISM: Homo sapiens

<400> SEQUENCE: 60

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 61
<211> LENGTH: 329
<212> TYPE: PRT
<213> ORGANISM: Rattus rattus

<400> SEQUENCE: 61

Ala Arg Thr Thr Ala Pro Ser Val Tyr Pro Leu Val Pro Gly Cys Ser
1               5                   10                  15

Gly Thr Ser Gly Ser Leu Val Thr Leu Gly Cys Leu Val Lys Gly Tyr
            20                  25                  30

Phe Pro Glu Pro Val Thr Val Lys Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Ser Ser Ser Val Thr Val Pro Ser Ser Thr Trp Ser Ser Gln Thr Val
65                  70                  75                  80

Thr Cys Ser Val Ala His Pro Ala Thr Lys Ser Asn Leu Ile Lys Arg
                85                  90                  95

Ile Glu Pro Arg Arg Pro Lys Pro Arg Pro Pro Thr Asp Ile Cys Ser
            100                 105                 110

Cys Asp Asp Asn Leu Gly Arg Pro Ser Val Phe Ile Phe Pro Pro Lys
        115                 120                 125

Pro Lys Asp Ile Leu Met Ile Thr Leu Thr Pro Lys Val Thr Cys Val
    130                 135                 140

Val Val Asp Val Ser Glu Glu Pro Asp Val Gln Phe Ser Trp Phe
145                 150                 155                 160

Val Asp Asn Val Arg Val Phe Thr Ala Gln Thr Gln Pro His Glu Glu
                165                 170                 175

Gln Leu Asn Gly Thr Phe Arg Val Val Ser Thr Leu His Ile Gln His
            180                 185                 190

Gln Asp Trp Met Ser Gly Lys Glu Phe Lys Cys Lys Val Asn Asn Lys
        195                 200                 205

Asp Leu Pro Ser Pro Ile Glu Lys Thr Ile Ser Lys Pro Arg Gly Lys
    210                 215                 220

```
Ala Arg Thr Pro Gln Val Tyr Thr Ile Pro Pro Arg Glu Gln Met
225                 230                 235                 240

Ser Lys Asn Lys Val Ser Leu Thr Cys Met Val Thr Ser Phe Tyr Pro
                245                 250                 255

Ala Ser Ile Ser Val Glu Trp Glu Arg Asn Gly Glu Leu Glu Gln Asp
            260                 265                 270

Tyr Lys Asn Thr Leu Pro Val Leu Asp Ser Asp Glu Ser Tyr Phe Leu
        275                 280                 285

Tyr Ser Lys Leu Ser Val Asp Thr Asp Ser Trp Met Arg Gly Asp Ile
290                 295                 300

Tyr Thr Cys Ser Val Val His Glu Ala Leu His Asn His His Thr Gln
305                 310                 315                 320

Lys Asn Leu Ser Arg Ser Pro Gly Lys
                325

<210> SEQ ID NO 62
<211> LENGTH: 107
<212> TYPE: PRT
<213> ORGANISM: Rattus rattus

<400> SEQUENCE: 62

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 63
<211> LENGTH: 323
<212> TYPE: PRT
<213> ORGANISM: Oryctolagus cuniculus

<400> SEQUENCE: 63

Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
            20                  25                  30

Leu Pro Glu Pro Val Thr Val Thr Trp Asn Ser Gly Thr Leu Thr Asn
        35                  40                  45

Gly Val Arg Thr Phe Pro Ser Val Arg Gln Ser Ser Gly Leu Tyr Ser
    50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110
```

```
Gly Pro Ser Val Phe Ile Phe Pro Lys Pro Lys Asp Thr Leu Met
            115                 120                 125

Ile Ser Arg Thr Pro Glu Val Thr Cys Val Val Asp Val Ser Gln
130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Ala His Gln Asp Trp Leu Arg Gly
                180                 185                 190

Lys Glu Phe Lys Cys Lys Val His Asn Lys Ala Leu Pro Ala Pro Ile
            195                 200                 205

Glu Lys Thr Ile Ser Lys Ala Arg Gly Gln Pro Leu Glu Pro Lys Val
210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
            260                 265                 270

Val Leu Asp Ser Asp Gly Ser Tyr Phe Leu Tyr Ser Lys Leu Ser Val
            275                 280                 285

Pro Thr Ser Glu Trp Gln Arg Gly Asp Val Phe Thr Cys Ser Val Met
290                 295                 300

His Glu Ala Leu His Asn His Tyr Thr Gln Lys Ser Ile Ser Arg Ser
305                 310                 315                 320

Pro Gly Lys

<210> SEQ ID NO 64
<211> LENGTH: 104
<212> TYPE: PRT
<213> ORGANISM: Oryctolagus cuniculus

<400> SEQUENCE: 64

Arg Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100

<210> SEQ ID NO 65
<211> LENGTH: 293
<212> TYPE: PRT
<213> ORGANISM: Homo sapiens

<400> SEQUENCE: 65
```

Met Trp Pro Leu Val Ala Ala Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
                35                  40                  45

Gln Asn Thr Thr Glu Val Tyr Val Lys Trp Lys Phe Lys Gly Arg Asp
50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
            85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
            130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
                180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
            210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
            275                 280                 285

Met Lys Phe Val Glu
        290

<210> SEQ ID NO 66
<211> LENGTH: 219
<212> TYPE: PRT
<213> ORGANISM: Artificial Sequence
<220> FEATURE:
<223> OTHER INFORMATION: Vx4murL01 Full length

<400> SEQUENCE: 66

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
            20                  25                  30

Asn Gly Asn Thr Tyr Leu Gly Trp Phe Leu Gln Lys Pro Gly Gln Ser
            35                  40                  45

Pro Lys Leu Leu Ile Tyr Lys Val Ser Asn Arg Phe Ser Gly Val Pro
50                  55                  60

```
Asp Arg Phe Ser Gly Ser Gly Ser Gly Thr Asp Phe Thr Leu Thr Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 67
<211> LENGTH: 219
<212> TYPE: PRT
<213> ORGANISM: Artificial Sequence
<220> FEATURE:
<223> OTHER INFORMATION: Vx4murL01 Full length

<400> SEQUENCE: 67

```
Asp Val Leu Met Thr Gln Thr Pro Leu Ser Leu Pro Val Asn Leu Gly
 1               5                  10                  15

Asp Gln Ala Ser Ile Ser Cys Arg Ser Arg Gln Ser Ile Val His Thr
             20                  25                  30

Asn Gly Asn Thr Tyr Leu Gly Trp Phe Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Leu Gly Val Tyr Tyr Cys Phe Gln Gly
                 85                  90                  95

Ser His Val Pro Tyr Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 68
<211> LENGTH: 219
<212> TYPE: PRT
<213> ORGANISM: Artificial Sequence
<220> FEATURE:
<223> OTHER INFORMATION: Vx4humL01 Full length LC

<400> SEQUENCE: 68

```
Asp Ile Val Met Thr Gln Ser Pro Leu Ser Leu Pro Val Thr Pro Gly
1               5                   10                  15

Glu Pro Ala Ser Ile Ser Cys Arg Ser Arg Gln Ser Ile Val His Thr
            20                  25                  30

Asn Gly Asn Thr Tyr Leu Gly Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Ile Tyr Tyr Cys Phe Gln Gly
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 69
<211> LENGTH: 214
<212> TYPE: PRT
<213> ORGANISM: Artificial Sequence
<220> FEATURE:
<223> OTHER INFORMATION: Vx8humL03 Full length LC

<400> SEQUENCE: 69

```
Asp Ile Val Met Thr Gln Ser Pro Leu Ser Leu Pro Val Thr Pro Gly
1               5                   10                  15

Glu Pro Ala Ser Ile Ser Cys Arg Ala Ser Gln Asp Ile Ser Asn Tyr
            20                  25                  30

Leu Asn Trp Tyr Leu Gln Lys Pro Gly Gln Ser Pro Arg Leu Leu Ile
        35                  40                  45

Tyr Tyr Thr Ser Arg Leu Tyr Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80
```

```
Asp Asp Val Gly Ile Tyr Tyr Cys Gln Gln Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 70
<211> LENGTH: 219
<212> TYPE: PRT
<213> ORGANISM: Artificial Sequence
<220> FEATURE:
<223> OTHER INFORMATION: Vx9humL02 Full length LC

<400> SEQUENCE: 70

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Asn Ile Val Gln Ser
            20                  25                  30

Asn Gly Asn Thr Tyr Leu Glu Trp Tyr Gln Gln Lys Pro Gly Gln Pro
        35                  40                  45

Pro Lys Leu Leu Ile Tyr Lys Val Phe His Arg Phe Ser Gly Val Pro
50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Gly
                85                  90                  95

Ser His Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 71
<211> LENGTH: 214
<212> TYPE: PRT
<213> ORGANISM: Artificial Sequence
<220> FEATURE:
<223> OTHER INFORMATION: Vx8humL02 Full length LC

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 219
<212> TYPE: PRT
<213> ORGANISM: Artificial Sequence
<220> FEATURE:
<223> OTHER INFORMATION: Vx4humL02 Full length LC

<400> SEQUENCE: 72

Asp Val Val Met Thr Gln Ser Pro Leu Ser Leu Pro Val Thr Leu Gly
1               5                   10                  15

Gln Pro Ala Ser Ile Ser Cys Arg Ser Arg Gln Ser Ile Val His Thr
            20                  25                  30

Asn Gly Asn Thr Tyr Leu Gly Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly

```
                    85                  90                  95
Ser His Val Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215
```

<210> SEQ ID NO 73
<211> LENGTH: 219
<212> TYPE: PRT
<213> ORGANISM: Artificial Sequence
<220> FEATURE:
<223> OTHER INFORMATION: Vx9humL07 Full length LC

<400> SEQUENCE: 73

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Ile Val Gln Ser
                20                  25                  30

Asn Gly Asn Thr Tyr Leu Glu Trp Phe Gln Gln Arg Pro Gly Gln Ser
            35                  40                  45

Pro Arg Arg Leu Ile Tyr Lys Val Phe His Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215
```

```
<210> SEQ ID NO 74
<211> LENGTH: 214
<212> TYPE: PRT
<213> ORGANISM: Artificial Sequence
<220> FEATURE:
<223> OTHER INFORMATION: Vx8humL01 Full length LC

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Tyr Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 75
<211> LENGTH: 219
<212> TYPE: PRT
<213> ORGANISM: Artificial Sequence
<220> FEATURE:
<223> OTHER INFORMATION: Vx9mur_L04 Full length LC

<400> SEQUENCE: 75

Asp Val Phe Met Thr Gln Thr Pro Leu Ser Leu Pro Val Ser Leu Gly
1               5                   10                  15

Asp Gln Ala Ser Ile Ser Cys Arg Ser Ser Gln Asn Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Phe His Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95
```

```
Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 76
<211> LENGTH: 444
<212> TYPE: PRT
<213> ORGANISM: Artificial Sequence
<220> FEATURE:
<223> OTHER INFORMATION: Vx4murH01 Full length HC

<400> SEQUENCE: 76

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
            435                 440

<210> SEQ ID NO 77
<211> LENGTH: 444
<212> TYPE: PRT
<213> ORGANISM: Artificial Sequence
<220> FEATURE:
<223> OTHER INFORMATION: Vx4humH01 Full length HC

<400> SEQUENCE: 77

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
            20                  25                  30

Val Ile His Tr

-continued

```
Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 78
<211> LENGTH: 444
<212> TYPE: PRT
<213> ORGANISM: Artificial Sequence
<220> FEATURE:
<223> OTHER INFORMATION: Vx8humH11 Full length HC

<400> SEQUENCE: 78

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Ser Phe Thr Asn Tyr
            20                  25                  30

Tyr Ile His Trp Leu Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Met Thr Ser Asp Thr Ser Ile Ser Thr Ala Tyr
65                  70                  75                  80
```

```
Met Glu Leu Ser Ser Leu Arg Ser Asp Asp Thr Ala Val Tyr Tyr Cys
                85                  90                  95

Ala Arg Gly Gly Lys Arg Ala Met Asp Tyr Trp Gly Gln Ala Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 79
<211> LENGTH: 443
<212> TYPE: PRT
<213> ORGANISM: Artificial Sequence
<220> FEATURE:
<223> OTHER INFORMATION: Vx9humH12 Full length HC

<400> SEQUENCE: 79
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
            35                  40                  45

Gly Tyr Thr Asp Pro Arg Thr Asp Tyr Thr Glu Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
```

```
            420             425             430
Thr Gln Lys Ser Leu Ser Leu Ser Pro Gly Lys
        435             440

<210> SEQ ID NO 80
<211> LENGTH: 443
<212> TYPE: PRT
<213> ORGANISM: Artificial Sequence
<220> FEATURE:
<223> OTHER INFORMATION: Vx9humH14 Full length HC

<400> SEQUENCE: 80

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn Tyr
            20                  25                  30

Trp Ile His Trp Val Arg Gln Met Pro Gly Lys Gly Leu Glu Trp Met
        35                  40                  45

Gly Tyr Thr Asp Pro Arg Thr Asp Tyr Thr Glu Tyr Asn Gln Lys Phe
    50                  55                  60

Lys Asp Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
```

```
                   340                 345                 350
Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 81
<211> LENGTH: 443
<212> TYPE: PRT
<213> ORGANISM: Artificial Sequence
<220> FEATURE:
<223> OTHER INFORMATION: Vx9humH15 Full length HC

<400> SEQUENCE: 81

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Tyr Thr Asp Pro Arg Thr Asp Tyr Thr Glu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Val Gly Leu Gly Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
```

```
                    260                 265                 270
Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
            290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
                435                 440

<210> SEQ ID NO 82
<211> LENGTH: 444
<212> TYPE: PRT
<213> ORGANISM: Artificial Sequence
<220> FEATURE:
<223> OTHER INFORMATION: Vx4humH02 Full length HC

<400> SEQUENCE: 82

Gln Val Gln Leu Val Gln Ser Gly Ala Glu Val Lys Lys Pro Gly Ala
1               5                   10                  15

Ser Val Gln Val Ser Cys Lys Ala Ser Gly Tyr Thr Phe Thr Asn Tyr
            20                  25

```
            180                 185                 190
Leu Gly Thr Lys Thr Tyr Thr Cys Asn Val Asp His Lys Pro Ser Asn
            195                 200                 205

Thr Lys Val Asp Lys Arg Val Glu Ser Lys Tyr Gly Pro Pro Cys Pro
            210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
            325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 83
<211> LENGTH: 443
<212> TYPE: PRT
<213> ORGANISM: Artificial Sequence
<220> FEATURE:
<223> OTHER INFORMATION: Vx9humH13 Full length HC

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Tyr Thr Asp Pro Arg Thr Asp Tyr Thr Glu Tyr Asn Gln Lys Phe
    50                  55                  60

Lys Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Val Gly Leu Gly Tyr Trp Gly Gln Gly Thr Leu
```

```
            100                 105                 110
Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 84
<211> LENGTH: 444
<212> TYPE: PRT
<213> ORGANISM: Artificial Sequence
<220> FEATURE:
<223> OTHER INFORMATION: Vx8humH10 Full length HC

<400> SEQUENCE: 84

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
```

```
                 20                  25                  30
Tyr Ile His Trp Val Arg Gln Met Pro Gly Lys Gly Leu Glu Trp Met
             35                  40                  45
Gly Tyr Ile Asp Pro Leu Asn Gly Asp Thr Thr Tyr Ser Pro Ser Phe
 50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Gly Gly Lys Arg Ala Met Asp Tyr Trp Gly Arg Gly Thr Leu
                100                 105                 110
Val Thr Val Ser Ser Ala Ser Thr Lys Gly Pro Ser Val Phe Pro Leu
                115                 120                 125
Ala Pro Cys Ser Arg Ser Thr Ser Glu Ser Thr Ala Ala Leu Gly Cys
                130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
                180                 185                 190
Leu Gly Thr Lys Thr Tyr Thr Cys Asn Val Asp His Lys Pro Ser Asn
                195                 200                 205
Thr Lys Val Asp Lys Arg Val Glu Ser Lys Tyr Gly Pro Pro Cys Pro
210                 215                 220
Pro Cys Pro Ala Pro Glu Phe Glu Gly Gly Pro Ser Val Phe Leu Phe
225                 230                 235                 240
Pro Pro Lys Pro Lys Asp Thr Leu Met Ile Ser Arg Thr Pro Glu Val
                245                 250                 255
Thr Cys Val Val Val Asp Val Ser Gln Glu Asp Pro Glu Val Gln Phe
                260                 265                 270
Asn Trp Tyr Val Asp Gly Val Glu Val His Asn Ala Lys Thr Lys Pro
                275                 280                 285
Arg Glu Glu Gln Phe Asn Ser Thr Tyr Arg Val Val Ser Val Leu Thr
                290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Glu Ser Asn Gly Gln Pro
                370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
                420                 425                 430
Tyr Thr Gln Lys Ser Leu Ser Leu Ser Leu Gly Lys
                435                 440
```

<210> SEQ ID NO 85
<211> LENGTH: 444
<212> TYPE: PRT
<213> ORGANISM: Artificial Sequence
<220> FEATURE:
<223> OTHER INFORMATION: Vx4humH04 Full length HC

<400> SEQUENCE: 85

```
Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Thr Phe Thr Asn Tyr
            20                  25                  30

Val Ile His Trp Val Arg Gln Met Pro Gly Lys Gly Leu Glu Trp Met
        35                  40                  45

Gly Tyr Ile Tyr Pro Tyr Asn Asp Gly Ile Leu Tyr Asn Glu Lys Phe
50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Tyr Tyr Val Pro Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365
```

```
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 86
<211> LENGTH: 444
<212> TYPE: PRT
<213> ORGANISM: Artificial Sequence
<220> FEATURE:
<223> OTHER INFORMATION: Vx4humH05 Full length HC

<400> SEQUENCE: 86

```
Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
        420                 425                 430

Tyr Thr Gln Lys Ser Leu Ser Leu Ser Leu Gly Lys
            435                 440
```

<210> SEQ ID NO 87
<211> LENGTH: 443
<212> TYPE: PRT
<213> ORGANISM: Artificial Sequence
<220> FEATURE:
<223> OTHER INFORMATION: Vx9humH16 Full length HC

<400> SEQUENCE: 87

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Asn T

```
Thr Lys Val Asp Lys Thr Val Glu Arg Lys Cys Cys Val Glu Cys Pro
    210                 215                 220
Pro Cys Pro Ala Pro Pro Val Ala Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Gln Phe Asn
                260                 265                 270
Trp Tyr Val Asp Gly Val Glu Val His Asn Ala Lys Thr Lys Pro Arg
            275                 280                 285
Glu Glu Gln Phe Asn Ser Thr Phe Arg Val Val Ser Val Leu Thr Val
    290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
                340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
                420                 425                 430
Thr Gln Lys Ser Leu Ser Leu Ser Pro Gly Lys
            435                 440

<210> SEQ ID NO 88
<211> LENGTH: 444
<212> TYPE: PRT
<213> ORGANISM: Artificial Sequence
<220> FEATURE:
<223> OTHER INFORMATION: Vx8humH06 Full length HC

<400> SEQUENCE: 88

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Asn Tyr
                20                  25                  30
Tyr Ile His Trp Val Arg G

```
Ala Pro Cys Ser Arg Ser Thr Ser Glu Ser Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 89
<211> LENGTH: 444
<212> TYPE: PRT
<213> ORGANISM: Artificial Sequence
<220> FEATURE:
<223> OTHER INFORMATION: Vx8humH07 Full length HC

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45
```

Gly Tyr Ile Asp Pro Leu Asn Gly Asp Thr Thr Tyr Asn Gln Lys Phe
 50                  55                  60

Lys Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 90
<211> LENGTH: 444

```
<212> TYPE: PRT
<213> ORGANISM: Artificial Sequence
<220> FEATURE:
<223> OTHER INFORMATION: Vx8humH08 Full length HC

<400> SEQUENCE: 90

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Tyr Ile His Trp Val Arg Gln Met Pro Gly Lys Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380
```

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
            405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
            435                 440

<210> SEQ ID NO 91
<211> LENGTH: 444
<212> TYPE: PRT
<213> ORGANISM: Artificial Sequence
<220> FEATURE:
<223> OTHER INFORMATION: Vx8humH09 Full length HC

<400> SEQUENCE: 91

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
                340                 345                 350

Glu Glu Met Thr Lys Asn Gln Val Ser Leu Thr Cys Leu Val Lys Gly
                355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
                420                 425                 430

Tyr Thr Gln Lys Ser Leu Ser Leu Ser Leu Gly Lys
                435                 440

<210> SEQ ID NO 92
<211> LENGTH: 444
<212> TYPE: PRT
<213> ORGANISM: Artificial Sequence
<220> FEATURE:
<223> OTHER INFORMATION: Vx8humH06 Full length HC

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
                20                  25                  30

Tyr Ile His Trp Val Arg Gln Ala Pro Gly

-continued

```
Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 93
<211> LENGTH: 444
<212> TYPE: PRT
<213> ORGANISM: Artificial Sequence
<220> FEATURE:
<223> OTHER INFORMATION: Vx8mur-H03 Full length HC

<400> SEQUENCE: 93

```
Glu Val Gln Leu Gln Gln Ser Gly Pro Glu Leu Met Lys Pro Gly Ala
1               5                   10                  15

Ser Val Lys Ile Ser Cys Lys Ala Ser Gly Tyr Ser Phe Thr Asn Tyr
            20                  25                  30

Tyr Ile His Trp Val Asn Gln

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Lys Thr Tyr Thr Cys Asn Val Asp His Lys Pro Ser Asn
195 200 205

Thr Lys Val Asp Lys Arg Val Glu Ser Lys Tyr Gly Pro Pro Cys Pro
210 215 220

Pro Cys Pro Ala Pro Glu Phe Glu Gly Gly Pro Ser Val Phe Leu Phe
225 230 235 240

Pro Pro Lys Pro Lys Asp Thr Leu Met Ile Ser Arg Thr Pro Glu Val
245 250 255

Thr Cys Val Val Val Asp Val Ser Gln Glu Asp Pro Glu Val Gln Phe
260 265 270

Asn Trp Tyr Val Asp Gly Val Glu Val His Asn Ala Lys Thr Lys Pro
275 280 285

Arg Glu Glu Gln Phe Asn Ser Thr Tyr Arg Val Val Ser Val Leu Thr
290 295 300

Val Leu His Gln Asp Trp Leu Asn Gly Lys Glu Tyr Lys Cys Lys Val
305 310 315 320

Ser Asn Lys Gly Leu Pro Ser Ser Ile Glu Lys Thr Ile Ser Lys Ala
325 330 335

Lys Gly Gln Pro Arg Glu Pro Gln Val Tyr Thr Leu Pro Pro Ser Gln
340 345 350

Glu Glu Met Thr Lys Asn Gln Val Ser Leu Thr Cys Leu Val Lys Gly
355 360 365

Phe Tyr Pro Ser Asp Ile Ala Val Glu Trp Glu Ser Asn Gly Gln Pro
370 375 380

Glu Asn Asn Tyr Lys Thr Thr Pro Pro Val Leu Asp Ser Asp Gly Ser
385 390 395 400

Phe Phe Leu Tyr Ser Arg Leu Thr Val Asp Lys Ser Arg Trp Gln Glu
405 410 415

Gly Asn Val Phe Ser Cys Ser Val Met His Glu Ala Leu His Asn His
420 425 430

Tyr Thr Gln Lys Ser Leu Ser Leu Ser Leu Gly Lys
435 440

<210> SEQ ID NO 94
<211> LENGTH: 443
<212> TYPE: PRT
<213> ORGANISM: Artificial Sequence
<220> FEATURE:
<223> OTHER INFORMATION: Vx9mur-H04 Full length HC

<400> SEQUENCE: 94

Gln Val Gln Leu Gln Gln Phe Gly Ala Glu Leu Ala Lys Pro Gly Ala
1 5 10 15

Ser Val Gln Met Ser Cys Lys Ala Ser Gly Tyr Thr Phe Thr Asn Tyr
20 25 30

Trp Ile His Trp Val Lys Gln Arg Pro Gly Gln Gly Leu Glu Trp Ile
35 40 45

Gly Tyr Thr Asp Pro Arg Thr Asp Tyr Thr Glu Tyr Asn Gln Lys Phe
50 55 60

```
Lys Asp Lys Ala Thr Leu Ala Ala Asp Arg Ser Ser Thr Ala Tyr
 65                  70                  75                  80

Met Arg Leu Ser Ser Leu Thr Ser Glu Asp Ser Ala Val Tyr Tyr Cys
                 85                  90                  95

Ala Gly Gly Gly Arg Val Gly Leu Gly Tyr Trp Gly His Gly Ser Ser
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 95
<211> LENGTH: 443
<212> TYPE: PRT
<213> ORGANISM: Artificial Sequence
<220> FEATURE:
<223> OTHER INFORMATION: Vx8humH06 Full length HC
```

<400> SEQUENCE: 95

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
```

```
                    405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 96
<211> LENGTH: 443
<212> TYPE: PRT
<213> ORGANISM: Artificial Sequence
<220> FEATURE:
<223> OTHER INFORMATION: Vx8humH07 Full length HC

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Asn Tyr
            20                  25                  30

Tyr Ile His Trp Val Arg Gln Ala Pro Gly Gln Gly Leu Glu Trp Met
        35                  40                  45

Gly Tyr Ile Asp Pro Leu Asn Gly Asp Thr Thr Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
```

325                 330                 335
Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
                435                 440

<210> SEQ ID NO 97
<211> LENGTH: 443
<212> TYPE: PRT
<213> ORGANISM: Artificial Sequence
<220> FEATURE:
<223> OTHER INFORMATION: Vx8humH08 Full length HC

<400> SEQUENCE: 97

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Tyr Ile His Trp Val Arg Gln Met Pro Gly Lys Gly Leu Glu Trp Met
            35                  40                  45

Gly Tyr Ile Asp Pro Leu Asn Gly Asp Thr Thr Tyr Asn Gln Lys Phe
        50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Lys Arg Ala Met Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
        210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr

```
                    245                 250                 255
        Cys Val Val Asp Val Ser His Glu Asp Pro Glu Val Gln Phe Asn
                        260                 265                 270

Trp Tyr Val Asp Gly Val Glu Val His Asn Ala Lys Thr Lys Pro Arg
                        275                 280                 285

Glu Glu Gln Phe Asn Ser Thr Phe Arg Val Val Ser Val Leu Thr Val
        290                 295                 300

Val His Gln Asp Trp Leu Asn Gly Lys Glu Tyr Lys Cys Lys Val Ser
        305                 310                 315                 320

Asn Lys Gly Leu Pro Ala Pro Ile Glu Lys Thr Ile Ser Lys Thr Lys
                        325                 330                 335

Gly Gln Pro Arg Glu Pro Gln Val Tyr Thr Leu Pro Pro Ser Arg Glu
                        340                 345                 350

Glu Met Thr Lys Asn Gln Val Ser Leu Thr Cys Leu Val Lys Gly Phe
                        355                 360                 365

Tyr Pro Ser Asp Ile Ala Val Glu Trp Glu Ser Asn Gly Gln Pro Glu
                        370                 375                 380

Asn Asn Tyr Lys Thr Thr Pro Pro Met Leu Asp Ser Asp Gly Ser Phe
        385                 390                 395                 400

Phe Leu Tyr Ser Lys Leu Thr Val Asp Lys Ser Arg Trp Gln Gln Gly
                        405                 410                 415

Asn Val Phe Ser Cys Ser Val Met His Glu Ala Leu His Asn His Tyr
                        420                 425                 430

Thr Gln Lys Ser Leu Ser Leu Ser Pro Gly Lys
                        435                 440

<210> SEQ ID NO 98
<211> LENGTH: 443
<212> TYPE: PRT
<213> ORGANISM: Artificial Sequence
<220> FEATURE:
<223> OTHER INFORMATION: Vx8humH09 Full length HC

<400> SEQUENCE: 98

Gln Val Gln Leu Val Gln Ser Gly Ala Glu Val Lys Lys Pro Gly Ser
        1               5                   10                  15

Ser Val Lys Val Ser Cys Lys Ala Ser Gly Tyr Ser Phe Thr Asn Tyr
                        20                  25                  30

Tyr Ile His Trp Val Arg Gln Ala Pro Gly Gln Gly Leu Gl

```
                    165                 170                 175
Ser Gly Leu Tyr Ser Leu Ser Ser Val Val Thr Val Pro Ser Ser Asn
                180                 185                 190

Phe Gly Thr Gln Thr Tyr Thr Cys Asn Val Asp His Lys Pro Ser Asn
                195                 200                 205

Thr Lys Val Asp Lys Thr Val Glu Arg Lys Cys Cys Val Glu Cys Pro
210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
                260                 265                 270

Trp Tyr Val Asp Gly Val Glu Val His Asn Ala Lys Thr Lys Pro Arg
                275                 280                 285

Glu Glu Gln Phe Asn Ser Thr Phe Arg Val Val Ser Val Leu Thr Val
290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
                340                 345                 350

Glu Met Thr Lys Asn Gln Val Ser Leu Thr Cys Leu Val Lys Gly Phe
                355                 360                 365

Tyr Pro Ser Asp Ile Ala Val Glu Trp Glu Ser Asn Gly Gln Pro Glu
                370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
                435                 440

<210> SEQ ID NO 99
<211> LENGTH: 326
<212> TYPE: PRT
<213> ORGANISM: Artificial Sequence
<220> FEATURE:
<223> OTHER INFORMATION: Human Fc-IgG4 PE'

<400> SEQUENCE: 99

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
```

```
85 90 95

Arg Val Glu Ser Lys Tyr Gly Pro Pro Cys Pro Pro Cys Pro Ala Pro
100 105 110

Glu Phe Glu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly
325

<210> SEQ ID NO 100
<211> LENGTH: 214
<212> TYPE: PRT
<213> ORGANISM: Artificial Sequence
<220> FEATURE:
<223> OTHER INFORMATION: Vx8murL03 Full length LC

<400> SEQUENCE: 100

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Asn Tyr
20 25 30

Leu Asn Trp Tyr Gln Gln Lys Pro Asp Gly Thr Val Lys Leu Leu Ile
35 40 45

Tyr Tyr Thr Ser Arg Leu Tyr Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Trp
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly

```
                115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 101
<211> LENGTH: 219
<212> TYPE: PRT
<213> ORGANISM: Artificial Sequence
<220> FEATURE:
<223> OTHER INFORMATION: Vx4mur-ratL01 Full length

<400> SEQUENCE: 101

Asp Val Leu Met Thr Gln Thr Pro Leu Ser Leu Pro Val Asn Leu Gly
1               5                   10                  15
Asp Gln Ala Ser Ile Ser Cys Arg Ser Arg Gln Ser Ile Val His Thr
            20                  25                  30
Asn Gly As

<400> SEQUENCE: 102

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Arg Pro Gly Gln Gly Leu Glu Trp Ile
        35                  40                  45

Gly Tyr Ile Tyr Pro Tyr Asn Asp Gly Ile Leu Tyr Asn Glu Lys Phe
    50                  55                  60

Lys Gly Lys Ala Thr Val Thr Ser Asp Lys Ser Ser Thr Ala Tyr
65                  70                  75                  80

Met Asp Leu Ser Ser Leu Thr Ser Glu Asp Ser Ala Val Tyr Tyr Cys
                85                  90                  95

Thr Arg Gly Gly Tyr Tyr Val Pro Asp Tyr Trp Gln Gly Thr Thr
                100                 105                 110

Leu Thr Val Ser Ser Ala Arg Thr Thr Ala Pro Ser Val Tyr Pro Leu
            115                 120                 125

Val Pro Gly Cys Ser Gly Thr Ser Gly Ser Leu Val Thr Leu Gly Cys
130                 135                 140

Leu Val Lys Gly Tyr Phe Pro Glu Pro Val Thr Val Lys Trp Asn Ser
145                 150                 155                 160

Gly Ala Leu Ser Ser Gly Val His Thr Phe Pro Ala Val Leu Gln Ser
                165                 170                 175

Gly Leu Tyr Thr Leu Ser Ser Ser Val Thr Val Pro Ser Ser Thr Trp
            180                 185                 190

Ser Ser Gln Thr Val Thr Cys Ser Val Ala His Pro Ala Thr Lys Ser
                195                 200                 205

Asn Leu Ile Lys Arg Ile Glu Pro Arg Arg Pro Lys Pro Arg Pro Pro
210                 215                 220

Thr Asp Ile Cys Ser Cys Asp Asp Asn Leu Gly Arg Pro Ser Val Phe
225                 230                 235                 240

Ile Phe Pro Pro Lys Pro Lys Asp Ile Leu Met Ile Thr Leu Thr Pro
                245                 250                 255

Lys Val Thr Cys Val Val Val Asp Val Ser Glu Glu Pro Asp Val
                260                 265                 270

Gln Phe Ser Trp Phe Val Asp Asn Val Arg Val Phe Thr Ala Gln Thr
                275                 280                 285

Gln Pro His Glu Glu Gln Leu Asn Gly Thr Phe Arg Val Val Ser Thr
            290                 295                 300

Leu His Ile Gln His Gln Asp Trp Met Ser Gly Lys Glu Phe Lys Cys
305                 310                 315                 320

Lys Val Asn Asn Lys Asp Leu Pro Ser Pro Ile Glu Lys Thr Ile Ser
                325                 330                 335

Lys Pro Arg Gly Lys Ala Arg Thr Pro Gln Val Tyr Thr Ile Pro Pro
                340                 345                 350

Pro Arg Glu Gln Met Ser Lys Asn Lys Val Ser Leu Thr Cys Met Val
            355                 360                 365

Thr Ser Phe Tyr Pro Ala Ser Ile Ser Val Glu Trp Glu Arg Asn Gly
            370                 375                 380

Glu Leu Glu Gln Asp Tyr Lys Asn Thr Leu Pro Val Leu Asp Ser Asp
385                 390                 395                 400

Glu Ser Tyr Phe Leu Tyr Ser Lys Leu Ser Val Asp Thr Asp Ser Trp
```

```
                       405                 410                 415
Met Arg Gly Asp Ile Tyr Thr Cys Ser Val Val His Glu Ala Leu His
                420                 425                 430
Asn His His Thr Gln Lys Asn Leu Ser Arg Ser Pro Gly Lys
            435                 440                 445

<210> SEQ ID NO 103
<211> LENGTH: 216
<212> TYPE: PRT
<213> ORGANISM: Artificial Sequence
<220> FEATURE:
<223> OTHER INFORMATION: Vx4mur-rabL01 Full length

<400> SEQUENCE: 103

Asp Val Leu Met Thr Gln Thr Pro Leu Ser Leu Pro Val Asn Leu Gly
1               5                   10                  15

Asp Gln Ala Ser Ile Ser Cys Arg Ser Arg Gln Ser Ile Val His Thr
            20                  25                  30

Asn Gly Asn Thr Tyr Leu Gly Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 104
<211> LENGTH: 440
<212> TYPE: PRT
<213> ORGANISM: Artificial Sequence
<220> FEATURE:
<223> OTHER INFORMATION: Vx4mur-rabH01 Full length

<400> SEQUENCE: 104

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Arg Arg Pro Gly Gln Gly Leu Glu Trp Ile
        35                  40                  45
```

-continued

```
Gly Tyr Ile Tyr Pro Tyr Asn Asp Gly Ile Leu Tyr Asn Glu Lys Phe
        50                  55                  60

Lys Gly Lys Ala Thr Val Thr Ser Asp Lys Ser Ser Ser Thr Ala Tyr
 65                  70                  75                  80

Met Asp Leu Ser Ser Leu Thr Ser Glu Asp Ser Ala Val Tyr Tyr Cys
                 85                  90                  95

Thr Arg Gly Gly Tyr Tyr Val Pro Asp Tyr Trp Gly Gln Gly Thr Thr
            100                 105                 110

Leu Thr Val Ser Ser Gly Gln Pro Lys Ala Pro Ser Val Phe Pro Leu
        115                 120                 125

Ala Pro Cys Cys Gly Asp Thr Pro Ser Ser Thr Val Thr Leu Gly Cys
130                 135                 140

Leu Val Lys Gly Tyr Leu Pro Glu Pro Val Thr Val Thr Trp Asn Ser
145                 150                 155                 160

Gly Thr Leu Thr Asn Gly Val Arg Thr Phe Pro Ser Val Arg Gln Ser
                165                 170                 175

Ser Gly Leu Tyr Ser Leu Ser Ser Val Val Ser Val Thr Ser Ser Ser
            180                 185                 190

Gln Pro Val Thr Cys Asn Val Ala His Pro Ala Thr Asn Thr Lys Val
        195                 200                 205

Asp Lys Thr Val Ala Pro Ser Thr Cys Ser Lys Pro Thr Cys Pro Pro
210                 215                 220

Pro Glu Leu Leu Gly Gly Pro Ser Val Phe Ile Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Asp Asp Pro Glu Val Gln Phe Thr Trp Tyr Ile
            260                 265                 270

Asn Asn Glu Gln Val Arg Thr Ala Arg Pro Pro Leu Arg Glu Gln Gln
        275                 280                 285

Phe Asn Ser Thr Ile Arg Val Val Ser Thr Leu Pro Ile Ala His Gln
290                 295                 300

Asp Trp Leu Arg Gly Lys Glu Phe Lys Cys Lys Val His Asn Lys Ala
305                 310                 315                 320

Leu Pro Ala Pro Ile Glu Lys Thr Ile Ser Lys Ala Arg Gly Gln Pro
                325                 330                 335

Leu Glu Pro Lys Val Tyr Thr Met Gly Pro Pro Arg Glu Glu Leu Ser
            340                 345                 350

Ser Arg Ser Val Ser Leu Thr Cys Met Ile Asn Gly Phe Tyr Pro Ser
        355                 360                 365

Asp Ile Ser Val Glu Trp Glu Lys Asn Gly Lys Ala Glu Asp Asn Tyr
370                 375                 380

Lys Thr Thr Pro Ala Val Leu Asp Ser Asp Gly Ser Tyr Phe Leu Tyr
385                 390                 395                 400

Ser Lys Leu Ser Val Pro Thr Ser Glu Trp Gln Arg Gly Asp Val Phe
                405                 410                 415

Thr Cys Ser Val Met His Glu Ala Leu His Asn His Tyr Thr Gln Lys
            420                 425                 430

Ser Ile Ser Arg Ser Pro Gly Lys
        435                 440
```

THERAPEUTIC CD47 ANTIBODIES

CROSS-REFERENCE TO RELATED APPLICATIONS

This application is a continuation of International Application No. PCT/US2016/052383, filed Sep. 17, 2016, which claims the benefit of United States Provisional Application Nos. 62/220,691, filed Sep. 18, 2015; 62/263,544, filed Dec. 4, 2015; 62/221,852, filed Sep. 22, 2015; 62/220,725, filed Sep. 18, 2015; 62/232,681, filed Sep. 25, 2015; 62/252,171, filed Nov. 6, 2015; and 62/354,592, filed Jun. 24, 2016; the disclosures of which are hereby incorporated by reference as if written herein in their entireties.

FIELD OF THE DISCLOSURE

This disclosure is related generally to anti-CD47 monoclonal antibodies (anti-CD47 mAbs) with distinct functional profiles as described herein, methods to generate anti-CD47 mAbs, and to methods of using these anti-CD47 mAbs as therapeutics for the prevention and treatment of solid and hematological cancers, ischemia-reperfusion injury, cardiovascular diseases, autoimmune diseases, or inflammatory diseases or as diagnostics for determining the level of CD47 in tissue samples.

BACKGROUND OF THE DISCLOSURE

CD47 is a cell surface receptor comprised of an extracellular IgV set domain, a 5 transmembrane domain, and a cytoplasmic tail that is alternatively spliced. Two ligands bind CD47: signal inhibitory receptor protein α (SIRPα) and thrombospondin-1 (TSP1). CD47 expression and/or activity have been implicated in a number of diseases and disorders. Accordingly, there exists a need for therapeutic compositions and methods for treating diseases and conditions associated with CD47 in humans and animals, including the prevention and treatment of solid and hematological cancers, ischemia-reperfusion injury (IRI), cardiovascular diseases, or an autoimmune or inflammatory disease. There also exists a need for diagnostic compositions and methods for determining the level of CD47 expression in tumor samples.

SUMMARY OF THE DISCLOSURE

The present disclosure describes anti-CD47 mAbs with distinct functional profiles. These antibodies possess distinct combinations of properties selected from the following: 1) exhibit cross-reactivity with one or more species homologs of CD47; 2) block the interaction between CD47 and its ligand SIRPα; 3) increase phagocytosis of human tumor cells, 4) induce death of susceptible human tumor cells; 5) do not induce cell death of human tumor cells; 6) have reduced binding to human red blood cells (hRBCs); 7) have no detectable binding to hRBCs; 8) cause reduced agglutination of hRBCs; 9) cause no detectable agglutination of hRBCs; 10) reverse TSP1 inhibition of the nitric oxide (NO) pathway and/or 11) do not reverse TSP1 inhibition of the NO pathway. The antibodies of the disclosure are useful in various therapeutic methods for treating diseases and conditions associated with CD47 in humans and animals, including the prevention and treatment of solid and hematological cancers, autoimmune diseases, inflammatory diseases, IRI, and cardiovascular diseases. The antibodies of the disclosure are also useful as diagnostics to determine the level of CD47 expression in tissue samples. Embodiments of the disclosure include isolated antibodies and immunologically active binding fragments thereof; pharmaceutical compositions comprising one or more of the anti-CD47 monoclonal antibodies, preferably chimeric or humanized forms of said antibodies; methods of therapeutic use of such anti-CD47 monoclonal antibodies; and cell lines that produce these anti-CD47 monoclonal antibodies.

The embodiments of the disclosure include the mAbs, or antigen-binding fragments thereof, which are defined by reference to specific structural characteristics i.e. specified amino acid sequences of either the CDRs or entire heavy chain or light chain variable domains. All of these antibodies bind to CD47.

The monoclonal antibodies, or antigen binding fragments thereof may comprise at least one, usually at least three, CDR sequences as provided herein, usually in combination with framework sequences from a human variable region or as an isolated CDR peptide. In some embodiments, an antibody comprises at least one light chain comprising the three light chain CDR sequences provided herein situated in a variable region framework, which may be, without limitation, a murine or human variable region framework, and at least one heavy chain comprising the three heavy chain CDR sequences provided herein situated in a variable region framework, which may be, without limitation, a human or murine variable region framework.

Preferred embodiments are anti-CD47 mAbs, or antigen binding fragments thereof, comprising a heavy chain variable domain comprising a variable heavy chain CDR1, variable heavy chain CDR2, and a variable heavy chain CDR3, wherein said variable heavy chain CDR1 comprises an amino acid sequence selected from the group consisting of:

SEQ ID NO:1, SEQ ID NO:2, SEQ ID NO:3; said variable heavy chain CDR2 comprises an amino acid sequence selected from the group consisting of: SEQ ID NO:4, SEQ ID NO:5, SEQ ID NO:6; and said variable heavy chain CDR3 comprises an amino acid sequence selected from the group consisting of: SEQ ID NO:7, SEQ ID NO:8, SEQ ID NO:9, and SEQ ID NO:10.

The heavy chain variable domain may comprise any one of the listed variable heavy chain CDR1 sequences (HCDR1) in combination with any one of the variable heavy chain CDR2 sequences (HCDR2) and any one of the variable heavy chain CDR3 sequences (HCDR3). However, certain embodiments of HCDR1 and HCDR2 and HCDR3 are particularly preferred, which derive from a single common $V_H$ domain, examples of which are described herein.

The antibody or antigen binding fragment thereof may additionally comprise a light chain variable domain ($V_L$), which is paired with the $V_H$ domain to form an antigen binding domain. Preferred light chain variable domains are those comprising a variable light chain CDR1, variable light chain CDR2, and a variable light chain CDR3, wherein said variable light chain CDR1 comprises an amino acid sequence selected from the group consisting of:

SEQ ID NO:11, SEQ ID NO:12, SEQ ID NO:13, SEQ ID NO:14; said variable light chain CDR2 optionally comprises an amino acid sequence selected from the group consisting of: SEQ ID NO:15, SEQ ID NO:16, SEQ ID NO:17; and said variable light chain CDR3 optionally comprises an amino acid sequence selected from the group consisting of: SEQ ID NO:18, SEQ ID NO:19, SEQ ID NO:20.

The light chain variable domain may comprise any one of the listed variable light chain CDR1 sequences (LCDR1) in combination with any one of the variable light chain CDR2 sequences (LCDR2) and any one of the variable light chain CDR3 sequences (LCDR3). However, certain embodiments of LCDR1 and LCDR2 and LCDR3 are particularly preferred, which derive from a single common $V_L$ domain, examples of which are described herein.

Any given CD47 antibody or antigen binding fragment thereof comprising a VH domain paired with a VL domain will comprise a combination of 6 CDRs: variable heavy chain CDR1 (HCDR1), variable heavy chain CDR2 (HCDR2), variable heavy chain CDR3 (HCDR3), variable light chain CDR1 (LCDR1), variable light chain CDR2 (LCDR2), and variable light chain CDR1 (LCDR1). Although all combinations of 6 CDRs selected from the CDR sequence groups listed above are permissible, and within the scope of the disclosure, certain combinations of 6 CDRs are particularly preferred.

Preferred combinations of 6 CDRs include, but are not limited to, the combinations of variable heavy chain CDR1 (HCDR1), variable heavy chain CDR2 (HCDR2), variable heavy chain CDR3 (HCDR3), variable light chain CDR1 (LCDR1), variable light chain CDR2 (LCDR2), and variable light chain CDR3 (LCDR3) selected from the group consisting of:
  (i) HCDR1 comprising SEQ ID NO:1, HCDR2 comprising SEQ ID NO:4, HCDR3 comprising SEQ ID NO:7, LCDR1 comprising SEQ ID NO:11, LCDR2 comprising SEQ ID NO:15, LCDR3 comprising SEQ ID NO:18;
  (ii) HCDR1 comprising SEQ ID NO:1, HCDR2 comprising SEQ ID NO:4, HCDR3 comprising SEQ ID NO:8, LCDR1 comprising SEQ ID NO:11, LCDR2 comprising SEQ ID NO:15, LCDR3 comprising SEQ ID NO:18;
  (iii) HCDR1 comprising SEQ ID NO:2, HCDR2 comprising SEQ ID NO:5, HCDR3 comprising SEQ ID NO:9, LCDR1 comprising SEQ ID NO:12, LCDR2 comprising SEQ ID NO:16, LCDR3 comprising SEQ ID NO:19;
  (iv) HCDR1 comprising SEQ ID NO:2, HCDR2 comprising SEQ ID NO:5, HCDR3 comprising SEQ ID NO:9, LCDR1 comprising SEQ ID NO:13, LCDR2 comprising SEQ ID NO:16, LCDR3 comprising SEQ ID NO:19; and
  (v) HCDR1 comprising SEQ ID NO:3, HCDR2 comprising SEQ ID NO:6, HCDR3 comprising SEQ ID NO:10, LCDR1 comprising SEQ ID NO:14, LCDR2 comprising SEQ ID NO:17, LCDR3 comprising SEQ ID NO:20.

Further preferred anti-CD47 antibodies include antibodies or antigen binding fragments thereof, comprising a heavy chain variable domain having an amino acid sequence selected from the group consisting of: the amino acid sequences of SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:31, SEQ ID NO: 32, SEQ ID NO:33, SEQ ID NO:34, SEQ ID NO:35, SEQ ID NO:36, SEQ ID NO:37, SEQ ID NO:38, SEQ ID NO:39, and SEQ ID NO:40 and amino acid sequences exhibiting at least 90%, 95%, 97%, 98%, or 99% sequence identity to one of the recited sequences. Alternatively or in addition, preferred anti-CD47 antibodies including antibodies or antigen binding fragments thereof may comprise a light chain variable domain having an amino acid sequence selected from the group consisting of: the amino acid sequences of SEQ ID NO:41, SEQ ID NO:42, SEQ ID NO:43, SEQ ID NO:44, SEQ ID NO:46, SEQ ID NO:48, SEQ ID NO:49, SEQ ID NO:50, SEQ ID NO:51, and SEQ ID NO:52 and amino acid sequences exhibiting at least 90%, 95%, 97%, 98%, or 99% sequence identity to one of the recited sequences.

Although all possible pairing of $V_H$ domains and $V_L$ domains selected from the $V_H$ and VL domain sequence groups listed above are permissible, and within the scope of the disclosure, certain combinations of $V_H$ and $V_L$ domains are particularly preferred. Accordingly, preferred CD47 antibodies, or antigen binding fragments thereof, are those comprising a combination of a heavy chain variable domain ($V_H$) and a light chain variable domain ($V_L$), wherein the combination is selected from the group consisting of:
  (i) a heavy chain variable domain comprising the amino acid sequence of SEQ ID NO:21 and a light chain variable domain comprising the amino acid sequence SEQ ID NO:41;
  (ii) a heavy chain variable domain comprising the amino acid sequence of SEQ ID NO:23 and a light chain variable domain comprising the amino acid sequence SEQ ID NO:43;
  (iii) a heavy chain variable domain comprising the amino acid sequence of SEQ ID NO:34 and a light chain variable domain comprising the amino acid sequence SEQ ID NO:49;
  (iv) a heavy chain variable domain comprising the amino acid sequence of SEQ ID NO:36 and a light chain variable domain comprising the amino acid sequence SEQ ID NO:52;
  (v) a heavy chain variable domain comprising the amino acid sequence of SEQ ID NO:38 and a light chain variable domain comprising the amino acid sequence SEQ ID NO:52;
  (vi) a heavy chain variable domain comprising the amino acid sequence of SEQ ID NO:39 and a light chain variable domain comprising the amino acid sequence SEQ ID NO:52;
  (vii) a heavy chain variable domain comprising the amino acid sequence of SEQ ID NO:24 and a light chain variable domain comprising the amino acid sequence SEQ ID NO:43;
  (viii) a heavy chain variable domain comprising the amino acid sequence of SEQ ID NO:37 and a light chain variable domain comprising the amino acid sequence SEQ ID NO:52;
  (ix) a heavy chain variable domain comprising the amino acid sequence of SEQ ID NO:33 and a light chain variable domain comprising the amino acid sequence SEQ ID NO:48;
  (x) a heavy chain variable domain comprising the amino acid sequence of SEQ ID NO:26 and a light chain variable domain comprising the amino acid sequence SEQ ID NO:44;
  (xi) a heavy chain variable domain comprising the amino acid sequence of SEQ ID NO:27 and a light chain variable domain comprising the amino acid sequence SEQ ID NO:44; and
  (xii) a heavy chain variable domain comprising the amino acid sequence of SEQ ID NO:38 and a light chain variable domain comprising the amino acid sequence SEQ ID NO:51;
  (xiii) a heavy chain variable domain comprising the amino acid sequence of SEQ ID NO:39 and a light chain variable domain comprising the amino acid sequence SEQ ID NO:51;

(xiv) a heavy chain variable domain comprising the amino acid sequence of SEQ ID NO:40 and a light chain variable domain comprising the amino acid sequence SEQ ID NO:52;
(xv) a heavy chain variable domain comprising the amino acid sequence of SEQ ID NO:36 and a light chain variable domain comprising the amino acid sequence SEQ ID NO:51;
(xvi) a heavy chain variable domain comprising the amino acid sequence of SEQ ID NO:29 and a light chain variable domain comprising the amino acid sequence SEQ ID NO:47;
(xvii) a heavy chain variable domain comprising the amino acid sequence of SEQ ID NO:30 and a light chain variable domain comprising the amino acid sequence SEQ ID NO:47;
(xviii) a heavy chain variable domain comprising the amino acid sequence of SEQ ID NO:31 and a light chain variable domain comprising the amino acid sequence SEQ ID NO:47;
(xix) a heavy chain variable domain comprising the amino acid sequence of SEQ ID NO:32 and a light chain variable domain comprising the amino acid sequence SEQ ID NO:47;
(xx) a heavy chain variable domain comprising the amino acid sequence of SEQ ID NO:33 and a light chain variable domain comprising the amino acid sequence SEQ ID NO:47;
(xxi) a heavy chain variable domain comprising the amino acid sequence of SEQ ID NO:29 and a light chain variable domain comprising the amino acid sequence SEQ ID NO:48;
(xxii) a heavy chain variable domain comprising the amino acid sequence of SEQ ID NO:30 and a light chain variable domain comprising the amino acid sequence SEQ ID NO:48;
(xxiii) a heavy chain variable domain comprising the amino acid sequence of SEQ ID NO:31 and a light chain variable domain comprising the amino acid sequence SEQ ID NO:48;
(xxiv) a heavy chain variable domain comprising the amino acid sequence of SEQ ID NO:32 and a light chain variable domain comprising the amino acid sequence SEQ ID NO:48;
(xxv) a heavy chain variable domain comprising the amino acid sequence of SEQ ID NO:26 and a light chain variable domain comprising the amino acid sequence SEQ ID NO:43;
(xxvi) a heavy chain variable domain comprising the amino acid sequence of SEQ ID NO:27 and a light chain variable domain comprising the amino acid sequence SEQ ID NO:43;
(xxvii) a heavy chain variable domain comprising the amino acid sequence of SEQ ID NO:28 and a light chain variable domain comprising the amino acid sequence SEQ ID NO:46;
(xxviii) a heavy chain variable domain comprising the amino acid sequence of SEQ ID NO:35 and a light chain variable domain comprising the amino acid sequence SEQ ID NO:50;
(xxix) a heavy chain variable domain comprising the amino acid sequence of SEQ ID NO:29 and a light chain variable domain comprising the amino acid sequence SEQ ID NO:48;
(xxx) a heavy chain variable domain comprising the amino acid sequence of SEQ ID NO:30 and a light chain variable domain comprising the amino acid sequence SEQ ID NO:48;
(xxxi) a heavy chain variable domain comprising the amino acid sequence of SEQ ID NO:31 and a light chain variable domain comprising the amino acid sequence SEQ ID NO:48;
(xxxii) a heavy chain variable domain comprising the amino acid sequence of SEQ ID NO:32 and a light chain variable domain comprising the amino acid sequence SEQ ID NO:48;
(xxxiii) a heavy chain variable domain comprising the amino acid sequence of SEQ ID NO:37 and a light chain variable domain comprising the amino acid sequence SEQ ID NO:51; and
(xxxiv) a heavy chain variable domain comprising the amino acid sequence of SEQ ID NO:40 and a light chain variable domain comprising the amino acid sequence SEQ ID NO:51.

Preferred anti-CD47 antibodies or antigen binding fragments thereof may also comprise a combination of a heavy chain variable domain and a light chain variable domain wherein the heavy chain variable domain comprises a VH sequence with at least 85% sequence identity, or at least 90% sequence identity, or at least 95% sequence identity, or at least 97%, 98% or 99% sequence identity, to the heavy chain amino acid sequences shown above in (i) to (xxxiv) and/or the light chain variable domain comprises a VL sequence with at least 85% sequence identity, or at least 90% sequence identity, or at least 95% sequence identity, or at least 97%, 98% or 99% sequence identity, to the light chain amino acid sequences shown above in (i) to (xxxiv). The specific VH and VL pairings or combinations in parts (i) through (xxxiv) may be preserved for anti-CD47 antibodies having VH and VL domain sequences with a particular percentage sequence identity to these reference sequences.

For all embodiments wherein the heavy chain and/or light chain variable domains of the antibodies or antigen binding fragments are defined by a particular percentage sequence identity to a reference sequence, the VH and/or VL domains may retain identical CDR sequences to those present in the reference sequence such that the variation is present only within the framework regions.

In another embodiment, the preferred CD47 antibodies, or antigen binding fragments thereof, are those comprising a combination of a heavy chain (HC) and a light chain (LC), wherein the combination is selected from the group consisting of:
(i) a heavy chain comprising the amino acid sequence of SEQ ID NO:76 and a light chain comprising the amino acid sequence SEQ ID NO:66;
(ii) a heavy chain comprising the amino acid sequence of SEQ ID NO:77 and a light chain comprising the amino acid sequence SEQ ID NO:68;
(iii) a heavy chain comprising the amino acid sequence of SEQ ID NO:78 and a light chain comprising the amino acid sequence SEQ ID NO:69;
(iv) a heavy chain comprising the amino acid sequence of SEQ ID NO:79 and a light chain comprising the amino acid sequence SEQ ID NO:70;
(v) a heavy chain comprising the amino acid sequence of SEQ ID NO:80 and a light chain comprising the amino acid sequence SEQ ID NO:70;
(vi) a heavy chain comprising the amino acid sequence of SEQ ID NO:81 and a light chain comprising the amino acid sequence SEQ ID NO:70;

(vii) a heavy chain comprising the amino acid sequence of SEQ ID NO:82 and a light chain comprising the amino acid sequence SEQ ID NO:68;
(viii) a heavy chain comprising the amino acid sequence of SEQ ID NO:83 and a light chain comprising the amino acid sequence SEQ ID NO:70;
(ix) a heavy chain comprising the amino acid sequence of SEQ ID NO:84 and a light chain comprising the amino acid sequence SEQ ID NO:71;
(x) a heavy chain comprising the amino acid sequence of SEQ ID NO:85 and a light chain comprising the amino acid sequence SEQ ID NO:72;
(xi) a heavy chain comprising the amino acid sequence of SEQ ID NO:86 and a light chain comprising the amino acid sequence SEQ ID NO:72;
(xii) a heavy chain comprising the amino acid sequence of SEQ ID NO:80 and a light chain comprising the amino acid sequence SEQ ID NO:73;
(xiii) a heavy chain comprising the amino acid sequence of SEQ ID NO:81 and a light chain comprising the amino acid sequence SEQ ID NO:73;
(xiv) a heavy chain comprising the amino acid sequence of SEQ ID NO:87 and a light chain comprising the amino acid sequence SEQ ID NO:70;
(xv) a heavy chain comprising the amino acid sequence of SEQ ID NO:79 and a light chain comprising the amino acid sequence SEQ ID NO:73;
(xvi) a heavy chain comprising the amino acid sequence of SEQ ID NO:88 and a light chain comprising the amino acid sequence SEQ ID NO:74;
(xvii) a heavy chain comprising the amino acid sequence of SEQ ID NO:89 and a light chain comprising the amino acid sequence SEQ ID NO:74;
(xviii) a heavy chain comprising the amino acid sequence of SEQ ID NO:90 and a light chain comprising the amino acid sequence SEQ ID NO:74;
(xix) a heavy chain comprising the amino acid sequence of SEQ ID NO:91 and a light chain comprising the amino acid sequence SEQ ID NO:74;
(xx) a heavy chain comprising the amino acid sequence of SEQ ID NO:84 and a light chain comprising the amino acid sequence SEQ ID NO:74;
(xxi) a heavy chain comprising the amino acid sequence of SEQ ID NO:92 and a light chain comprising the amino acid sequence SEQ ID NO:71;
(xxii) a heavy chain comprising the amino acid sequence of SEQ ID NO:89 and a light chain comprising the amino acid sequence SEQ ID NO:71;
(xxiii) a heavy chain comprising the amino acid sequence of SEQ ID NO:90 and a light chain comprising the amino acid sequence SEQ ID NO:31;
(xxiv) a heavy chain comprising the amino acid sequence of SEQ ID NO:91 and a light chain comprising the amino acid sequence SEQ ID NO:71;
(xxv) a heavy chain comprising the amino acid sequence of SEQ ID NO:85 and a light chain comprising the amino acid sequence SEQ ID NO:68;
(xxvi) a heavy chain comprising the amino acid sequence of SEQ ID NO:86 and a light chain comprising the amino acid sequence SEQ ID NO:68;
(xxvii) a heavy chain comprising the amino acid sequence of SEQ ID NO:93 and a light chain comprising the amino acid sequence SEQ ID NO:100;
(xxviii) a heavy chain comprising the amino acid sequence of SEQ ID NO:94 and a light chain comprising the amino acid sequence SEQ ID NO:75;
(xxix) a heavy chain comprising the amino acid sequence of SEQ ID NO:95 and a light chain comprising the amino acid sequence SEQ ID NO:71;
(xxx) a heavy chain comprising the amino acid sequence of SEQ ID NO:96 and a light chain comprising the amino acid sequence SEQ ID NO:71;
(xxxi) a heavy chain comprising the amino acid sequence of SEQ ID NO:97 and a light chain comprising the amino acid sequence SEQ ID NO:71;
(xxxii) a heavy chain comprising the amino acid sequence of SEQ ID NO:98 and a light chain comprising the amino acid sequence SEQ ID NO:71;
(xxxiii) a heavy chain comprising the amino acid sequence of SEQ ID NO:83 and a light chain comprising the amino acid sequence SEQ ID NO:73;
(xxxiv) a heavy chain comprising the amino acid sequence of SEQ ID NO:87 and a light chain comprising the amino acid sequence SEQ ID NO:73;
(xxxv) a heavy chain comprising the amino acid sequence of SEQ ID NO:102 and a light chain comprising the amino acid sequence SEQ ID NO:101;
(xxxvi) a heavy chain comprising the amino acid sequence of SEQ ID NO:104 and a light chain comprising the amino acid sequence SEQ ID NO:103;
wherein the VH amino acid sequence is at least 90%, 95%, 97%, 98% or 99% identical thereto and the a VL amino acid sequence is at least 90%, 95%, 97%, 98% or 99% identical thereto.

Preferred embodiments of the anti-CD47 antibodies described herein, are also characterized by combinations of properties which are not exhibited by prior art anti-CD47 antibodies proposed for human therapeutic use. Accordingly, the preferred anti-CD47 antibodies described herein are characterized by:
  a. binds to human CD47,
  b. blocks SIRPα binding to human CD47,
  c. increases phagocytosis of human tumor cells; and
  d. induces death of susceptible human tumor cells.

In another preferred embodiment described herein, the anti-CD47 antibodies are characterized by:
  a. binds to human CD47,
  b. blocks SIRPα binding to human CD47,
  c. increases phagocytosis of human tumor cells,
  d. induces death of susceptible human tumor cells; and
  e. causes no agglutination of human red blood cells (hRBCs).

In yet another preferred embodiment described herein, the anti-CD47 antibodies are characterized by:
  a. binds to human CD47,
  b. blocks SIRPα binding to human CD47,
  c. increases phagocytosis of human tumor cells,
  d. induces death of susceptible human tumor cells; and
  e. causes reduced agglutination of human red blood cells (hRBCs).

In another preferred embodiment described herein, the anti-CD47 antibodies are characterized by:
  a. specifically binds to human CD47,
  b. blocks SIRPα binding to human CD47,
  c. increases phagocytosis of human tumor cells
  d. induces death of susceptible human tumor cells; and
  e. has reduced hRBC binding.

In another preferred embodiment described herein, the anti-CD47 antibodies are characterized by:
  a. binds to human CD47,
  b. blocks SIRPα binding to human CD47,
  c. increases phagocytosis of human tumor cells, d. causes no agglutination of human red blood cells (hRBCs); and e. does not bind to hRBCs.

In another preferred embodiment described herein, the anti-CD47 antibodies are characterized by:

a. specifically binds to human CD47, b. blocks SIRPα binding to human CD47, c. increases phagocytosis of human tumor cells, d. causes no agglutination of human red blood cells (hRBCs); and e. has reduced hRBC binding.

In another preferred embodiment described herein, the monoclonal antibody, or antigen binding fragment thereof specifically also binds to non-human primate CD47, wherein non-human primate may include, but is not limited to, cynomolgus monkey, green monkey, rhesus monkey and squirrel monkey.

In yet another preferred embodiment described herein, the monoclonal antibody, or antigen binding fragment thereof binds to human, non-human primate, mouse, rabbit, and rat CD47.

Various forms of the anti-CD47 mAbs disclosed are contemplated herein. For example, the anti-CD47 mAbs can be full length humanized antibodies with human frameworks and constant regions of the isotypes, IgA, IgD, IgE, IgG, and IgM, more particularly, IgG1, IgG2, IgG3, IgG4, and in some cases with various mutations to alter Fc receptor function or prevent Fab arm exchange or an antibody fragment, e.g., a F(ab')2 fragment, a F(ab) fragment, a single chain Fv fragment (scFv), etc., as disclosed herein.

The preferred embodiments of the disclosure provide pharmaceutical or veterinary compositions comprising one or more of the anti-CD47 mAbs or fragments disclosed herein, optionally chimeric or humanized forms, and a pharmaceutically acceptable carrier, diluent, or excipient.

Prior to the present disclosure, there was a need to identify anti-CD47 mAbs that possess the functional profiles as described herein. The anti-CD47 mAbs of the present disclosure exhibit distinct combinations of properties, particularly combinations of properties that render the mAbs particularly advantageous or suitable for use in human therapy, particularly in the prevention and/or treatment of solid and hematological cancers, ischemia-reperfusion injury, autoimmune and/or inflammatory diseases.

Further scope of the applicability of the present disclosure will become apparent from the detailed description provided below. However, it should be understood that the detailed description and specific examples, while indicating preferred embodiments of the disclosure, are given by way of illustration only since various changes and modifications within the spirit and scope of the disclosure will become apparent to those skilled in the art from this detailed description.

BRIEF DESCRIPTION OF THE FIGURES

The above and other aspects, features, and advantages of the present disclosure will be better understood from the following detailed descriptions taken in conjunction with the accompanying drawing(s), all of which are given by way of illustration only, and are not limitative of the present disclosure.

FIG. 4A. Binding of VLX8 Humanized mAbs to Human RBCs. Binding of VLX8 IgG4PE xi or humanized mAbs (VLX8hum_01 IgG4PE, VLX8hum_03 IgG4PE, VLX8hum_07 IgG4PE, and VLX8hum_10 IgG4PE) to human CD47 was determined using freshly isolated human RBCs. RBCs were incubated for 1 hr at 37° C. with various concentrations of VLX8 mAbs, washed and incubated for 1 hr with FITC-labeled donkey anti-human antibody. Cells were washed and antibody binding measured using flow cytometry.

FIG. 4B. Binding of VLX8 Humanized mAbs to Human RBCs. Binding of VLX8 IgG4PE xi or humanized mAbs (VLX8hum_06 IgG2, VLX8hum_07 IgG2, VLX8hum_08 IgG2 and VLX8hum_09 IgG2) to human CD47 was determined using freshly isolated human RBCs. RBCs were incubated for 1 hr at 37° C. with various concentrations of VLX8 mAbs, washed and incubated for 1 hr with FITC-labeled donkey anti-human antibody. Cells were washed and antibody binding measured using flow cytometry.

FIG. 5A. Binding of VLX9 Humanized mAbs to Human OV10 hCD47 Cells. Binding of VLX9 IgG2 xi or humanized mAbs (VLX9hum_01 IgG2, VLX9hum_02 IgG2, VLX9hum_03 IgG2, VLX9hum_04 IgG2 and VLX9hum_05 IgG2) to human CD47 was determined using an OV10 human CD47 cell-based ELISA. OV10 hCD47 cells were plated into 96 well plates and were confluent at the time of assay. Various concentrations of mAbs were added to the cells for 1 hr. Cells were washed and then incubated with HRP-labelled secondary antibody for 1 hr followed by addition of peroxidase substrate.

FIG. 5B. Binding of VLX9 Humanized mAbs to Human OV10 hCD47 Cells. Binding of VLX9 IgG2 xi or humanized mAbs (VLX9hum_06 IgG2, VLX9hum_07 IgG2, VLX9hum_08 IgG2, VLX9hum_09 IgG2 and VLX9hum_10 IgG2) to human CD47 was determined using a OV10 hCD47 cell-based ELISA. OV10 hCD47 cells were plated into 96 well plates and were confluent at the time of assay. Various concentrations of mAbs were added to the cells for 1 hr. Cells were washed and then incubated with HRP-labelled secondary antibody for 1 hr followed by addition of peroxidase substrate.

Figure 6:
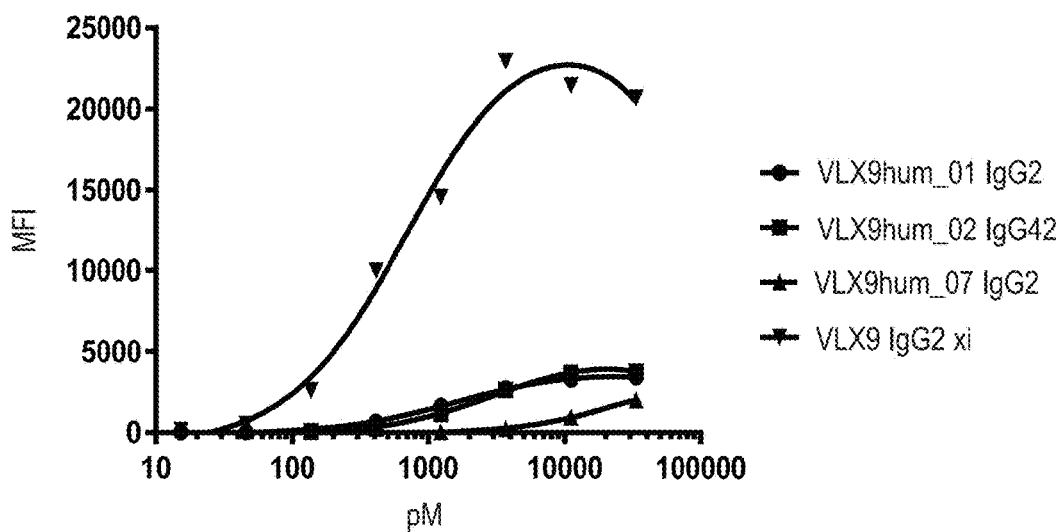

FIG. 6. Binding of VLX9 Humanized mAbs to Human RBCs. Binding of VLX9 IgG2 xi or humanized mAbs to human CD47 was determined using freshly isolated human hRBCs. RBCs were incubated for 60 minutes at 37° C. with various concentrations of VLX9 mAbs, washed and incubated for 1 hr with FITC-labeled donkey anti-human antibody. Cells were washed and antibody binding measured using flow cytometry.

Figure 7:
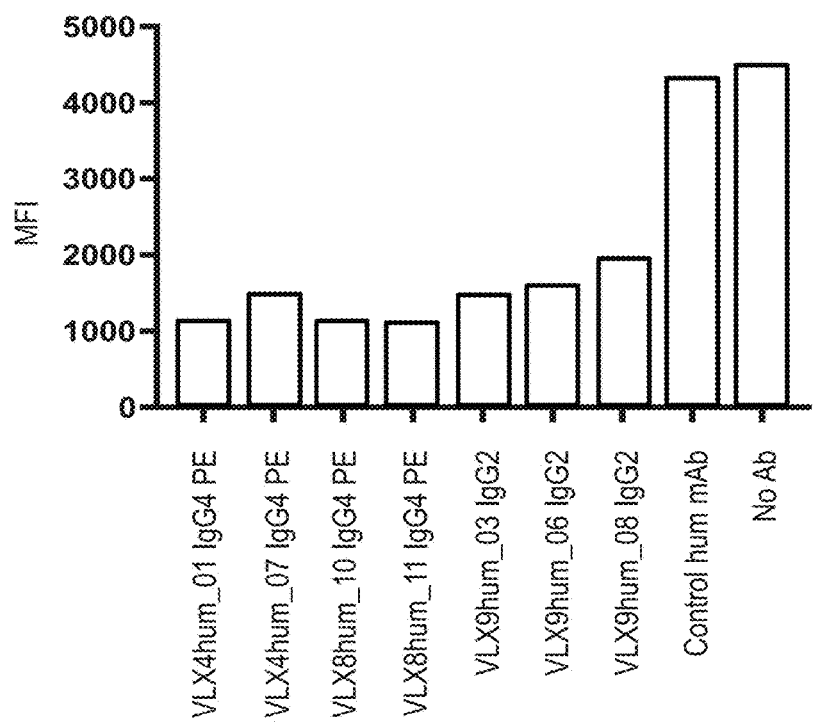

FIG. 7. VLX4, VLX8, and VLX9 Humanized mAbs Block SIRPα binding to CD47 on Jurkat Cells. $1.5 \times 10^6$ Jurkat cells were incubated with 5 µg/ml of VLX4, VLX8 and VLX9 CD47 humanized mAbs (VLX4hum_01 IgG4 PE, VLX4hum_07 IgG4 PE, VLX8hum_10 IgG4 PE, VLX4hum_11 IgG4 PE, VLX9hum_03 IgG2, VLX9hum_06 IgG2, and VLX9hum_08 IgG2) or a control antibody in RPMI containing 10% media for 30 min at 37° C. An equal volume of fluorescently labeled SIRPα-Fc fusion protein was added and incubated for an additional 30 min at 37° C. Cells were washed and binding was assessed using flow cytometry.

Figure 8:
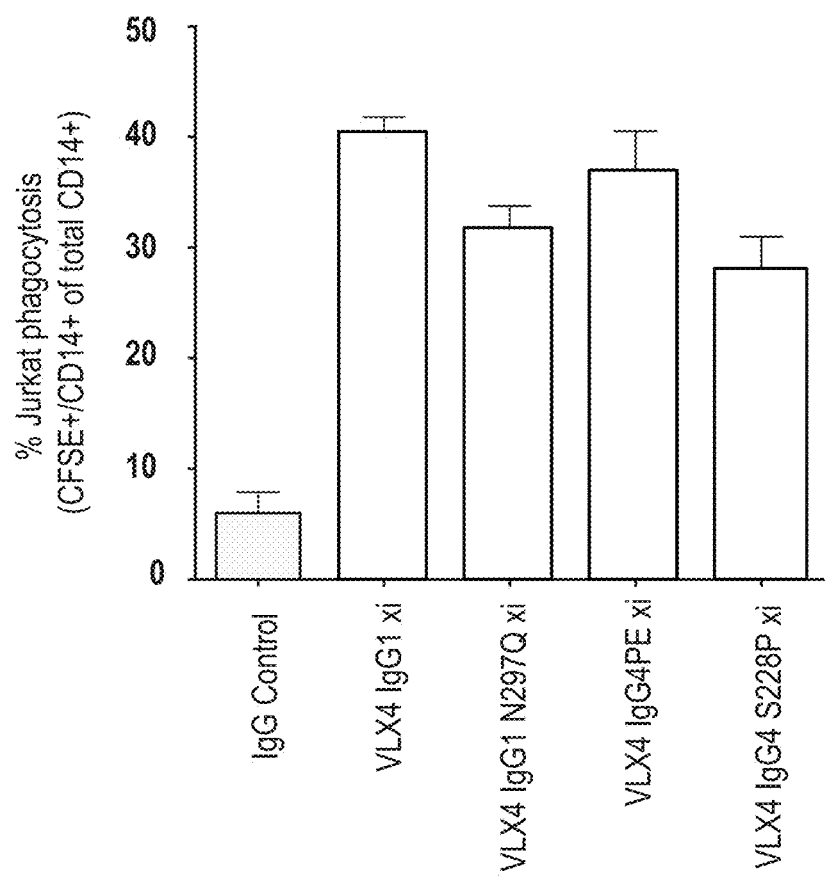

FIG. 8. VLX4 CD47 Chimeric mAbs Increase Phagocytosis of Jurkat T Cells by Human Macrophages. Human macrophages were plated at a concentration of $1 \times 10^4$ cells per well in a 96 well plate and allowed to adhere for 24 hrs. $5 \times 10^4$ CFSE (1 µM) labeled human Jurkat T cells and 1 µg/ml of the VLX4 chimeric mAbs were added to the macrophage cultures and incubated at 37° C. for 2 hrs. Non-phagocytosed Jurkat cells were removed and macrophage cultures were washed extensively. Macrophages were trypsinized and stained for CD14. Flow cytometry was used to determine the percentage of CD14$^+$/CFSE$^+$ cells in the total CD14$^+$ population.

Figure 9A:
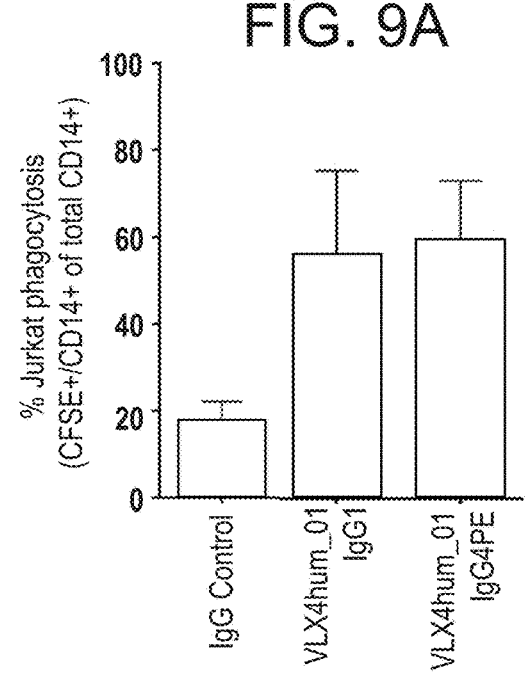

FIG. 9A. VLX4 Humanized mAbs Increase Phagocytosis of Jurkat T Cells by Human Macrophages. Human macrophages were plated at a concentration of $1 \times 10^4$ cells per well in a 96 well plate and allowed to adhere for 24 hrs. $5 \times 10^4$ CFSE (1 µM) labeled human Jurkat T cells and 1 µg/ml of antibody were added to the macrophage cultures and incubated at 37° C. for 2 hrs. Non-phagocytosed Jurkat T cells were removed and macrophage cultures were washed extensively. Macrophages were trypsinized and stained for CD14. Flow cytometry was used to determine the percentage of CD14$^+$/CFSE$^+$ cells in the total CD14$^+$ population.

Figure 9B:
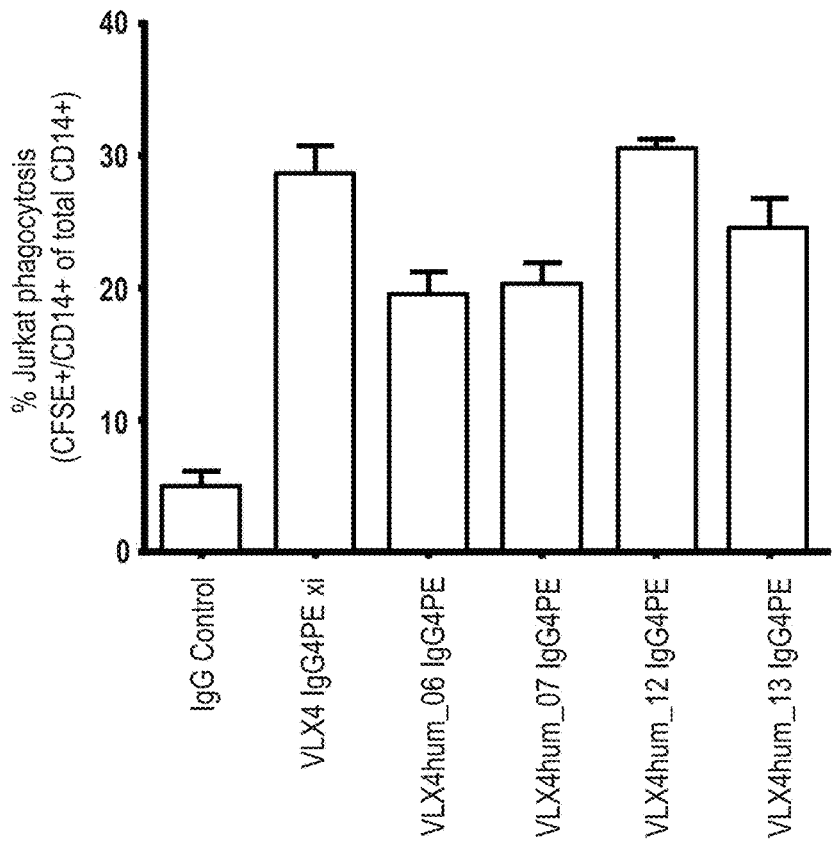

FIG. 9B. VLX4 Humanized mAbs Increase Phagocytosis of Jurkat T Cells by Human Macrophages. Human macrophages were plated at a concentration of $1 \times 10^4$ cells per well in a 96 well plate and allowed to adhere for 24 hrs. $5 \times 10^4$ CFSE (1 µM) labeled human Jurkat T cells and 1 µg/ml of antibody were added to the macrophage cultures and incubated at 37° C. for 2 hrs. Non-phagocytosed Jurkat T cells were removed and macrophage cultures were washed extensively. Macrophages were trypsinized and stained for CD14. Flow cytometry was used to determine the percentage of CD14$^+$/CFSE$^+$ cells in the total CD14$^+$ population.

FIG. 10A. VLX8 CD47 Chimeric mAbs Increase Phagocytosis of Jurkat T Cells by Human Macrophages. Human macrophages were plated at a concentration of $1 \times 10^4$ cells per well in a 96 well plate and allowed to adhere for 24 hrs. $5 \times 10^4$ CFSE (1 µM) labeled human Jurkat T cells and 1 µg/ml of the VLX8 chimeric mAbs were added to the macrophage cultures and incubated at 37° C. for 2 hrs. Non-phagocytosed Jurkat cells were removed and macrophage cultures were washed extensively. Macrophages were trypsinized and stained for CD14. Flow cytometry was used to determine the percentage of CD14$^+$/CFSE$^+$ cells in the total CD14$^+$ population.

FIG. 10B. VLX8 Humanized mAbs Increase Phagocytosis of Jurkat Cells by Human Macrophages. Human macrophages were plated at a concentration of $1 \times 10^4$ cells per well in a 96 well plate and allowed to adhere for 24 hrs. $5 \times 10^4$ CFSE (1 µM) labeled human Jurkat T cells and 1 µg/ml of antibody were added to the macrophage cultures and incubated at 37° C. for 2 hrs. Non-phagocytosed Jurkat T cells were removed and macrophage cultures were washed extensively. Macrophages were trypsinized and stained for CD14. Flow cytometry was used to determine the percentage of CD14$^+$/CFSE$^+$ cells in the total CD14$^+$ population.

Figure 11A:
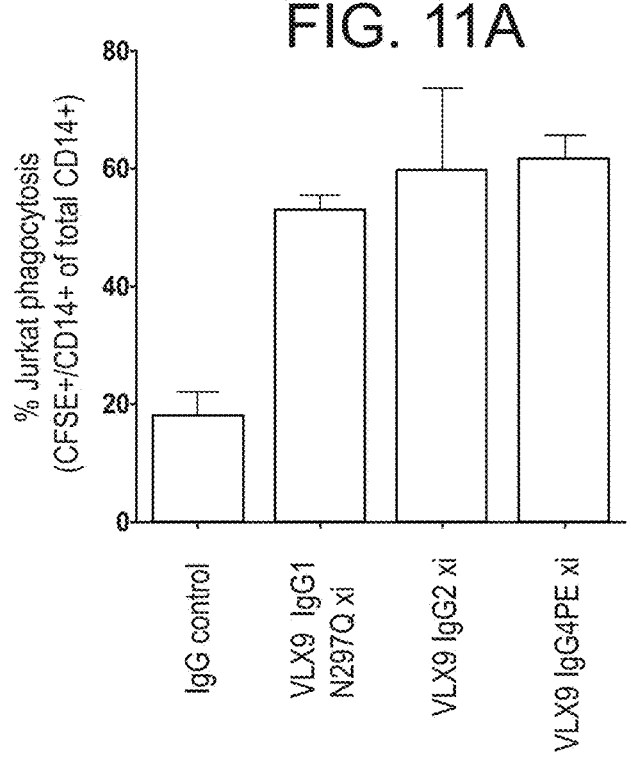

FIG. 11A VLX9 CD47 Chimeric mAbs Increase Phagocytosis of Jurkat T Cells by Human Macrophages. Human macrophages were plated at a concentration of $1 \times 10^4$ cells per well in a 96 well plate and allowed to adhere for 24 hours. $5 \times 10^4$ CFSE (1 µM) labeled human Jurkat T cells and 1 µg/ml of the VLX9 chimeric mAbs were added to the macrophage cultures and incubated at 37° C. for two hours. Non-phagocytosed Jurkat cells were removed and macrophage cultures were washed extensively. Macrophages were trypsinized and stained for CD14. Flow cytometry was used to determine the percentage of CD14+/CFSE+ cells in the total CD14+ population.

Figure 11B:
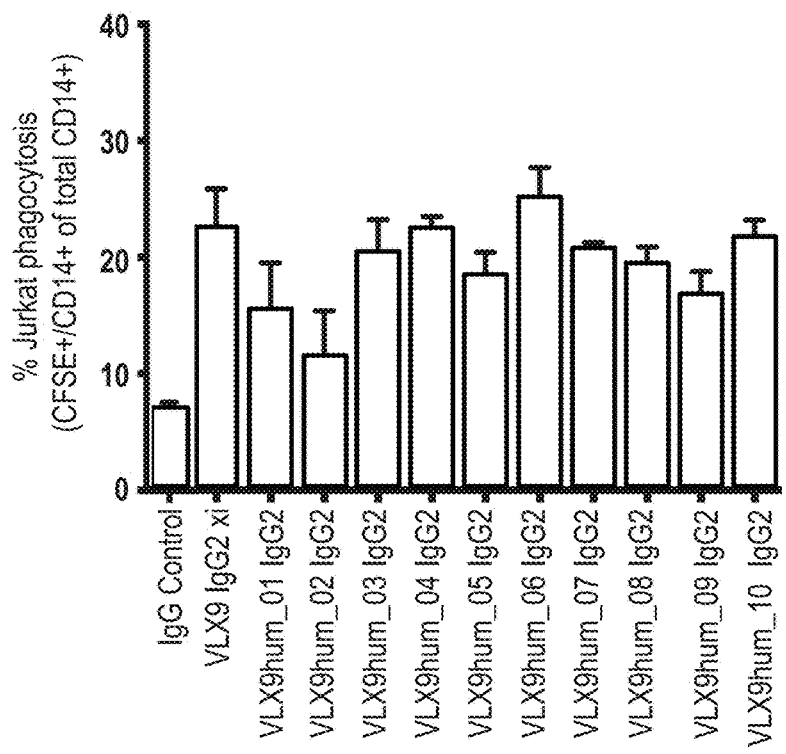

FIG. 11B. VLX9 Humanized mAbs Increase Phagocytosis of Jurkat T Cells by Human Macrophages. Human macrophages were plated at a concentration of $1 \times 10^4$ cells per well in a 96 well plate and allowed to adhere for 24 hours. $5 \times 10^4$ CFSE (1 µM) labeled human Jurkat T cells and 1 µg/ml of antibody were added to the macrophage cultures and incubated at 37° C. for two hours. Non-phagocytosed Jurkat cells were removed and macrophage cultures were washed extensively. Macrophages were trypsinized and stained for CD14. Flow cytometry was used to determine the percentage of CD14+/CFSE+ cells in the total CD14+ population.

Figure 12A:
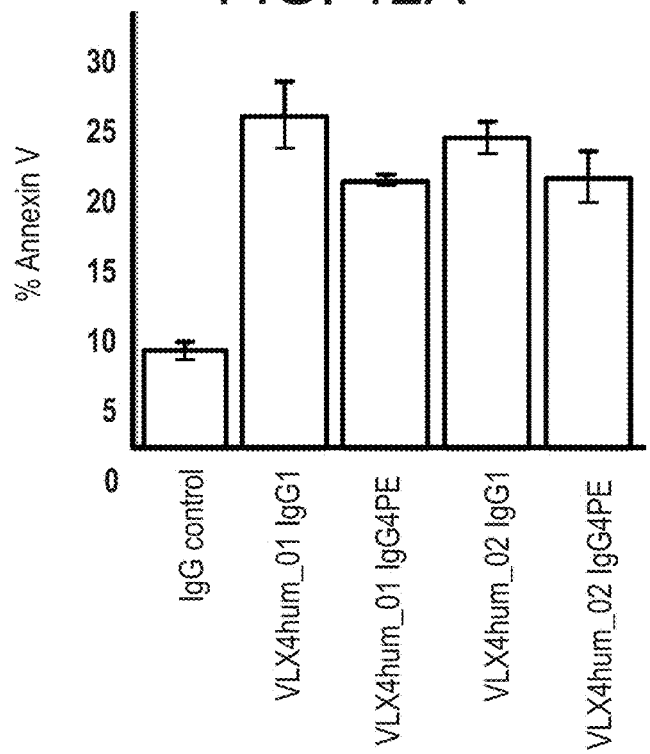

FIG. 12A. Induction of Cell Death in Human Jurkat T Cells by Soluble VLX4 Humanized mAbs. Jurkat T cells ($1\times10^4$) were incubated with 1 µg/ml VLX4 humanized mAbs in 1 ml of RPMI media for 24 hours at 37° C. Cells were then stained for annexin V and the signal was detected by flow cytometry.

Figure 12B:
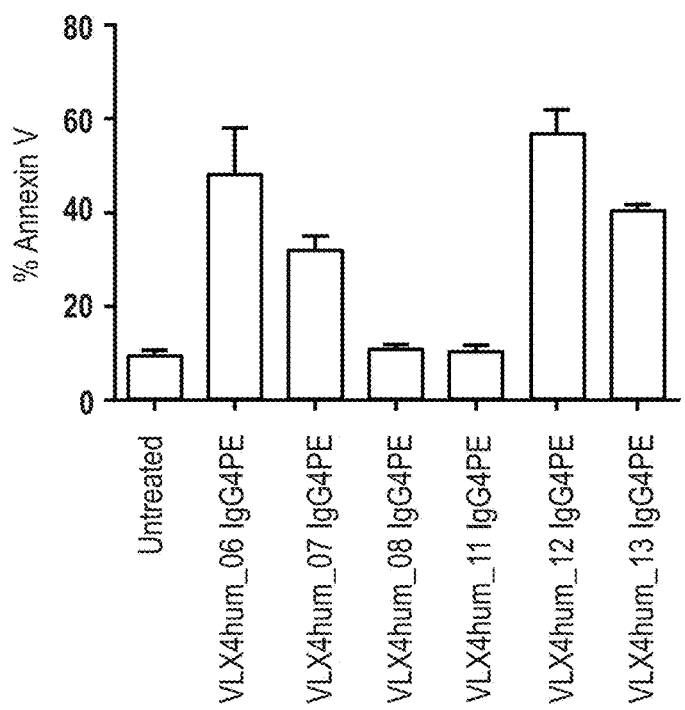

FIG. 12B. Induction of Cell Death in Human Jurkat T Cells by Soluble VLX4 Humanized mAbs. Jurkat T cells ($1\times10^4$) were incubated with 1 µg/ml VLX4 humanized mAbs in 1 ml of RPMI media for 24 hours at 37° C. Cells were then stained for annexin V and the signal was detected by flow cytometry.

Figure 13A:
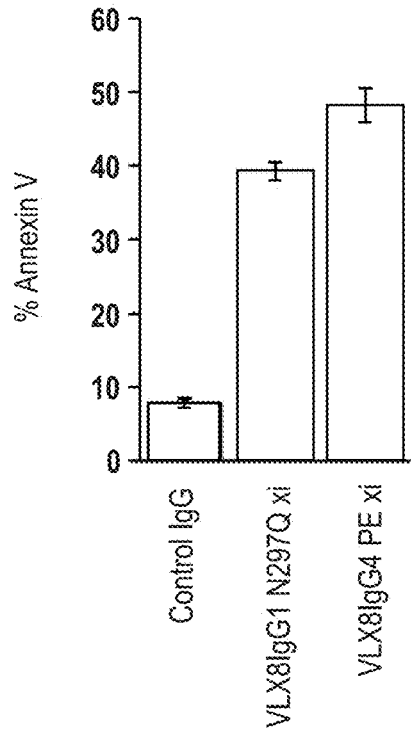

FIG. 13A. Induction of Cell Death in Human Jurkat Cells by Soluble VLX8 CD47 Chimeric mAbs. Jurkat T ALL cells ($1\times10^4$) were incubated with 1 µg/ml VLX8 humanized mAbs in 1 ml of RPMI media for 24 hrs at 37° C. Cells were then stained for annexin V and the signal was detected by flow cytometry.

Figure 13B:
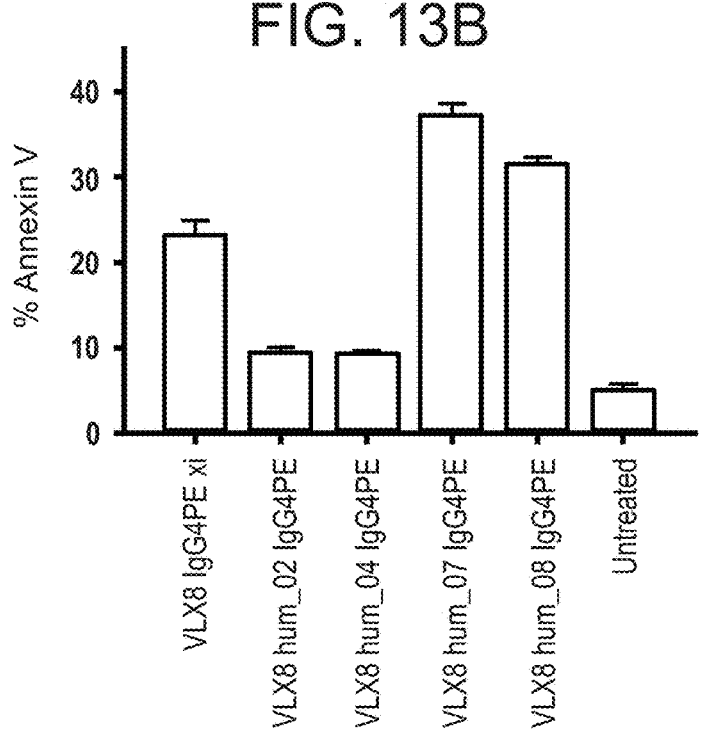

FIG. 13B. Induction of Cell Death in Human Jurkat Cells by Soluble VLX8 Humanized mAbs. Jurkat T ALL cells (1×104) were incubated with 1 µg/ml VLX8 humanized mAbs in 1 ml of RPMI media for 24 hrs at 37° C. Cells were then stained for annexin V and the signal was detected by flow cytometry.

Figure 14A:
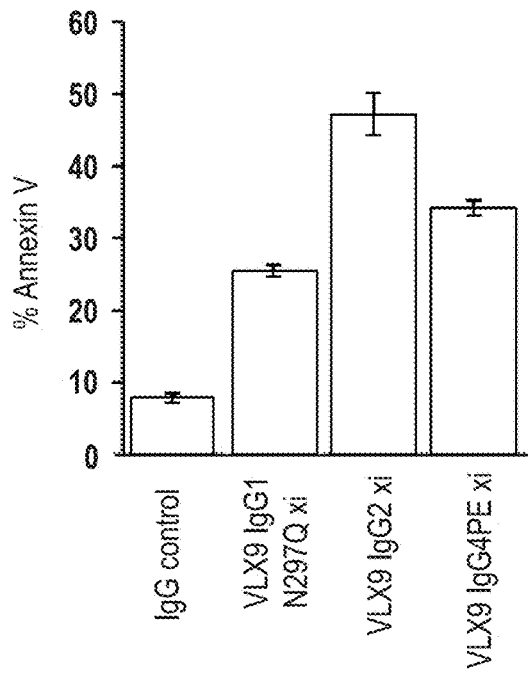

FIG. 14A. Induction of Cell Death of Human Jurkat Cells by Soluble VLX9 Murine/Human Chimeric mAbs. $1\times10^4$ Jurkat cells were incubated with 1 µg/ml of the VLX9 CD47 chimeric mAbs in 0.1 ml of RPMI media for 24 hours 37° C. Cells were then stained with annexin V and the signal analyzed by flow cytometry.

Figure 14B:
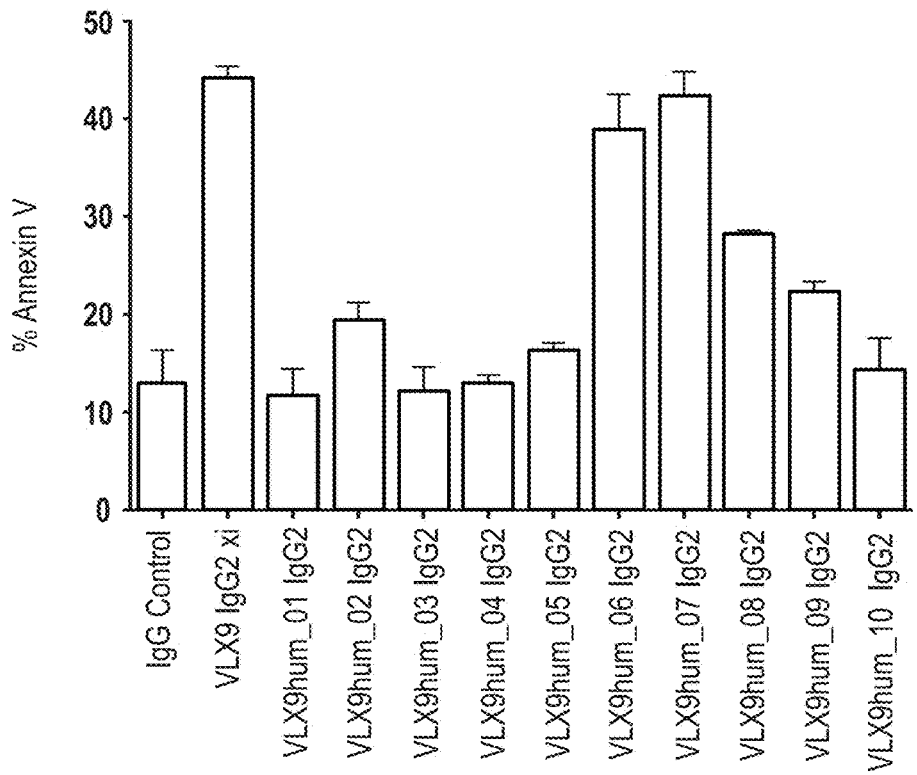

FIG. 14B. Induction of Cell Death in Human Jurkat Cells by Soluble VLX9 Humanized mAbs. Jurkat T ALL cells ($1\times10^4$) were incubated with 1 µg/ml VLX9 humanized mAbs in 1 ml of RPMI media for 24 hours at 37° C. Cells were then stained for annexin V and the signal was detected by flow cytometry. VLX9 IgG2 (xi) is a murine/human chimera.

Figure 15A:
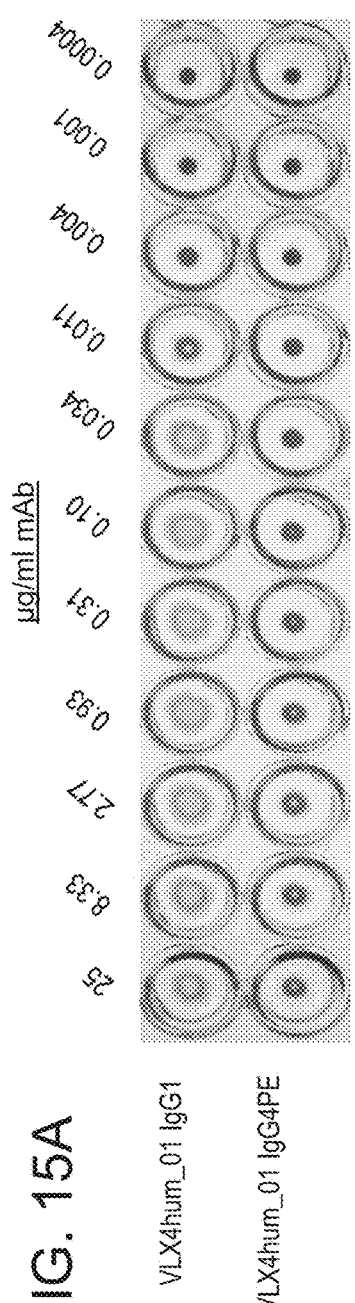

FIG. 15A. Agglutination of hRBCs by VLX4 Humanized mAbs. Hemagglutination was assessed following incubation of hRBCs with various concentrations of humanized VLX4 mAbs (25 µg/mL-0.4 ng/mL). Blood was diluted (1:50) and washed 3 times with PBS/EDTA/BSA. hRBCs were added to U-bottomed 96 well plates with equal volumes of the antibodies (75 µl) and incubated for 3 hrs at 37° C. and overnight at 4° C.

Figure 15B:
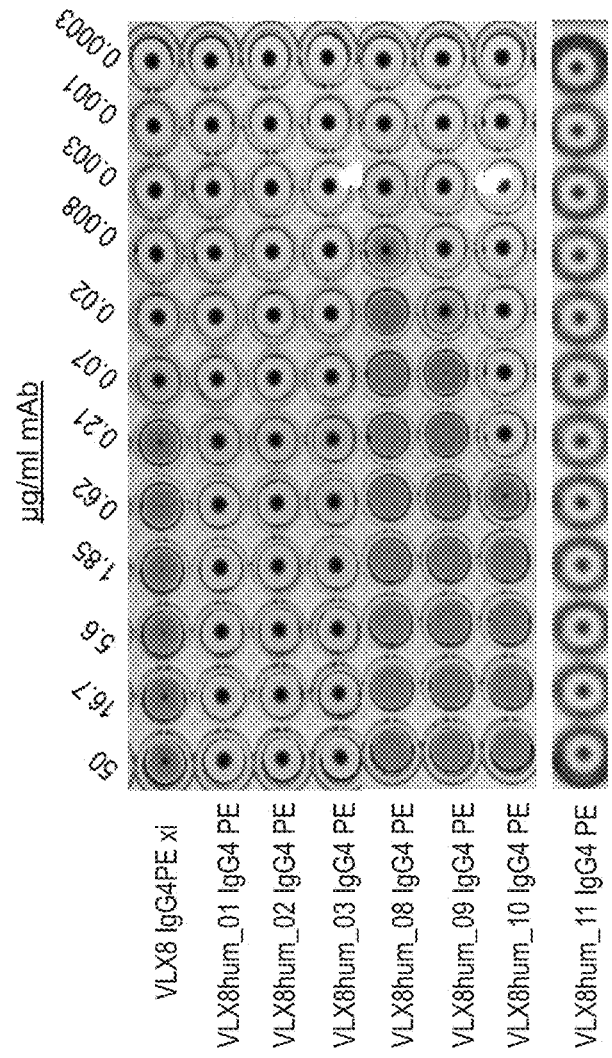

FIG. 15B. Agglutination of hRBCs by VLX8 Chimeric and Humanized mAbs. Hemagglutination was assessed following incubation of hRBCs with various concentrations of humanized VLX4 mAbs (25 µg/mL-0.4 ng/mL). Blood was diluted (1:50) and washed 3 times with PBS/EDTA/BSA. hRBCs were added to U-bottomed 96 well plates with equal volumes of the antibodies (75 µl) and incubated for 3 hrs at 37° C. and overnight at 4° C.

Figure 16A:
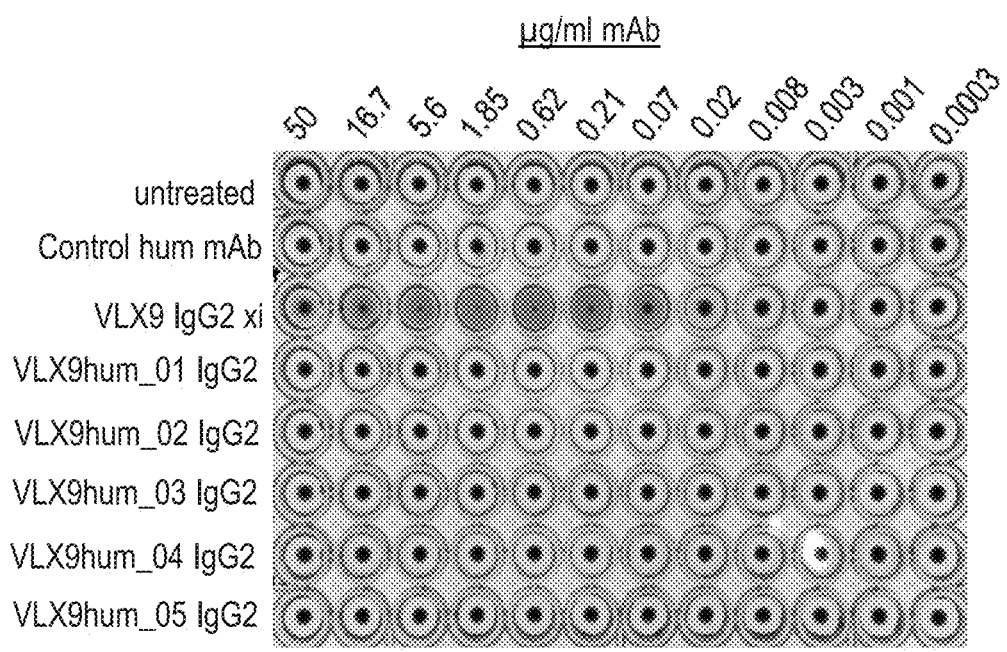

FIG. 16A. Agglutination of Human RBCs by VLX9 Humanized mAbs. Hemagglutination was assessed following incubation of human RBCs with various concentrations of VLX9 IgG2 chimera (xi) and humanized VLX9 mAbs. Blood was diluted (1:50) and washed 3 times with PBS/EDTA/BSA. RBCs were added to U-bottomed 96 well plates with equal volumes of the antibodies (75 µl) and incubated for 3 hrs at 37° C. and overnight at 4° C.

Figure 16B:
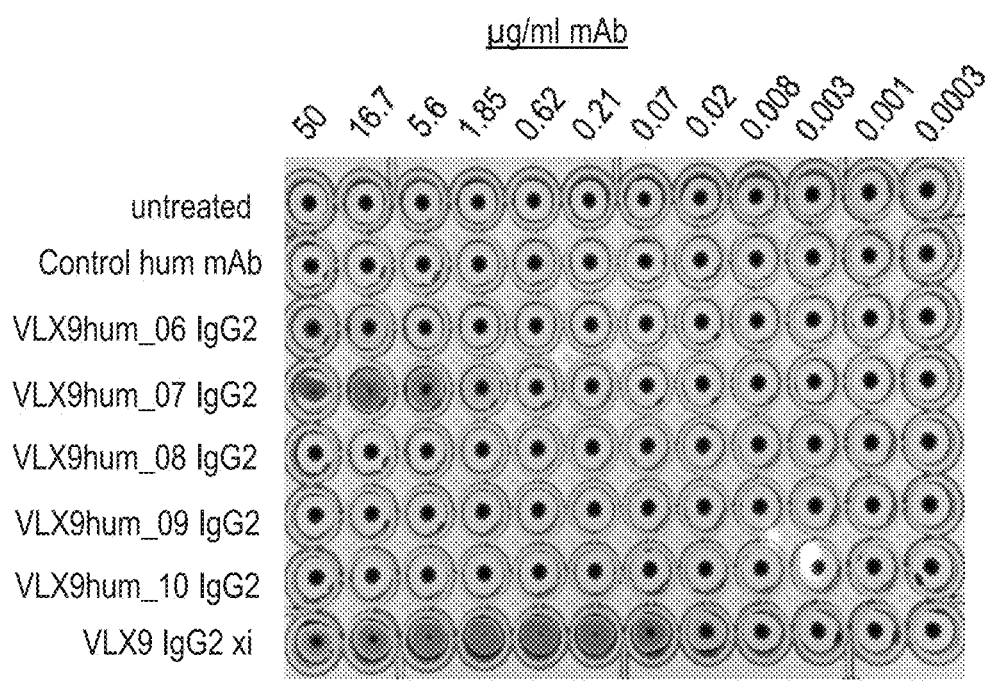

FIG. 16B. Agglutination of Human RBCs by VLX9 Humanized mAbs. Hemagglutination was assessed following incubation of human RBCs with various concentrations of VLX9 IgG2 chimera (xi) and humanized VLX9 mAbs. Blood was diluted (1:50) and washed 3 times with PBS/EDTA/BSA. RBCs were added to U-bottomed 96 well plates with equal volumes of the antibodies (75 µl) and incubated for 3 hrs at 37° C. and overnight at 4° C.

Figure 17:
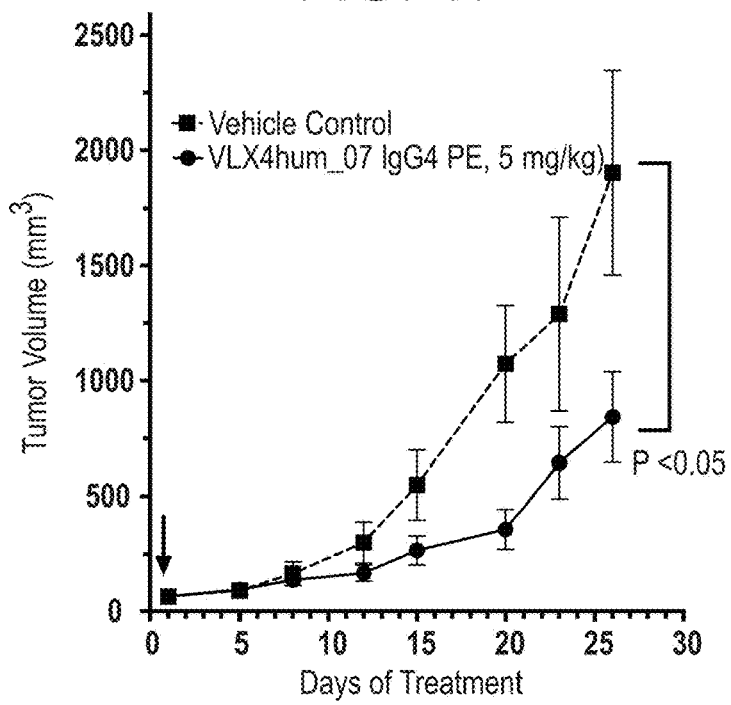

FIG. 17. VLX4 Humanized mAb Reduces Tumor Growth in Raji Xenograft Model. Female NSG mice were inoculated subcutaneously in the right flank with 0.1 mL of a 30% RPMI/70% Matrigel™ (BD Biosciences; Bedford, Mass.) mixture containing a suspension of $5\times10^6$ Raji tumor cells. Five days following inoculation, tumor volumes were measured and mice with palpable tumor volumes of 31-74 mm³ were randomized into 8-10/group. VLX4hum_07 or PBS (control) administration was initiated at this time. Mice were treated with 5 mg/kg of antibody 5×/week for 4 weeks by intraperitoneal injection. Tumor volumes and body weights were recorded twice weekly.

Figure 18:
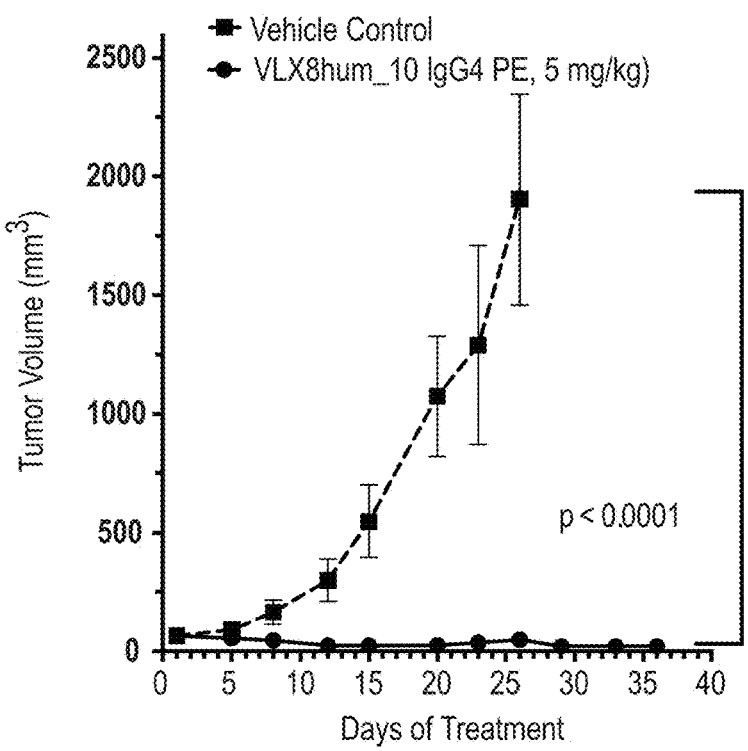

FIG. 18. VLX8 Humanized mAb Reduces Tumor Growth in Raji Xenograft Model. Female NSG mice were inoculated subcutaneously in the right flank with 0.1 mL of a 30% RPMI/70% Matrigel™ (BD Biosciences; Bedford, Mass.) mixture containing a suspension of $5\times10^6$ Raji tumor cells. Five days following inoculation, tumor volumes were measured and mice with palpable tumor volumes of 31-74 mm³ were randomized into 8-10/group. VLX8hum_10 or PBS (control) administration was initiated at this time. Mice were treated with 5 mg/kg of antibody 5×/week for 4 weeks by intraperitoneal injection. Tumor volumes and body weights were recorded twice weekly.

Figure 19:
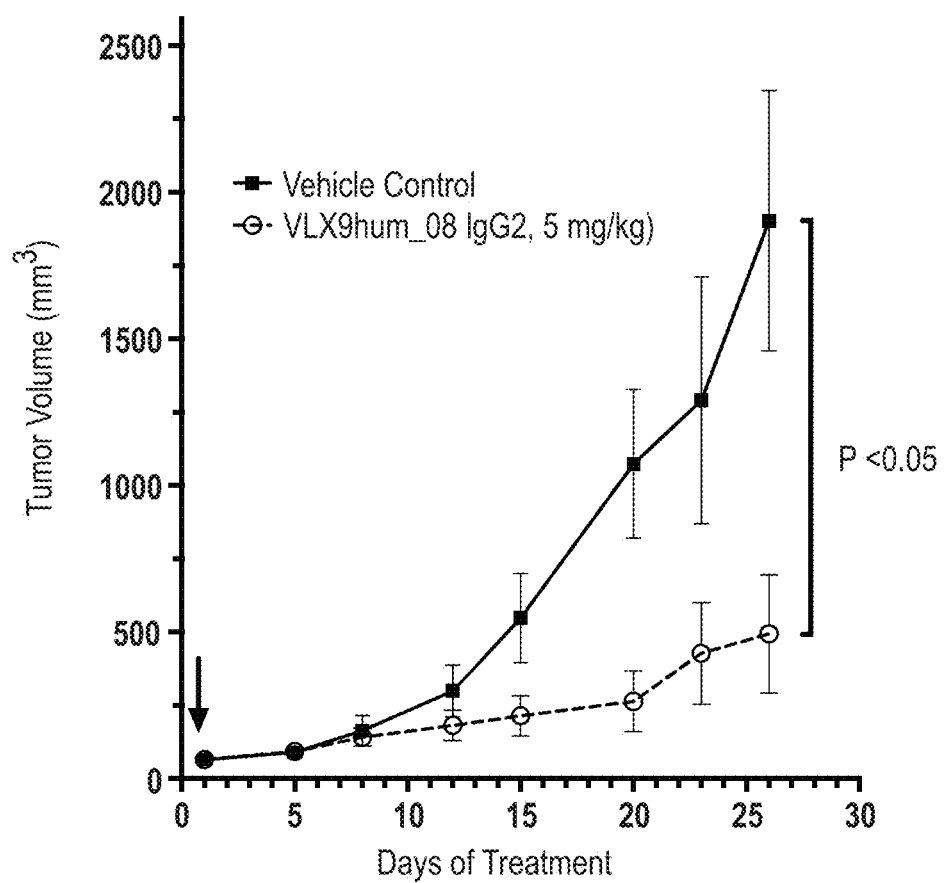

FIG. 19. VLX9 Humanized mAb Reduces Tumor Growth in Raji Xenograft Model. Female NSG mice were inoculated subcutaneously in the right flank with 0.1 mL of a 30% RPMI/70% Matrigel™ (BD Biosciences; Bedford, Mass.) mixture containing a suspension of $5\times10^6$ Raji tumor cells. Five days following inoculation, tumor volumes were measured and mice with palpable tumor volumes of 31-74 mm³ were randomized into 8-10/group. VLX9hum_08 IgG2 or PBS (control) administration was initiated at this time. Mice were treated with 5 mg/kg of antibody 5×/week for 4 weeks by intraperitoneal injection. Tumor volumes and body weights were recorded twice weekly.

Figure 20A:
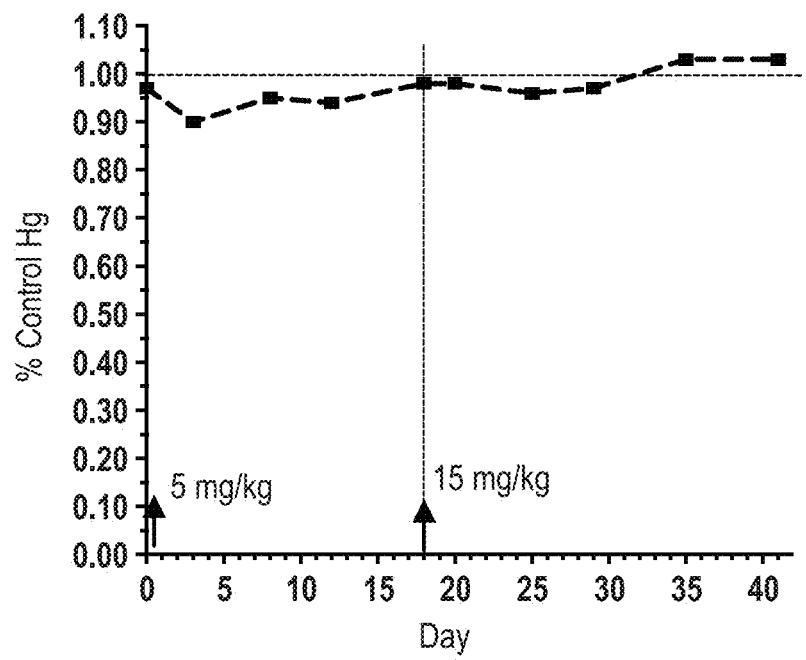

FIG. 20A. Hemoglobin Levels in Blood following Administration of a Humanized VLX9 mAb to Cynomolgus Monkeys by Intravenous Infusion. VLX9hum_08 IgG2 or vehicle were administered as a one hour intravenous infusion a dose of 5 mg/kg on day 1 and a dose of 15 mg/kg on day 18. Hemoglobin levels were monitored throughout the study and normalized to control values.

Figure 20B:
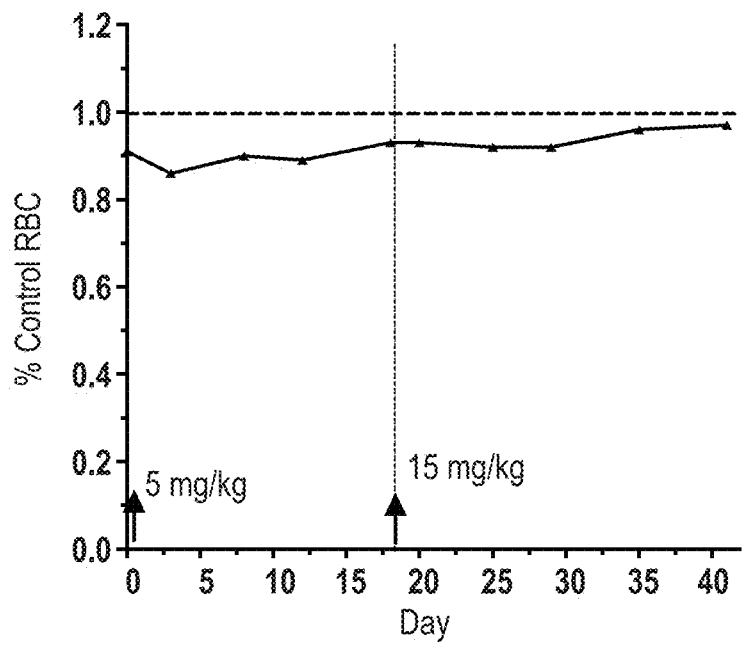

FIG. 20B. RBC Levels in Blood following Administration of Humanized VLX9 mAbs to Cynomolgus Monkeys by Intravenous Infusion. VLX9hum_08 IgG2 or vehicle was administered as a one hour intravenous infusion a dose of 5 mg/kg on day 1 and a dose of 15 mg/kg on day 18. RBC levels were monitored throughout the study and normalized to control values.

Figure 21:
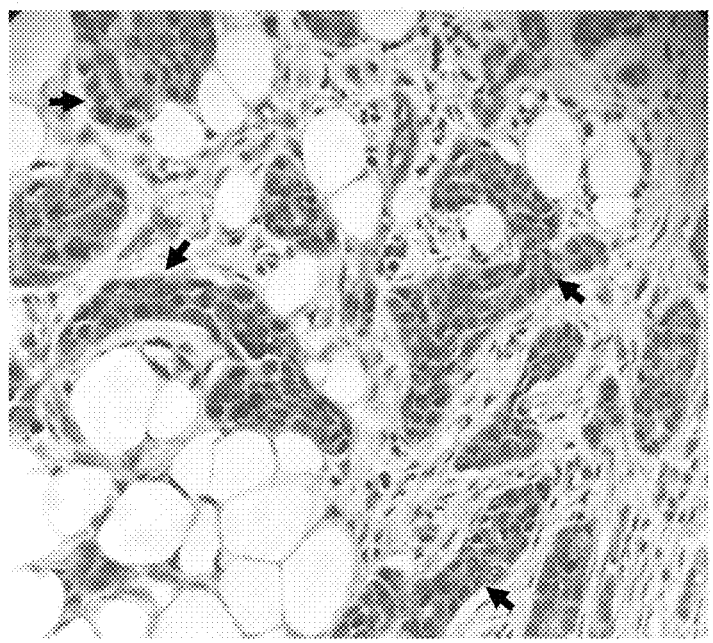

FIG. 21. Immunohistochemical Staining of CD47 in Human Tumor Tissue with Anti-Murine/Rabbit Chimeric mAb. CD47 was localized in human breast cancer tissue using VLX4 mouse/rabbit chimeric mAb. Paraffin-embedded tissue was sectioned, stained with 4 ug/ml of purified antibody and localized with anti-rabbit HRP secondary antibody. Arrows denote positive areas of CD47 staining.

Figure 22:
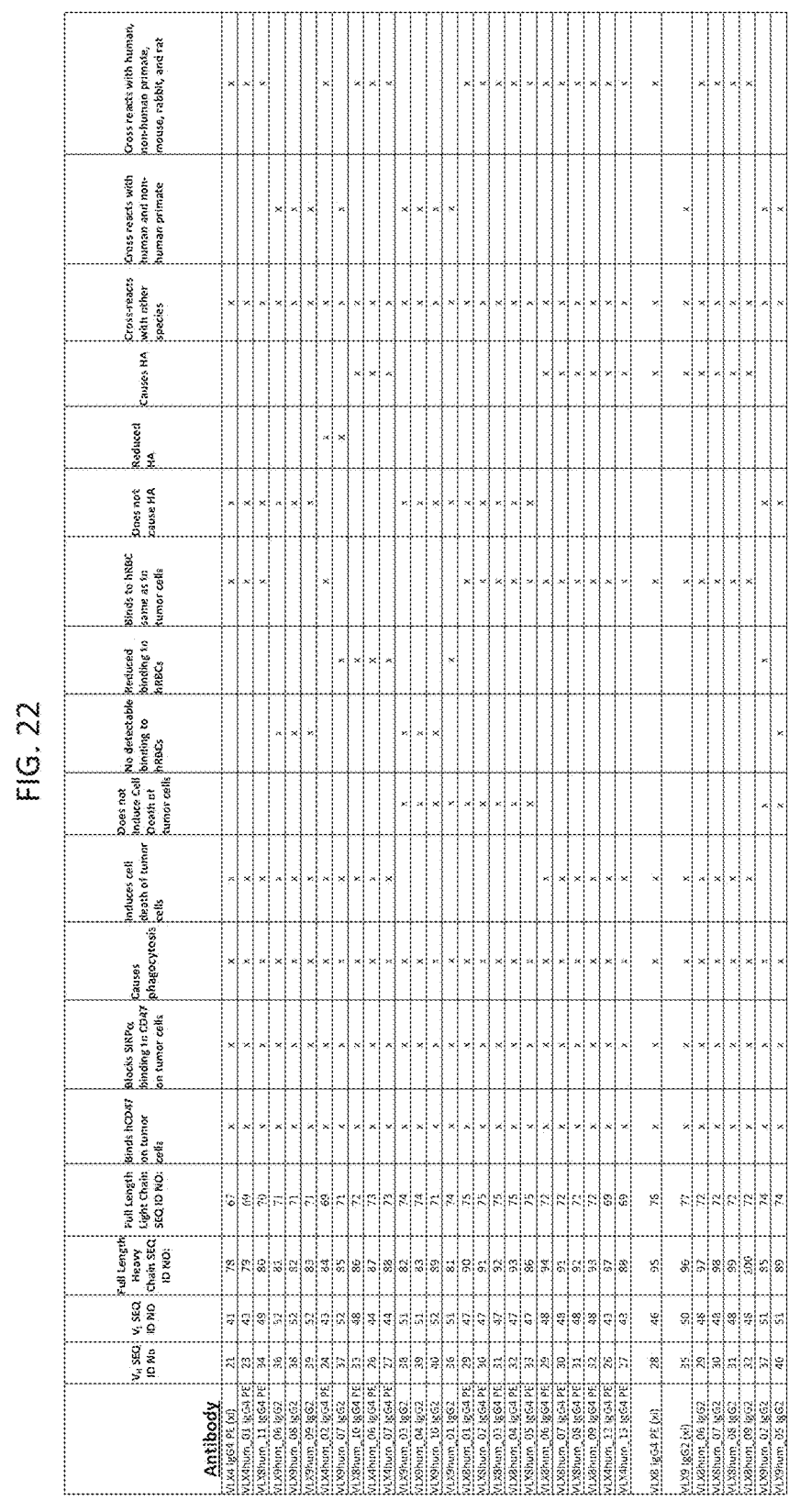

FIG. 22. Summary of Anti-CD47 Antibody Properties.

DETAILED DESCRIPTION OF THE EMBODIMENTS OF THE DISCLOSURE

Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo or polynucleotide chemistry and hybridization described herein are those well-known and commonly used in the art.

As used herein, the term "CD47", "integrin-associated protein (IAP)", "ovarian cancer antigen OA3", "Rh-related antigen" and "MERG" are synonymous and may be used interchangeably.

The term "anti-CD47 antibody" refer to an antibody of the disclosure which is intended for use as a therapeutic or diagnostic agent, and therefore will typically possess the binding affinity required to be useful as a therapeutic and/or diagnostic agent.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts" with or directed against is meant that the antibody reacts with one or more antigenic determinants of the desired antigen and does not react with other polypeptides or binds at a much lower affinity ($K_d > 10^{-6}$). Antibodies include but are not limited to, polyclonal, monoclonal, chimeric, Fab fragments, Fab' fragments, F(ab')2 fragments, single chain Fv fragments, and one-armed antibodies.

As used herein, the term "monoclonal antibody" (mAb) as applied to the present antibody compounds refers to an antibody that is derived from a single copy or clone including, for example, any eukaryotic, prokaryotic, or phage clone, and not the method by which it is produced. mAbs of the present disclosure preferably exist in a homogeneous or substantially homogeneous population. Complete mAbs contain 2 heavy chains and 2 light chains.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

As disclosed herein, "antibody compounds" refers to mAbs and antigen-binding fragments thereof. Additional antibody compounds exhibiting similar functional properties according to the present disclosure can be generated by conventional methods. For example, mice can be immunized with human CD47 or fragments thereof, the resulting antibodies can be recovered and purified, and determination of whether they possess binding and functional properties similar to or the same as the antibody compounds disclosed herein can be assessed by the methods disclosed in Examples 3-11, below. Antigen-binding fragments can also be prepared by conventional methods. Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15.

The monoclonal antibodies encompass antibodies in which a portion of the heavy and/or light chain is identical with, or homologous to, corresponding sequences in murine antibodies, in particular the murine CDRs, while the remainder of the chain(s) is (are) identical with, or homologous to, corresponding sequences in human antibodies. Other embodiments of the disclosure include antigen-binding fragments of these monoclonal antibodies that exhibit binding and biological properties similar or identical to the monoclonal antibodies. The antibodies of the present disclosure can comprise kappa or lambda light chain constant regions, and heavy chain IgA, IgD, IgE, IgG, or IgM constant regions, including those of IgG subclasses IgG1, IgG2, IgG3, and IgG4 and in some cases with various mutations to alter Fc receptor function.

The monoclonal antibodies containing the presently disclosed murine CDRs can be prepared by any of the various methods known to those skilled in the art, including recombinant DNA methods.

Reviews of current methods for antibody engineering and improvement can be found, for example, in P. Chames, Ed., (2012) *Antibody Engineering: Methods and Protocols, Second Edition (Methods in Molecular Biology, Book 907)*, Humana Press, ISBN-10: 1617799734; C. R. Wood, Ed., (2011) *Antibody Drug Discovery (Molecular Medicine and Medicinal Chemistry, Book 4)*, Imperial College Press; R. Kontermann and S. Dubel, Eds., (2010) *Antibody Engineering Volumes 1 and 2* (Springer Protocols), Second Edition; and W. Strohl and L. Strohl (2012) *Therapeutic antibody engineering: Current and future advances driving the strongest growth area in the pharmaceutical industry*, Woodhead Publishing.

Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, N.Y., chapters 5-8 and 15.

A full-length antibody as it exists naturally is a "Y" shaped immunoglobulin (Ig) molecule comprising four polypeptide chains: two identical heavy (H) chains and two identical light (L) chains, interconnected by disulfide bonds. The amino terminal portion of each chain, termed the fragment antigen binding region (FAB), includes a variable region of about 100-110 or more amino acids primarily responsible for antigen recognition via the complementarity determining regions (CDRs) contained therein. The carboxy-terminal portion of each chain defines a constant region (the "Fc" region) primarily responsible for effector function.

The CDRs are interspersed with regions that are more conserved, termed frameworks ("FRs"). Amino acid sequences of many FRs are well known in the art. Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions are in accordance with the well-known Kabat numbering convention Kabat et al. (1991) *Sequences of Proteins of Immunological Interest*, Fifth Edition. NIH Publication No. 91-3242.

As described herein, the "antigen-binding site" can also be defined as the "Hypervariable regions", "HVRs", or "HVs", and refer to the structurally hypervariable regions of antibody variable domains as defined by Chothia and Lesk (Chothia and Lesk, Mol. Biol. 196:901-917, 1987). There are six HVRs, three in VH (H1, H2, H3) and three in VL (L1, L2, L3). We used herein CDRs as defined by Kabat except in H-CDR1, which is extended to include H1.

There are five types of mammalian immunoglobulin (Ig) heavy chains, denoted by the Greek letters α (alpha), δ (delta), ε (epsilon), γ (gamma), and μ (mu), which define the class or isotype of an antibody as IgA, IgD, IgE, IgG, or IgM, respectively. IgG antibodies can be further divided into subclasses, for example, IgG1, IgG2, IgG3, and IgG4.

Each heavy chain type is characterized by a particular constant region with a sequence well known in the art. The constant region is identical in all antibodies of the same isotype, but differs in antibodies of different isotypes. Heavy chains γ, α, and δ have a constant region composed of three tandem immunoglobulin (Ig) domains, and a hinge region for added flexibility. Heavy chains μ and ε have a constant region composed of four Ig domains.

The hinge region is a flexible amino acid stretch that links the Fc and Fab portions of an antibody. This regions contains cysteine residues that can form disulfide bonds, connecting two heavy chains together.

The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, light chains are classified as kappa (κ) or lambda (λ), and are characterized by a particular constant region as known in the art. A light chain has two successive domains: one variable domain at the amino-terminal end, and one constant domain at the carboxy-terminal end. Each antibody contains two light chains that are always identical; only one type of light chain, κ or λ, is present per antibody in mammals.

The Fc region, composed of two heavy chains that contribute three or four constant domains depending on the class of the antibody, plays a role in modulating immune cell activity. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects, including opsonization, cell lysis, and degranulation of mast cells, basophils and eosinophils.

As used herein, the term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous in the linear sequence.

As used herein, the terms "specifically binds", "bind specifically", "specific binding", and the like as applied to the present antibody compounds refer to the ability of a specific binding agent (such as an antibody) to bind to a target molecular species in preference to binding to other molecular species with which the specific binding agent and target molecular species are admixed. A specific binding agent is said specifically to recognize a target molecular species when it can bind specifically to that target.

As used herein, the term "binding affinity" refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

As used herein, the term "sequence identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J. Applied Math.*, 48: 1073 (1988). Methods to determine identity are designed to give the largest match between the sequences tested. Moreover, methods to determine identity are codified in publicly available computer programs.

Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, Altschul, S. F. et al., *J. Mol. Biol.* 215: 403-410 (1990) and Altschul et al. *Nucl. Acids Res.* 25: 3389-3402 (1997).

One example of an algorithm that is suitable for determining percent sequence identity and sequence similarity is the BLAST algorithm, which is described in (Altschul, S., et al., NCBI NLM NIH Bethesda, Md. 20894; and Altschul, S., et al., *J. Mol. Biol.* 215: 403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold.

These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always; 0) and N (penalty score for mismatching residues; always; 0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

As used herein, the terms "humanized", "humanization", and the like, refer to grafting of the murine monoclonal antibody CDRs disclosed herein to human FRs and constant regions. Also encompassed by these terms are possible further modifications to the murine CDRs, and human FRs, by the methods disclosed in, for example, Kashmiri et al. (2005) *Methods* 36(1):25-34 and Hou et al. (2008) *J. Biochem.* 144(1):115-120, respectively, to improve various antibody properties, as discussed below.

As used herein, the term "humanized antibodies" refers to mAbs and antigen binding fragments thereof, including the antibody compounds disclosed herein, that have binding and functional properties according to the disclosure similar to those disclosed herein, and that have FRs and constant regions that are substantially human or fully human surrounding CDRs derived from a non-human antibody.

As used herein, the term "FR" or "framework sequence" refers to any one of FRs 1 to 4. Humanized antibodies and antigen binding fragments encompassed by the present disclosure include molecules wherein any one or more of FRs 1 to 4 is substantially or fully human, i.e., wherein any of the possible combinations of individual substantially or fully human FRs 1 to 4, is present. For example, this includes molecules in which FR1 and FR2, FR1 and FR3, FR1, FR2, and FR3, etc., are substantially or fully human. Substantially human frameworks are those that have at least 80% sequence identity to a known human germline framework sequence. Preferably, the substantially human frameworks have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity, to a framework sequence disclosed herein, or to a known human germline framework sequence.

Fully human frameworks are those that are identical to a known human germline framework sequence. Human FR germline sequences can be obtained from the international ImMunoGeneTics (IMGT) database and from *The Immunoglobulin FactsBook* by Marie-Paule Lefranc and Gerard Lefranc, Academic Press, 2001, the contents of which are herein incorporated by reference in their entirety.

The Immunoglobulin Facts Book is a compendium of the human germline immunoglobulin genes that are used to create the human antibody repertoire, and includes entries for 203 genes and 459 alleles, with a total of 837 displayed sequences. The individual entries comprise all the human immunoglobulin constant genes, and germline variable, diversity, and joining genes that have at least one functional or open reading frame allele, and which are localized in the three major loci. For example, germline light chain FRs can be selected from the group consisting of: IGKV3D-20, IGKV2-30, IGKV2-29, IGKV2-28, IGKV1-27, IGKV3-20, IGKV1-17, IGKV1-16, 1-6, IGKV1-5, IGKV1-12, IGKV1D-16, IGKV2D-28, IGKV2D-29, IGKV3-11, IGKV1-9, IGKV1-39, IGKV1D-39 and IGKV1D-33 and IGKJ1-5 and germline heavy chain FRs can be selected from the group consisting of: IGHV1-2, IGHV1-18, IGHV1-46, IGHV1-69, IGHV2-5, IGHV2-26, IGHV2-70, IGHV1-3, IGHV1-8, IGHV3-9, IGHV3-11, IGHV3-15, IGHV3-20, IGHV3-66, IGHV3-72, IGHV3-74, IGHV4-31, IGHV3-21, IGHV3-23, IGHV3-30, IGHV3-48, IGHV4-39, IGHV4-59 and IGHV5-51 and IGHJ1-6.

Substantially human FRs are those that have at least 80% sequence identity to a known human germline FR sequence. Preferably, the substantially human frameworks have at least 85%, at least 90%, at least 95%, at least 96%, at least 97%, at least 98%, or at least 99% sequence identity, to a framework sequences disclosed herein, or to a known human germline framework sequence.

CDRs encompassed by the present disclosure include not only those specifically disclosed herein, but also CDR sequences having sequence identities of at least 80%, at least 85%, at least 90%, at least 95%, at least 96%, at least 97%, at least 98%, or at least 99% sequence identity to a CDR sequence disclosed herein. Alternatively, CDRs encompassed by the present disclosure include not only those specifically disclosed herein, but also CDR sequences having 1, 2, 3, 4, or 5 amino acid changes at corresponding positions compared to CDR sequences disclosed herein. Such sequence identical, or amino acid modified, CDRs preferably bind to the antigen recognized by the intact antibody.

Humanized antibodies in addition to those disclosed herein exhibiting similar functional properties according to the present disclosure can be generated using several different methods Almagro et al. *Frontiers in Biosciences*. Humanization of antibodies. (2008) January 1; 13:1619-33. In one approach, the parent antibody compound CDRs are grafted into a human framework that has a high sequence identity with the parent antibody compound framework. The sequence identity of the new framework will generally be at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identical to the sequence of the corresponding framework in the parent antibody compound. In the case of frameworks having fewer than 100 amino acid residues, one, two, three, four, five, six, seven, eight, nine, or ten amino acid residues can be changed. This grafting may result in a reduction in binding affinity compared to that of the parent antibody. If this is the case, the framework can be back-mutated to the parent framework at certain positions based on specific criteria disclosed by Queen et al. (1991) *Proc. Natl. Acad. Sci. USA* 88:2869. Additional references describing methods useful to generate humanized variants based on homology and back mutations include as described in Olimpieri et al. *Bioinformatics*. 2015 Feb. 1; 31(3):434-435 and U.S. Pat. Nos.

4,816,397, 5,225,539, and 5,693,761; and the method of Winter and co-workers (Jones et al. (1986) *Nature* 321:522-525; Riechmann et al. (1988) *Nature* 332:323-327; and Verhoeyen et al. (1988) *Science* 239:1534-1536.

Humanization began with chimerization, a method developed during the first half of the 1980's (Morrison, S. L., M. J. Johnson, L. A. Herzenberg & V. T. Oi: Chimeric human antibody molecules: mouse antigen-binding domains with human constant region domains. *Proc. Natl. Acad. Sci. USA.*, 81, 6851-5 (1984)), consisting of combining the variable (V) domains of murine antibodies with human constant (C) domains to generate molecules with ~70% of human content.

Several different methods can be used to generate humanized antibodies, which are described herein. In one approach, the parent antibody compound CDRs are grafted into a human FR that has a high sequence identity with the parent antibody compound framework. The sequence identity of the new FR will generally be at least 80%, at least 85%, at least 90%, at least 95%, at least 96%, at least 97%, at least 98%, or at least 99% identical to the sequence of the corresponding FR in the parent antibody compound. In the case of FRs having fewer than 100 amino acid residues, one, two, three, four, five, or more amino acid residues can be changed. This grafting may result in a reduction in binding affinity compared to that of the parent antibody. If this is the case, the FR can be back-mutated to the parent framework at certain positions based on specific criteria disclosed by Queen et al. (1991) *Proc. Natl. Acad. Sci. USA* 88:2869. Additional references describing methods useful to generate humanized variants based on homology and back mutations include as described in Olimpieri et al. Bioinformatics. 2015 Feb. 1; 31(3):434-435 and U.S. Pat. Nos. 4,816,397, 5,225,539, and 5,693,761; and the method of Winter and co-workers (Jones et al. (1986) *Nature* 321:522-525; Riechmann et al. (1988) *Nature* 332:323-327; and Verhoeyen et al. (1988) *Science* 239:1534-1536.

The identification of residues to consider for back-mutation can be carried out as described below. When an amino acid falls under the following category, the framework amino acid of the human germ-line sequence that is being used (the "acceptor FR") is replaced by a framework amino acid from a framework of the parent antibody compound (the "donor FR"):

(a) the amino acid in the human FR of the acceptor framework is unusual for human frameworks at that position, whereas the corresponding amino acid in the donor immunoglobulin is typical for human frameworks at that position;

(b) the position of the amino acid is immediately adjacent to one of the CDRs; or (c) any side chain atom of a framework amino acid is within about 5-6 angstroms (center-to-center) of any atom of a CDR amino acid in a three dimensional immunoglobulin model.

When each of the amino acids in the human FR of the acceptor framework and a corresponding amino acid in the donor framework is generally unusual for human frameworks at that position, such amino acid can be replaced by an amino acid typical for human frameworks at that position. This back-mutation criterion enables one to recover the activity of the parent antibody compound.

Another approach to generating humanized antibodies exhibiting similar functional properties to the antibody compounds disclosed herein involves randomly mutating amino acids within the grafted CDRs without changing the framework, and screening the resultant molecules for binding affinity and other functional properties that are as good as, or better than, those of the parent antibody compounds. Single mutations can also be introduced at each amino acid position within each CDR, followed by assessing the effects of such mutations on binding affinity and other functional properties. Single mutations producing improved properties can be combined to assess their effects in combination with one another.

Further, a combination of both of the foregoing approaches is possible. After CDR grafting, one can back-mutate specific FRs in addition to introducing amino acid changes in the CDRs. This methodology is described in Wu et al. (1999) *J. Mol. Biol.* 294: 151-162.

Applying the teachings of the present disclosure, a person skilled in the art can use common techniques, e.g., site-directed mutagenesis, to substitute amino acids within the presently disclosed CDR and FR sequences and thereby generate further variable region amino acid sequences derived from the present sequences. Up to all naturally occurring amino acids can be introduced at a specific substitution site. The methods disclosed herein can then be used to screen these additional variable region amino acid sequences to identify sequences having the indicated in vivo functions. In this way, further sequences suitable for preparing humanized antibodies and antigen-binding portions thereof in accordance with the present disclosure can be identified. Preferably, amino acid substitution within the frameworks is restricted to one, two, three, four, or five positions within any one or more of the four light chain and/or heavy chain FRs disclosed herein. Preferably, amino acid substitution within the CDRs is restricted to one, two, three, four, or five positions within any one or more of the three light chain and/or heavy chain CDRs. Combinations of the various changes within these FRs and CDRs described above are also possible.

That the functional properties of the antibody compounds generated by introducing the amino acid modifications discussed above conform to those exhibited by the specific molecules disclosed herein can be confirmed by the methods in Examples disclosed herein.

As described above, to circumvent the problem of eliciting human anti-murine antibody (HAMA) response in patients, murine antibodies have been genetically manipulated to progressively replace their murine content with the amino acid residues present in their human counterparts by grafting their complementarity determining regions (CDRs) onto the variable light ($V_L$) and variable heavy ($V_H$) frameworks of human immunoglobulin molecules, while retaining those murine framework residues deemed essential for the integrity of the antigen-combining site. However, the xenogeneic CDRs of the humanized antibodies may evoke anti-idiotypic (anti-Id) response in patients.

To minimize the anti-Id response, a procedure to humanize xenogeneic antibodies by grafting onto the human frameworks only the CDR residues most crucial in the antibody-ligand interaction, called "SDR grafting", has been developed, wherein only the crucial specificity determining residues (SDRs) of CDRS are grafted onto the human frameworks. This procedure, described in Kashmiri et al. (2005) *Methods* 36(1):25-34, involves identification of SDRs through the help of a database of the three-dimensional structures of the antigen-antibody complexes of known structures, or by mutational analysis of the antibody-combining site. An alternative approach to humanization involving retention of more CDR residues is based on grafting of the 'abbreviated' CDRs, the stretches of CDR residues that include all the SDRs. Kashmiri et al. also discloses a procedure to assess the reactivity of humanized antibodies to sera from patients who had been administered the murine antibody.

Another strategy for constructing human antibody variants with improved immunogenic properties is disclosed in Hou et al. (2008) *J. Biochem.* 144(1):115-120. These authors developed a humanized antibody from 4C8, a murine anti-human CD34 monoclonal antibody, by CDR grafting using a molecular model of 4C8 built by computer-assisted homology modelling. Using this molecular model, the authors identified FR residues of potential importance in antigen binding. A humanized version of 4C8 was generated by transferring these key murine FR residues onto a human antibody framework that was selected based on homology to the murine antibody FR, together with the murine CDR residues. The resulting humanized antibody was shown to possess antigen-binding affinity and specificity similar to that of the original murine antibody, suggesting that it might be an alternative to murine anti-CD34 antibodies routinely used clinically.

Embodiments of the present disclosure encompass antibodies created to avoid recognition by the human immune system containing CDRs disclosed herein in any combinatorial form such that contemplated mAbs can contain the set of CDRs from a single murine mAb disclosed herein, or light and heavy chains containing sets of CDRs comprising individual CDRs derived from two or three of the disclosed murine mAbs. Such mAbs can be created by standard techniques of molecular biology and screened for desired activities using assays described herein. In this way, the disclosure provides a "mix and match" approach to create novel mAbs comprising a mixture of CDRs from the disclosed murine mAbs to achieve new, or improved, therapeutic activities.

Monoclonal antibodies or antigen-binding fragments thereof encompassed by the present disclosure that "compete" with the molecules disclosed herein are those that bind human CD47 at site(s) that are identical to, or overlapping with, the site(s) at which the present molecules bind. Competing monoclonal antibodies or antigen-binding fragments thereof can be identified, for example, via an antibody competition assay. For example, a sample of purified or partially purified human CD47 extracellular domain can be bound to a solid support. Then, an antibody compound, or antigen binding fragment thereof, of the present disclosure and a monoclonal antibody or antigen-binding fragment thereof suspected of being able to compete with such disclosure antibody compound are added. One of the two molecules is labeled. If the labeled compound and the unlabeled compound bind to separate and discrete sites on CD47, the labeled compound will bind to the same level whether or not the suspected competing compound is present. However, if the sites of interaction are identical or overlapping, the unlabeled compound will compete, and the amount of labeled compound bound to the antigen will be lowered. If the unlabeled compound is present in excess, very little, if any, labeled compound will bind. For purposes of the present disclosure, competing monoclonal antibodies or antigen-binding fragments thereof are those that decrease the binding of the present antibody compounds to CD47 by about 50%, about 60%, about 70%, about 80%, about 85%, about 86%, about 87%, about 88%, about 89%, about 90%, about 91%, about 92%, about 93%, about 94%, about 95%, about 96%, about 97%, about 98%, or about 99%. Details of procedures for carrying out such competition assays are well known in the art and can be found, for example, in Harlow and Lane (1988) *Antibodies, A Laboratory Manual*, Cold Spring Harbor Laboratory Press, Cold Spring Harbor, N.Y. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared.

Whether mAbs or antigen-binding fragments thereof that compete with antibody compounds of the present disclosure in such competition assays possess the same or similar functional properties of the present antibody compounds can be determined via these methods in conjunction with the methods described in Examples 3-5, below. In various embodiments, competing antibodies for use in the therapeutic methods encompassed herein possess biological activities as described herein in the range of from about 50% to about 100% or about 125%, or more, compared to that of the antibody compounds disclosed herein. In some embodiments, competing antibodies possess about 50%, about 60%, about 70%, about 80%, about 85%, about 90%, about 91%, about 92%, about 93%, about 94%, about 95%, about 96%, about 97%, about 98%, about 99%, or identical biological activity compared to that of the antibody compounds disclosed herein as determined by the methods disclosed in the Examples presented below.

The mAbs or antigen-binding fragments thereof, or competing antibodies useful in the compositions and methods can be any of the isotypes described herein. Furthermore, any of these isotypes can comprise further amino acid modifications as follows.

The monoclonal antibody or antigen-binding fragment thereof, or competing antibody described herein can be of the human IgG1 isotype.

The human IgG1 constant region of the monoclonal antibody, antigen-binding fragment thereof, or competing antibody described herein can be modified to alter antibody half-life. Antibody half-life is regulated in large part by Fc-dependent interactions with the neonatal Fc receptor (Roopenian and Alikesh, 2007). The human IgG1 constant region of the monoclonal antibody, antigen-binding fragment thereof, or competing antibody can be modified to increase half-life include, but are not limited to amino acid modifications N434A, T307A/E380A/N434A (Petkova et al., 2006, Yeung et al., 2009); M252Y/S254T/T256E (Dall'Acqua et al., 2006); T250Q/M428L (Hinton et al., 2006); and M428L/N434S (Zalevsky et al., 2010).

As opposed to increasing half-life, there are some circumstances where decreased half-life would be desired, such as to reduce the possibility of adverse events associated with high Antibody-Dependent Cellular Cytotoxicity (ADCC) and Complement-Dependent Cytotoxicity (CDC) antibodies (Presta 2008). The human IgG1 constant region of the monoclonal antibody, antigen-binding fragment thereof, or competing antibody described herein can be modified to decrease half-life and/or decrease endogenous IgG include, but are not limited to amino acid modifications I253A (Petkova et al., 2006); P257I/N434H, D376V/N434H (Datta-Mannan et al., 2007); and M252Y/S254T/T256E/H433K/N434F (Vaccaro et al., 2005).

The human IgG1 constant region of the monoclonal antibody, antigen-binding fragment thereof, or competing antibody described herein can be modified to increase or decrease antibody effector functions. These antibody effector functions include, but are not limited to, Antibody- Dependent Cellular Cytotoxicity (ADCC), Complement-Dependent Cytotoxicity (CDC), Antibody-Dependent Cellular Phagocytosis (ADCP), C1q binding, and altered binding to Fc receptors.

The human IgG1 constant region of the monoclonal antibody, antigen-binding fragment thereof, or competing antibody described herein can be modified to increase antibody effector function include, but are not limited to amino acid modifications S298A/E333A/K334 (Shields et al., 2001); S239D/I332E and S239D/A330L/I332E (Lazar et al., 2006); F234L/R292P/Y300L, F234L/R292P/Y300L/P393L, and F243L/R292P/Y300L/V305I/P396L (Stevenhagen et al., 2007); G236A, G236A/S239D/I332E, and G236A/S239D/A330L/I332E (Richards et al., 2008); K326A/E333A, K326A/E333S and K326W/E333S (Idusogie et al., 2001); S267E and S267E/L328F (Smith et al., 2012); H268F/S324T, S267E/H268F, S267E/S234T, and S267E/H268F/S324T (Moore et al., 2010); S298G/T299A (Sazinsky et al., 2008); E382V/M428I (Jung et al., 2010).

The human IgG1 constant region of the monoclonal antibody, antigen-binding fragment thereof, or competing antibody described herein can be modified to decrease antibody effector function include, but are not limited to amino acid modifications N297A and N297Q (Bolt et al., 1993, Walker et al., 1989); L234A/L235A (Xu et al., 2000); K214T/E233P/L234V/L235A/G236-deleted/A327G/P331A/D356E/L358M (Ghevaert et al., 2008); C226S/C229S/E233P/L234V/L235A (McEarchern et al., 2007); S267E/L328F (Chu et al., 2008).

The human IgG1 constant region of the monoclonal antibody, antigen-binding fragment thereof, or competing antibody described herein can be modified to decrease antibody effector function include, but are not limited to amino acid modifications V234A/G237A (Cole et al., 1999); E233D, G237D, P238D, H268Q, H268D, P271G, V309L, A330S, A330R, P331S, H268Q/A330S/V309L/P331S, H268D/A330S/V309L/P331S, H268Q/A330R/V309L/P331S, H268D/A330R/V309L/P331S, E233D/A330R, E233D/A330S, E233D/P271G/A330R, E233D/P271G/A330S, G237D/H268D/P271G, G237D/H268Q/P271G, G237D/P271G/A330R, G237D/P271G/A330S, E233D/H268D/P271G/A330R, E233D/H268Q/P271G/A330R, E233D/H268D/P271G/A330S, E233D/H268Q/P271G/A330S, G237D/H268D/P271G/A330R, G237D/H268Q/P271G/A330R, G237D/H268D/P271G/A330S, G237D/H268Q/P271G/A330S, E233D/G237D/H268D/P271G/A330R, E233D/G237D/H268Q/P271G/A330R, E233D/G237D/H268D/P271G/A330S, E233D/G237D/H268Q/P271G/A330S, P238D/E233D/A330R, P238D/E233D/A330S, P238D/E233D/P271G/A330R, P238D/E233D/P271G/A330S, P238D/G237D/H268D/P271G, P238D/G237D/H268Q/P271G, P238D/G237D/P271G/A330R, P238D/G237D/P271G/A330S, P238D/E233D/H268D/P271G/A330R, P238D/E233D/H268Q/P271G/A330R, P238D/E233D/H268D/P271G/A330S, P238D/E233D/H268Q/P271G/A330S, P238D/G237D/H268D/P271G/A330R, P238D/G237D/H268Q/P271G/A330R, P238D/G237D/H268D/P271G/A330S, P238D/G237D/H268Q/P271G/A330S, P238D/E233D/G237D/H268D/P271G/A330R, P238D/E233D/G237D/H268Q/P271G/A330R, P238D/E233D/G237D/H268D/P271G/A330S, P238D/E233D/G237D/H268Q/P271G/A330S (An et al., 2009, Mimoto, 2013).

The monoclonal antibody or antigen-binding fragment thereof, or competing antibody described herein can be of the human IgG2 isotype.

The human IgG2 constant region of the monoclonal antibody, antigen-binding fragment thereof, or competing antibody described herein can be modified to increase or decrease antibody effector functions. These antibody effector functions include, but are not limited to, Antibody-Dependent Cellular Cytotoxicity (ADCC), Complement-Dependent Cytotoxicity (CDC), Antibody-Dependent Cellular Phagocytosis (ADCP), and C1q binding, and altered binding to Fc receptors.

The human IgG2 constant region of the monoclonal antibody, antigen-binding fragment thereof, or competing antibody described herein can be modified to increase antibody effector function include, but are not limited to the amino acid modification K326A/E333S (Idusogie et al., 2001).

The human IgG2 constant region of the monoclonal antibody, antigen-binding fragment thereof, or competing antibody described herein can be modified to decrease antibody effector function include, but are not limited to amino acid modifications V234A/G237A (Cole et al., 1999); E233D, G237D, P238D, H268Q, H268D, P271G, V309L, A330S, A330R, P331S, H268Q/A330S/V309L/P331S, H268D/A330S/V309L/P331S, H268Q/A330R/V309L/P331S, H268D/A330R/V309L/P331S, E233D/A330R, E233D/A330S, E233D/P271G/A330R, E233D/P271G/A330S, G237D/H268D/P271G, G237D/H268Q/P271G, G237D/P271G/A330R, G237D/P271G/A330S, E233D/H268D/P271G/A330R, E233D/H268Q/P271G/A330R, E233D/H268D/P271G/A330S, E233D/H268Q/P271G/A330S, G237D/H268D/P271G/A330R, G237D/H268Q/P271G/A330R, G237D/H268D/P271G/A330S, G237D/H268Q/P271G/A330S, E233D/G237D/H268D/P271G/A330R, E233D/G237D/H268Q/P271G/A330R, E233D/G237D/H268D/P271G/A330S, E233D/G237D/H268Q/P271G/A330S, P238D/E233D/A330R, P238D/E233D/A330S, P238D/E233D/P271G/A330R, P238D/E233D/P271G/A330S, P238D/G237D/H268D/P271G, P238D/G237D/H268Q/P271G, P238D/G237D/P271G/A330R, P238D/G237D/P271G/A330S, P238D/E233D/H268D/P271G/A330R, P238D/E233D/H268Q/P271G/A330R, P238D/E233D/H268D/P271G/A330S, P238D/E233D/H268Q/P271G/A330S, P238D/G237D/H268D/P271G/A330R, P238D/G237D/H268Q/P271G/A330R, P238D/G237D/H268D/P271G/A330S, P238D/G237D/H268Q/P271G/A330S, P238D/E233D/G237D/H268D/P271G/A330R, P238D/E233D/G237D/H268Q/P271G/A330R, P238D/E233D/G237D/H268D/P271G/A330S, P238D/E233D/G237D/H268Q/P271G/A330S (An et al., 2009, Mimoto, 2013).

The Fc region of a human IgG2 of the monoclonal antibody, antigen-binding fragment thereof, or competing antibody described herein can be modified to alter isoform and/or agonistic activity, include, but are not limited to amino acid modifications C127S ($C_{H1}$ domain), C232S, C233S, C232S/C233S, C236S, and C239S (White et al., 2015, Lightle et al., 2010).

The monoclonal antibody or antigen-binding fragment thereof, or competing antibody described herein can be of the human IgG3 isotype.

The human IgG3 constant region of the monoclonal antibody, or antigen binding fragment thereof, wherein said human IgG3 constant region of the monoclonal antibody, or antigen-binding fragment thereof can be modified at one or more amino acid(s) to increase antibody half-life, Antibody-Dependent Cellular Cytotoxicity (ADCC), Complement-Dependent Cytotoxicity (CDC), or apoptosis activity.

The human IgG3 constant region of the monoclonal antibody, or antigen-binding fragment thereof, wherein said human IgG3 constant region of the monoclonal antibody, or antigen-binding fragment thereof can be modified at amino acid R435H to increase antibody half-life.

The monoclonal antibody or antigen-binding fragment thereof, or competing antibody described herein can be of the human IgG4 isotype.

The human IgG4 constant region of the monoclonal antibody, antigen-binding fragment thereof, or competing antibody described herein can be modified to decrease antibody effector functions. These antibody effector functions include, but are not limited to, Antibody-Dependent Cellular Cytotoxicity (ADCC) and Antibody-Dependent Cellular Phagocytosis (ADCP).

The human IgG4 constant region of the monoclonal antibody, antigen-binding fragment thereof, or competing antibody described herein can be modified to prevent Fab arm exchange and/or decrease antibody effector function include, but are not limited to amino acid modifications F234A/L235A (Alegre et al., 1994); S228P, L235E and S228P/L235E (Reddy et al., 2000).

As used herein, the term "tumor" refers to all neoplastic cell growth and proliferation, whether malignant or benign, and all pre-cancerous and cancerous cells and tissues.

The terms "cancer", "cancerous", and "tumor" are not mutually exclusive as used herein. The terms "cancer" and "cancerous" refer to or describe the physiological condition in mammals that is typically characterized by aberrant cell growth/proliferation. Examples of cancers include, but are not limited to, carcinoma, lymphoma (i.e., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "susceptible cancer" as used herein refers to a cancer, cells of which express CD47, and are responsive to treatment with an antibody or antigen binding fragment thereof, or competing antibody or antigen binding fragment thereof, of the present disclosure.

The term "autoimmune disease" as used herein refers to when the body's immune system turns against itself and mistakenly attacks healthy cells.

The term "inflammatory disease" as used herein refers to a disease characterized by inflammation which is a fundamental pathologic process consisting of a dynamic complex of histologically apparent cytologic changes, cellular infiltration, and mediator release that occurs in the affected blood vessels and adjacent tissues in response to an injury or abnormal stimulation caused by a physical, chemical, or biologic agent, including the local reactions and resulting morphologic changes; the destruction or removal of the injurious material; and the responses that lead to repair and healing.

The term "autoinflammatory disease" as used herein refers to a disease that results when the innate immune system causes inflammation for unknown reasons.

As used herein, the term "ischemia" refers to a vascular phenomenon in which a decrease in the blood supply to a bodily organ, tissue, or part is caused, for instance, by constriction or obstruction of one or more blood vessels. Ischemia sometimes results from vasoconstriction or thrombosis or embolism. Ischemia can lead to direct ischemic injury, tissue damage due to cell death caused by reduced oxygen supply. Ischemia can occur acutely, as during surgery, or from trauma to tissue incurred in accidents, injuries and war settings, or following harvest of organs intended for subsequent transplantation, for example. It can also occur sub-acutely, as found in atherosclerotic peripheral vascular disease, where progressive narrowing of blood vessels leads to inadequate blood flow to tissues and organs. When a tissue is subjected to ischemia, a sequence of chemical events is initiated that may ultimately lead to cellular dysfunction and necrosis. If ischemia is ended by the restoration of blood flow, a second series of injurious events ensue, producing additional injury. Thus, whenever there is a transient decrease or interruption of blood flow in a subject, the resultant injury involves two components—the direct injury occurring during the ischemic interval, and the indirect or reperfusion injury that follows.

"Ischemic stroke" can be caused by several different kinds of diseases. The most common problem is narrowing of the arteries in the neck or head. This is most often caused by atherosclerosis, or gradual cholesterol deposition. If the arteries become too narrow, blood cells may collect in them and form blood clots (thrombi). These blood clots can block the artery where they are formed (thrombosis), or can dislodge and become trapped in arteries closer to the brain (embolism). Cerebral stroke can occur when atherosclerotic plaque separates away partially from the vessel wall and occludes the flow of blood through the blood vessel.

As used herein, the term "Reperfusion" refers to restoration of blood flow to tissue that is ischemic, due to decrease in blood flow. Reperfusion is a procedure for treating infarction or other ischemia, by enabling viable ischemic tissue to recover, thus limiting further necrosis. However, reperfusion can itself further damage the ischemic tissue, causing reperfusion injury. In addition to the immediate injury that occurs during deprivation of blood flow, "ischemic/reperfusion injury" involves tissue injury that occurs after blood flow is restored. Current understanding is that much of this injury is caused by chemical products, free radicals, and active biological agents released by the ischemic tissues.

"Nitric oxide (NO) donor, precursor, or nitric oxide generating topical agent" refers to a compound or agent that either delivers NO, or that can be converted to NO through enzymatic or non-enzymatic processes. Examples include, but are not limited to, NO gas, isosorbide dinitrite, nitrite, nitroprus side, nitroglycerin, 3-Morpholinosydnonimine (SIN-1), S-nitroso-N-acetyl-penicillamine (SNAP), Diethylenetriamine/NO (DETA/NO), S-nitrosothiols, Bidil®, and arginine.

"Soluble guanylyl cyclase (sGC)" is the receptor for nitric oxide in vascular smooth muscle. In the cardiovascular system, nitric oxide is endogenously generated by endothelial nitric oxide synthase from L-arginine, and activates soluble guanylyl cyclase in adjacent vascular smooth muscle cells to increase cGMP levels, inducing vascular relaxation. Nitric oxide binds to the normally reduced heme moiety of soluble guanylyl cyclase, and increases the formation of cGMP from GTP, leading to a decrease in intracellular calcium, vasodilation, and anti-inflammatory effects. Oxidation of the heme iron on sGC decreases responsiveness of the enzyme to nitric oxide, and promotes vasoconstriction. The nitric oxide-sGC-cGMP pathway therefore plays an important role in cardiovascular diseases. Nitrogen-containing compounds such as sodium azide, sodium nitrite, hydroxylamine, nitroglycerin, and sodium nitroprusside have been shown to stimulate sGC, causing an increase in cGMP, and vascular relaxation. In contrast to stimulators of sGC, which bind to reduced sGC, activators of sGC activate the oxidized or heme-deficient sGC enzyme that is not responsive to nitric oxide, i.e., they stimulate sGC independent of redox state. While stimulators of sGC can enhance the sensitivity of reduced sGC to nitric oxide, activators of sGC can increase sGC enzyme activity even when the enzyme is oxidized and is therefore less, or unresponsive, to nitric oxide. Thus, sGC activators are non-nitric oxide based. Note the reviews of Nossaman et al. (2012) *Critical Care Research and Practice*, Volume 2012, article 290805, and Derbyshire and Marletta (2012) *Ann. Rev. Biochem.* 81:533-559.

"An agent that activates soluble guanylyl cyclase" refers, for example, to organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marletta (2012) *Ann. Rev. Biochem.* 81:533-559, and Nossaman et al. (2012) *Critical Care Research and Practice*, Volume 2012, Article ID 290805, pages 1-12.

cGMP can also be increased by inhibiting degradation using phosphodiesterase inhibitors. Examples of "an agent that inhibits cyclic nucleotide phosphodiesterases" include, tadalafil, vardenafil, udenafil, and sildenafil avanafil.

As used herein, term "treating" or "treat" or "treatment" means slowing, interrupting, arresting, controlling, stopping, reducing, or reversing the progression or severity of a sign, symptom, disorder, condition, or disease, but does not necessarily involve a total elimination of all disease-related signs, symptoms, conditions, or disorders. The term "treating" and the like refer to a therapeutic intervention that ameliorates a sign or symptom of a disease or pathological condition after it has begun to develop.

As used herein, term "effective amount" refers to the amount or dose of an antibody compound of the present disclosure which, upon single or multiple dose administration to a patient or organ, provides the desired treatment or prevention.

The precise effective amount for any particular subject will depend upon their size and health, the nature and extent of their condition, and the therapeutics or combination of therapeutics selected for administration. The effective amount for a given patient is determined by routine experimentation and is within the judgment of a clinician. Therapeutically effective amounts of the present antibody compounds can also comprise an amount in the range of from about 0.1 mg/kg to about 150 mg/kg, from about 0.1 mg/kg to about 100 mg/kg, from about 0.1 mg/kg to about 50 mg/kg, or from about 0.05 mg/kg to about 10 mg/kg per single dose administered to a harvested organ or to a patient. Known antibody-based pharmaceuticals provide guidance in this respect. For example, Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; for example.

A therapeutically effective amount for any individual patient can be determined by the health care provider by monitoring the effect of the antibody compounds on tumor regression, circulating tumor cells, tumor stem cells or anti-tumor responses. Analysis of the data obtained by these methods permits modification of the treatment regimen during therapy so that optimal amounts of antibody compounds of the present disclosure, whether employed alone or in combination with one another, or in combination with another therapeutic agent, or both, are administered, and so that the duration of treatment can be determined as well. In this way, the dosing/treatment regimen can be modified over the course of therapy so that the lowest amounts of antibody compounds used alone or in combination that exhibit satisfactory efficacy are administered, and so that administration of such compounds is continued only so long as is necessary to successfully treat the patient. Known antibody-based pharmaceuticals provide guidance relating to frequency of administration e.g., whether a pharmaceutical should be delivered daily, weekly, monthly, etc. Frequency and dosage may also depend on the severity of symptoms.

In some embodiments antibody compounds of the present disclosure can be used as medicaments in human and veterinary medicine, administered by a variety of routes including, but not limited to, oral, intravenous, intramuscular, intra-arterial, intramedullary, intraperitoneal, intrathecal, intraventricular, transdermal, transcutaneous, topical, subcutaneous, intratumoral, intranasal, enteral, sublingual, intravaginal, intravesicular or rectal routes. The compositions can also be administered directly into a lesion such as a tumor. Dosage treatment may be a single dose schedule or a multiple dose schedule. Hypo sprays may also be used to administer the pharmaceutical compositions. Typically, the therapeutic compositions can be prepared as injectables, either as liquid solutions or suspensions. Solid forms suitable for solution in, or suspension in, liquid vehicles prior to injection can also be prepared. Veterinary applications include the treatment of companion/pet animals, such as cats and dogs; working animals, such as guide or service dogs, and horses; sport animals, such as horses and dogs; zoo animals, such as primates, cats such as lions and tigers, bears, etc.; and other valuable animals kept in captivity.

Such pharmaceutical compositions can be prepared by methods well known in the art. See, e.g., *Remington: The Science and Practice of Pharmacy*, 21$^{st}$ Edition (2005), Lippincott Williams & Wilkins, Philadelphia, Pa., and comprise one or more antibody compounds disclosed herein, and a pharmaceutically or veterinarily acceptable, for example, physiologically acceptable, carrier, diluent, or excipient. The present disclosure describes anti-CD47 mAbs with distinct functional profiles. These antibodies possess distinct combinations of properties selected from the following: 1) exhibit cross-reactivity with one or more species homologs of CD47; 2) block the interaction between CD47 and its ligand SIRPα; 3) increase phagocytosis of human tumor cells, 4) induce death of susceptible human tumor cells; 5) do not induce cell death of human tumor cells; 6) have reduced binding to human red blood cells (hRBCs); 7) have no detectable binding to hRBCs; 8) cause reduced agglutination of hRBCs; 9) cause no detectable agglutination of hRBCs; 10) reverse TSP1 inhibition of the nitric oxide (NO) pathway and/or 11) do not reverse TSP1 inhibition of the NO pathway.

The anti-CD47 antibodies and antigen binding fragments thereof of the present disclosure possess combinations of properties that are distinct from the anti-CD47 antibodies of the prior art. These properties and characteristics will now be described in further detail.

Binding to CD47 of Different Species

The anti-CD47 antibodies, and antigen binding fragments thereof, of the present disclosure bind human CD47. In certain embodiments, the anti-CD47 antibodies exhibit cross-reactivity with one or more species homologs of CD47, for example CD47 homologs of non-human primate origin. In certain embodiments, the anti-CD47 antibodies and antigen binding fragments thereof of the present disclosure bind to human CD47 and to CD47 of non-human primate, mouse, rat, and/or rabbit origin. The cross-reactivity with other species homologs can be particularly advantageous in the development and testing of therapeutic antibodies. For example, pre-clinical toxicology testing of therapeutic antibodies is frequently carried out in non-human primate species including, but not limited to, cynomolgus monkey, green monkey, rhesus monkey and squirrel monkey. Cross-reactivity with these species homologs can therefore be particularly advantageous for the development of antibodies as clinical candidates.

Blocking the Interaction Between CD47 and SIRPα and Promoting Phagocytosis

CD47, also known as integrin associated protein (IAP), is a 50 kDa cell surface receptor that is comprised of an extracellular N-terminal IgV domain, a five membrane spanning transmembrane domain, and a short C-terminal intracellular tail that is alternatively spliced.

Two ligands bind to CD47: Signal Regulatory Protein alpha (SIRPα) and Thrombospondin-1 (TSP1). TSP1 is present in plasma and synthesized by many cells, including platelets. SIRPα is expressed on hematopoietic cells, which include macrophages and dendritic cells.

When SIRPα on a phagocyte engages CD47 on a target cell, this interaction prevents phagocytosis of the target cell. The interaction of CD47 and SIRPα effectively sends a "don't eat me" signal to the phagocyte (Oldenborg et al. *Science* 288: 2051-2054, 2000). Blocking the interaction of SIRPα and CD47 with an anti-CD47 mAb in a therapeutic context can provide an effective anti-cancer treatment by promoting the uptake and clearance of cancer cells by the host's immune system. Thus, an important functional characteristic of some anti-CD47 mAbs is the ability to block the interaction of CD47 and SIRPα, resulting in phagocytosis of CD47 expressing tumor cells by macrophages. Several anti-CD47 mAbs have been shown to block the interaction of CD47 and SIRPα, including B6H12 (Seiffert et al. *Blood* 94:3633-3643, 1999; Latour et al. *J. Immunol.* 167: 2547-2554, 2001; Subramanian et al. *Blood* 107: 2548-2556, 2006; Liu et al. *J Biol. Chem.* 277: 10028-10036, 2002; Rebres et al et al. *J. Cellular Physiol.* 205: 182-193, 2005), BRIC126 (Vernon-Wilson et al. *Eur J Immunol.* 30: 2130-2137, 2000; Subramanian et al. *Blood* 107: 2548-2556, 2006), CC2C6 (Seiffert et al. *Blood* 94:3633-3643, 1999), and 1F7 (Rebres et al. *J. Cellular Physiol.* 205: 182-193, 2005). B6H12 and BRIC126 have also been shown to cause phagocytosis of human tumor cells by human and mouse macrophages (Willingham et al. *Proc Natl Acad Sci USA* 109(17):6662-6667, 2012; Chao et al. *Cell* 142:699-713, 2012; EP 2 242 512 B1). Other existing anti-CD47 mAbs, such as 2D3, does not block the interaction of CD47 and SIRPα (Seiffert et al. *Blood* 94:3633-3643, 1999; Latour et al. *J. Immunol.* 167: 2547-2554, 2001; Rebres et al. *J. Cellular Physiol.* 205: 182-193, 2005), and does not cause phagocytosis of tumor cells (Willingham et al. *Proc Natl Acad Sci USA* 109(17):6662-6667, 2012; Chao et al. *Cell* 142:699-713, 2012; EP 2 242 512 B1).

As used herein, the term "blocks SIRPα binding to human CD47" refers to a greater than 50% reduction of SIRPα-Fc binding to CD47 on Jurkat cells by an anti-CD47 mAb.

The anti-CD47 mAbs of the disclosure described herein, block the interaction of CD47 and SIRPα and increase phagocytosis of human tumor cells.

"Phagocytosis" of cancer cells refers to the engulfment and digestion of such cells by macrophages, and the eventual digestion or degradation of these cancer cells and the release of digested or degraded cellular components extracellularly, or intracellularly to undergo further processing. Anti-CD47 monoclonal antibodies that block SIRPα binding to CD47 increase macrophage phagocytosis of cancer cells. SIRPα binding to CD47 on cancer cells would otherwise allow these cells to escape macrophage phagocytosis. The cancer cell may be viable or living cancer cells.

Inducing Death of Tumor Cells

Some soluble anti-CD47 mAbs initiate a cell death program on binding to CD47 on tumor cells, resulting in collapse of mitochondrial membrane potential, loss of ATP generating capacity, increased cell surface expression of phosphatidylserine (detected by increased staining for annexin V) and cell death without the participation of caspases or fragmentation of DNA. Such soluble anti-CD47 mAbs have the potential to treat a variety of solid and hematological cancers. Several soluble anti-CD47 mAbs which have been shown to induce tumor cell death, including MABL-1, MABL-2 and fragments thereof (U.S. Pat. No. 8,101,719; Uno et al. *Oncol Rep.* 17: 1189-94, 2007; Kikuchi et al. *Biochem Biophys Res. Commun.* 315: 912-8, 2004), Ad22 (Pettersen et al. *J. Immuno.* 166: 4931-4942, 2001; Lamy et al. *J. Biol. Chem.* 278: 23915-23921, 2003), and 1F7 (Manna et al. *J. Immunol.* 170: 3544-3553, 2003; Manna et al. *Cancer Research*, 64: 1026-1036, 2004). Some of the anti-CD47 mAbs of the disclosure described herein induce cell death of human tumor cells.

The terms "inducing cell death" or "kills" and the like, are used interchangeably herein to mean that addition of an antibody compound of the present disclosure to cultured cancer cells causes these cells to display quantifiable characteristics associated with cell death including any one, or more, of the following:

1. Increased binding of Annexin V (in the presence of calcium ion) to the tumor cells as detected by flow cytometry or confocal fluorescence microscopy;

2. Increased uptake of the fluorescent compound propidium iodide (as assayed by flow cytometry) or 7-aminoactinomycin D (7-AAD as assayed by flow cytometry) or trypan blue (scored with light microscopy) by the tumor cells 3. Loss of mitochondrial function and membrane potential by the tumor cells as assayed by one of several available measures (potentiometric fluorescent dyes such as DiO-C6 or JC1 or formazan-based assays such as MTT or WST-1).

Induction of cell death refers to the ability of certain of the soluble anti-CD47 antibodies, murine antibodies, chimeric antibodies, humanized antibodies, or antigen-binding fragments thereof (and competing antibodies and antigen-binding fragments thereof) disclosed herein to kill cancer cells via a cell autonomous mechanism without participation of complement or other cells including, but not limited to, T cells, neutrophils, natural killer cells, macrophages, or dendritic cells. Quantifiably, induction of cell death includes, but is not limited to, a greater than 2-fold increase in annexin V staining of human tumor cells caused by soluble anti-CD47 mAb compared to the background obtained with the negative control antibody (humanized, isotype-matched antibody).

Among the present humanized or chimeric mAbs, those that induce cell death of human tumor cells cause increased Annexin V binding similar to the findings reported for anti-CD47 mAbs Ad22 (Pettersen et al. *J. Immuno.* 166: 4931-4942, 2001; Lamy et al. *J. Biol. Chem.* 278: 23915-23921, 2003); 1F7 (Manna and Frazier *J. Immunol.* 170: 3544-3553, 2003; *Manna and Frazier Cancer Res.* 64:1026-1036, 2004); and MABL-1 and 2 (U.S. Pat. No. 7,531,643 B2; U.S. Pat. No. 7,696,325 B2; U.S. Pat. No. 8,101,719 B2).

Cell viability assays are described in NCI/NIH guidance manual that describes numerous types of cell based assays that can be used to assess induction of cell death caused by CD47 antibodies: "Cell Viability Assays", Terry L Riss, PhD, Richard A Moravec, B S, Andrew L Niles, M S, Helene A Benink, PhD, Tracy J Worzella, M S, and Lisa Minor, PhD. Contributor Information, published May 1, 2013.

Binding to hRBCs

CD47 is expressed on human erythrocytes (hRBCs) (Brown. *J Cell Biol.* 111: 2785-2794, 1990; Avent. *Biochem J.*, (1988) 251: 499-505; Knapp. Blood, (1989) Vol. 74, No. 4, 1448-1450; Oliveira et al. *Biochimica et Biophysica Acta* 1818: 481-490, 2012; Petrova P. et al. *Cancer Res* 2015; 75(15 Suppl): Abstract nr 4271). It has been shown that anti-CD47 mAbs bind to RBCs, including B6H12 (Brown et al. *J. Cell Biol.*, 1990, Oliveira et al. *Biochimica et Biophysica Acta* 1818: 481-490, 2012, Petrova P. et al. *Cancer Res* 2015; 75(15 Suppl): Abstract nr 4271), BRIC125 (Avent. *Biochem J.*, (1988) 251: 499-505), BRIC126 (Avent. *Biochem J.*, (1988) 251: 499-505; Petrova P. et al. *Cancer Res* 2015; 75(15 Suppl): Abstract nr 4271), 5F9 (Uger R. et al. *Cancer Res* 2014; 74(19 Suppl): Abstract nr 5011, Liu et al. *PLoS One.* 2015 Sep. 21; 10(9): e0137345; Sikic B. et al. *J Clin Oncol* 2016; 34 (suppl; abstract 3019)), anti-CD47 antibodies disclosed in US Patent Publication 2014/0161799, WO Publication 2014/093678, US Patent Publication 2014/0363442, and CC2C6 (Petrova P. et al. *Cancer Res* 2015; 75(15 Suppl): Abstract nr 4271, Uger R. et al. *Cancer Res* 2014; 74(19 Suppl): Abstract nr 5011). It has also been shown that a SIRPα-Fc fusion protein, which binds to human CD47, has reduced binding to human RBCs compared to other human cells (Uger R. et al. *Cancer Res* 2014; 74(19 Suppl): Abstract nr 5011). Binding to RBCs can be reduced by generation of bi-specific antibodies with only one CD47 binding arm (Masternak et al. *Cancer Res* 2015; 75(15 Suppl): Abstract nr 2482).

Because some anti-CD47 mAbs have been shown to result in reduction of RBCs when administered to cynomolgus monkeys (Mounho-Zamora B. et al. *The Toxicologist, Supplement to Toxicological Sciences,* 2015; 144 (1): Abstract 596: 127, Liu et al. *PLoS One.* 2015 Sep. 21; 10(9): e0137345; Pietsch et al. *Cancer Res* 2015; 75(15 Suppl): Abstract nr 2470), it is highly desirable to identify anti-CD47 mAbs that do not bind to CD47-expressing RBCs.

As used herein, the terms "red blood cell(s)" and "erythrocyte(s)" are synonymous and used interchangeably herein.

As used herein, the terms "reduced binding to hRBCs", refers to the $K_d$ of an anti-CD47 mAb binding to a hRBC which is 10-fold or greater than the Kd on a human tumor cell, wherein the tumor cell is an OV10hCD47 cell.

As used herein, the term "no binding" or "NB", refers to no measurable binding to hRBCs at an anti-CD47 mAb concentration up to and including 100 µg/ml.

Prior to the disclosure described herein, no anti-CD47 mAbs have been reported that do not bind to human RBCs expressing CD47.

Some of the anti-CD47 mAbs, disclosed herein, have reduced or no detectable binding to human RBCs.

Agglutination of RBCs

Red blood cell (RBC) agglutination or hemagglutination is a homotypic interaction that occurs when RBCs aggregate or clump together following incubation with various agents, including antibodies to RBC antigens and cell surface proteins such as CD47. Many anti-CD47 antibodies have been reported to cause hemagglutination of isolated human RBCs in vitro, in a concentration dependent manner, including B6H12, BRIC126, MABL-1, MABL-2, CC2C6, and 5F9 (Uger R. et al. *Cancer Res* 2014; 74(19 Suppl): Abstract nr 5011, U.S. Pat. No. 9,045,541, Uno et al. *Oncol Rep.* 17: 1189-94, 2007; Kikuchi et al. *Biochem Biophys Res. Commun.* 315: 912-8, 2004; Sikic B. et al. *J Clin Oncol* 2016; 34 (suppl; abstract 3019)). This functional effect requires binding to RBCs by an intact, bivalent antibody and can be reduced or eliminated by generating antibody fragments, either a F(ab') or svFv (Uno et al. *Oncol Rep.* 17: 1189-94, 2007; Kikuchi et al. *Biochem Biophys Res. Commun.* 315: 912-8, 2004) or bi-specific antibodies with only one CD47 binding arm (Masternak et al. *Cancer Res* 2015; 75(15 Suppl): Abstract nr 2482). Other functional properties of these fragments, including cell killing, were shown to be either reduced or retained in these fragments (Uno et al. *Oncol Rep.* 17: 1189-94, 2007; Kikuchi et al. *Biochem Biophys Res. Commun.* 315: 912-8, 2004). The mouse antibody 2D3 is an example of an anti-CD47 antibody that binds to CD47 on red blood cells but does not cause hemagglutination (U.S. Pat. No. 9,045,541, Petrova et al. *Cancer Res* 2015; 75(15 Suppl): Abstract nr 4271). Hemagglutination has been shown to be reduced/eliminated by reducing the binding selectively to human RBCs, but not other cells, using a SIRPα-Fc fusion protein (Uger R. et al. *Blood* 2013; 122(21): 3935). In addition, mouse anti-CD47 mAb 2A1 and humanized versions of 2A1 have been reported to block CD47/SIRPα but do not exhibit hemagglutination activity (U.S. Pat. No. 9,045,541). A small number of a panel of mouse anti-human CD47 antibodies (3 of 23) were reported to not cause hemagglutination of human RBCs (Pietsch E et al. *Cancer Res* 2015; 75(15 Suppl): Abstract nr 2470). Therefore, prior to the disclosure described herein, there was a need to identify CD47 mAbs that block SIRPα/CD47 binding, have no detectable or reduced binding to RBCs and/or cause no hemagglutination. The term "agglutination" refers to cellular clumping, while the term "hemagglutination" refers to clumping of a specific subset of cells, i.e., RBCs. Thus, hemagglutination is a type of agglutination.

As used herein, the term "reduced hemagglutination" refers to measurable agglutination activity of hRBCs at anti-CD47 mAb concentrations greater that 1.85 µg/ml, and no measurable activity at concentrations less than or equal to 1.85 µg/ml.

As used herein, the term "no detectable hemagglutination", refers to no measurable agglutination activity of hRBCs at anti-CD47 mAb concentrations greater or equal to 0.3 pg/mL to a concentration less than or equal to 50 µg/mL.

Some of the anti-CD47 antibodies described herein, cause reduced or no detectable hemagglutination of human RBCs.

Modulation of the NO Pathway

As noted above, TSP1 is also a ligand for CD47. The TSP1/CD47 pathway opposes the beneficial effects of the NO pathway in many cell types, including, but not limited to, vascular cells. The NO pathway consists of any of three enzymes (nitric oxide synthases, NOS I, NOS II and NOS III) that generate bioactive gas NO using arginine as a substrate. NO can act within the cell in which it is produced, or in neighboring cells, to activate the enzyme soluble guanylyl cyclase that produces the messenger molecule cyclic GMP (cGMP). The proper functioning of the NO/cGMP pathway is essential for protecting the cardiovascular system against stresses including, but not limited to, those resulting from wounding, inflammation, hypertension, metabolic syndrome, ischemia, and IRI. In the context of these cellular stresses the inhibition of the NO/cGMP pathway by the TSP1/CD47 system exacerbates the effects of stress. This is a particular problem in the cardiovascular system where both cGMP and cAMP play important protective roles. There are many cases in which ischemia and reperfusion injury cause or contribute to disease, trauma, and poor outcomes of surgical procedures.

As disclosed herein, one of more of the chimeric or humanized anti-CD47 antibodies will reverse TSP1 inhibition of cGMP production. Reversal will be complete (>80%) or intermediate (20%-80%). This reversal of TSP1 inhibition of cGMP production will demonstrate that the anti-CD47 mAbs have the ability to increase NO signaling and suggest utility in protecting the cardiovascular system against stresses including, but not limited to, those resulting from wounding, inflammation, hypertension, metabolic syndrome, ischemia, and ischemia-reperfusion injury (IRI). Additional assay systems, for example smooth muscle cell contraction, will also be expected to show that some of the chimeric or humanized antibodies reverse the inhibitory actions of TSP1 on downstream effects resulting from the activation of NO signaling.

As disclosed herein, "complete reversal of NO pathway inhibition" refers to greater than 80% reversal of TSP1 inhibition of NO signaling by an anti-CD47 mAb compared to a negative control, humanized isotype-matched antibody.

As disclosed herein, "intermediate reversal of NO pathway inhibition" refers to 20-80% reversal of TSP1 inhibition of NO signaling by an anti-CD47 mAb compared to a negative control, humanized isotype-matched antibody.

As disclosed herein, "no reversal of NO pathway inhibition" refers to less than 20% reversal of TSP1 inhibition of NO signaling by an anti-CD47 mAb compared to a negative control, humanized isotype-matched antibody.

Preferred Combinations of Functional Properties

Anti-CD47 mAbs exist in the prior art with combinations of some, but not all, of the functional characteristics described herein. Previously, it has been shown that humanized anti-CD47 mAbs such as AB6.12 IgG1, AB6.12-IgG4P, and AB6.12-IgG4PE (U.S. Pat. No. 9,045,541, US Patent Publication 2014/0161799, WO Publication 2014/093678, US Patent Publication 2014/0363442) and 5F9 (Mounho-Zamora B. et al. *The Toxicologist, Supplement to Toxicological Sciences,* 2015; 144 (1): Abstract 596: 127, Liu et al. *PLoS One.* 2015 Sep. 21; 10(9): e0137345) bind human CD47, block the interaction of CD47 and SIRPα and cause phagocytosis of human tumor cells. The humanized CD47 mAbs AB6.12 IgG1, AB6.12-IgG4P, and AB6.12-IgG4PE also do not cause hemagglutination of human RBCs (U.S. Pat. No. 9,045,541). The 5F9 humanized anti-CD47 mAb binds to and causes hemagglutination of human RBCs (Uger R. et al. *Cancer Res* 2014; 74(19 Suppl): Abstract nr 5011, Sikic B. et al. *J Clin Oncol* 2016; 34 (suppl; abstract 3019). Murine anti-CD47 mAbs B6H12, BRIC126, and CC2C6 block the interaction of CD47 and SIRPα, cause phagocytosis, and bind to and cause hemagglutination of human RBCs (Petrova P. et al. *Cancer Res* 2015; 75(15 Suppl): Abstract nr 4271, Seiffert et al. *Blood* 94:3633-3643, 1999; Vernon-Wilson et al. *Eur J Immunol.* 30: 2130-2137, 2000; Latour et al. *J. Immunol.* 167: 2547-2554, 2001; Subramanian et al. *Blood* 107: 2548-2556, 2006; Liu et al. *J Biol. Chem.* 277: 10028-10036, 2002). Murine anti-CD47 mAbs MABL-1 and MABL-2 bind to human CD47, induce tumor cell death and cause RBC hemagglutination (U.S. Pat. No. 8,101,719); murine mAb Ad22 binds to human CD47 and induces tumor cell death (Pettersen et al. *J. Immunol.* 166: 4931-4942, 2001; Lamy et al. *J Biol Chem.* 278: 23915-23921, 2003); and murine mAb 1F7 binds to human CD47, blocks the interaction of CD47 and SIRPα and induces tumor cell death (Rebres et al. *J. Cellular Physiol.* 205: 182-193, 2005; Manna et al. *J. Immunol.* 170: 3544-3553, 2003; Manna et al. *Cancer Research,* 64: 1026-1036, 2004).

Preferred embodiments of the anti-CD47 antibodies described herein, are also characterized by combinations of properties which are not exhibited by prior art anti-CD47 antibodies proposed for human therapeutic use. Accordingly, the preferred anti-CD47 antibodies described herein are characterized by:
 a. binds to human CD47,
 b. blocks SIRPα binding to human CD47,
 c. increases phagocytosis of human tumor cells; and
 d. induces death of susceptible human tumor cells.

In another preferred embodiment described herein, the anti-CD47 antibodies are characterized by:
 a. binds to human CD47,
 b. blocks SIRPα binding to human CD47,
 c. increases phagocytosis of human tumor cells,
 d. induces death of susceptible human tumor cells; and
 e. causes no agglutination of human red blood cells (hRBCs).

In yet another preferred embodiment described herein, the anti-CD47 antibodies are characterized by:
 a. binds to human CD47,
 b. blocks SIRPα binding to human CD47,
 c. increases phagocytosis of human tumor cells,
 d. induces death of susceptible human tumor cells; and
 e. causes reduced agglutination of human red blood cells (hRBCs).

In another preferred embodiment described herein, the anti-CD47 antibodies are characterized by:
 a. specifically binds to human CD47,
 b. blocks SIRPα binding to human CD47,
 c. increases phagocytosis of human tumor cells
 d. induces death of susceptible human tumor cells; and
 e. has reduced hRBC binding.

In another preferred embodiment described herein, the anti-CD47 antibodies are characterized by:
 a. binds to human CD47,
 b. blocks SIRPα binding to human CD47,
 c. increases phagocytosis of human tumor cells,
 d. causes no agglutination of human red blood cells (hRBCs); and
 e. does not bind to hRBCs.

In another preferred embodiment described herein, the anti-CD47 antibodies are characterized by:
 a. specifically binds to human CD47,
 b. blocks SIRPα binding to human CD47,
 c. increases phagocytosis of human tumor cells,
 d. causes no agglutination of human red blood cells (hRBCs); and
 e. has reduced hRBC binding.

In another preferred embodiment described herein, the monoclonal antibody, or antigen binding fragment thereof also specifically binds to non-human primate CD47, wherein non-human primate may include, but is not limited to, cynomolgus monkey, green monkey, rhesus monkey and squirrel monkey.

In yet another preferred embodiment described herein, the monoclonal antibody, or antigen binding fragment thereof binds human, non-human primate, mouse, rabbit, and rat CD47.

Described herein, are anti-CD47 mAbs with distinct functional profiles. These antibodies possess distinct combinations of properties selected from the following: 1) exhibit cross-reactivity with one or more species homologs of CD47; 2) block the interaction between CD47 and its ligand SIRPα; 3) increase phagocytosis of human tumor cells, 4) induce death of susceptible human tumor cells; 5) do not induce cell death of human tumor cells; 6) have reduced binding to human red blood cells (hRBCs); 7) have no detectable binding to hRBCs; 8) cause reduced agglutination of hRBCs; 9) cause no detectable agglutination of hRBCs; 10) reverse TSP1 inhibition of the nitric oxide (NO) pathway and/or 11) do not reverse TSP1 inhibition of the NO pathway.

CD47 Antibodies

Many human cancers up-regulate cell surface expression of CD47 and those expressing the highest levels of CD47 are appear to be the most aggressive and the most lethal for patients. Increased CD47 expression is thought to protect cancer cells from phagocytic clearance by sending a "don't eat me" signal to macrophages via SIRPα, an inhibitory receptor that prevents phagocytosis of CD47-bearing cells (Oldenborg et al. *Science* 288: 2051-2054, 2000; Jaiswal et al. (2009) *Cell* 138(2):271-851; Chao et al. (2010) *Science Translational Medicine* 2(63):63ra94). Thus, the increase of CD47 expression by many cancers provides them with a cloak of "selfness" that slows their phagocytic clearance by macrophages and dendritic cells.

Antibodies that block CD47 and prevent its binding to SIRPα have shown efficacy in human tumor in murine (xenograft) tumor models. Such blocking anti-CD47 mAbs exhibiting this property increase the phagocytosis of cancer cells by macrophages, which can reduce tumor burden (Majeti et al. (2009) *Cell* 138 (2): 286-99; U.S. Pat. No. 9,045,541; Willingham et al. (2012) *Proc Natl Acad. Sci. USA* 109(17):6662-6667; Xiao et al. (2015) *Cancer Letters* 360:302-309; Chao et al. (2012) *Cell* 142:699-713; Kim et al. (2012) *Leukemia* 26:2538-2545) and may ultimately lead to generation of an adaptive immune response to the tumor (Tseng et al. (2013) *PNAS* 110 (27):11103-11108; Soto-Pantoja et al. (2014) *Cancer Res.* 74 (23): 6771-6783; Liu et al. (2015) *Nat. Med.* 21 (10): 1209-1215).

However, there are mechanisms by which anti-CD47 mAbs can attack transformed cells that have not yet been exploited in the treatment of cancer. Multiple groups have shown that particular anti-human CD47 mAbs induce cell death of human tumor cells. Anti-CD47 mAb Ad22 induces cell death of multiple human tumor cells lines (Pettersen et al. *J. Immuno.* 166: 4931-4942, 2001; Lamy et al. *J. Biol. Chem.* 278: 23915-23921, 2003). AD22 was shown to indice rapid mitochondrial dysfunction and rapid cell death with early phosphatidylserine exposure and a drop in mitochondrial membrane potential (Lamy et al. *J. Biol. Chem.* 278: 23915-23921, 2003). Anti-CD47 mAb MABL-2 and fragments thereof induce cell death of human leukemia cell lines in vitro and had an anti-tumor effect in in vivo xenograft models. (Uno et al. (2007) *Oncol. Rep.* 17 (5): 1189-94). Anti-human CD47 mAb 1F7 induces cell death of human T cell leukemias (Manna and Frazier (2003) *J. Immunol.* 170: 3544-53) and several breast cancers (Manna and Frazier (2004) *Cancer Research* 64 (3):1026-36). 1F7 kills CD47-bearing tumor cells without the action of complement or cell mediated killing by NK cells, T cells, or macrophages. Instead, anti-CD47 mAb 1F7 acts via a non-apoptotic mechanism that involves a direct CD47-dependent attack on mitochondria, discharging their membrane potential and destroying the ATP-generating capacity of the cell leading to rapid cell death. It is noteworthy that anti-CD47 mAb 1F7 does not kill resting leukocytes, which also express CD47, but only those cells that are "activated" by transformation. Thus, normal circulating cells, many of which express CD47, are spared while cancer cells are selectively killed by the tumor-toxic CD47 mAb (Manna and Frazier (2003) *J. Immunol.* 170: 3544-53). This mechanism can be thought of as a proactive, selective and direct attack on tumor cells in contrast to the passive mechanism of causing phagocytosis by simply blocking CD47/SIRPα binding. Importantly, mAb 1F7 also blocks binding of SIRPα to CD47 (Rebres et al et al. *J. Cellular Physiol.* 205: 182-193, 2005) and thus it can act via two mechanisms: (1) direct tumor toxicity, and (2) causing phagocytosis of cancer cells. A single mAb that can accomplish both functions may be superior to one that only blocks CD47/SIRPα binding.

Following periods of tissue ischemia, the initiation of blood flow causes damage referred to as "ischemia-reperfusion injury" or IRI. IRI contributes to poor outcomes in many surgical procedures where IRI occurs due to the necessity to stop blood flow for a period of time, in many forms/causes of trauma in which blood flow is interrupted and later restored by therapeutic intervention and in procedures required for organ transplantation, cardio/pulmonary bypass procedures, reattachment of severed body parts, reconstructive and cosmetic surgeries and other situations involving stopping and restarting blood flow. Ischemia itself causes many physiological changes that, by themselves would eventually lead to cell and tissue necrosis and death. Reperfusion poses its own set of damaging events including generation of reactive oxygen species, thrombosis, inflammation and cytokine mediated damage. The pathways that are limited by the TSP1-CD47 system are precisely those that would be of most benefit in combating the damage of IRI, including the NO pathway. Thus, blocking the TSP1-CD47 pathway, as with the antibodies disclosed herein, will provide more robust functioning of these endogenous protective pathways. Anti-CD47 mAbs have been shown to reduce organ damage in rodent models of renal warm ishchemia (Rogers et al. *J Am Soc Nephrol.* 23: 1538-1550, 2012), liver ischemia-reperfusion injury (Isenberg et al. *Surgery.* 144: 752-761, 2008), renal transplantation (Lin et al. *Transplantation.* 98: 394-401, 2014; Rogers et al. *Kidney Interantional.* 90: 334-347, 2016)) and liver transplantation, including steatotic livers (Xiao et al. *Liver Transpl.* 21: 468-477, 2015; Xiao et al. *Transplantation.* 100: 1480-1489, 2016). In addition, anti-CD47 mAb caused significant reductions of right ventricular systolic pressure and right ventricular hypertrophy in the monocrotaline model of pulmonary arterial hypertension (Bauer et al. *Cardiovasc Res.* 93: 682-693, 2012). Studies in skin flap models have shown that modulation of CD47, including with anti-CD47 mAbs, inhibits TSP1-mediated CD47 signaling. This results in increased activity of the NO pathway, resulting in reduced IRI (Maxhimer et al. *Plast Reconstr Surg.* 124: 1880-1889, 2009; Isenberg et al. *Arterioscler Throm Vasc Biol.* 27: 2582-2588, 2007; Isenberg et al. *Curr Drug Targets.* 9: 833-841, 2008; Isenberg et al. *Ann Surg.* 247: 180-190, 2008)

Anti-CD47 mAbs have also been shown to be efficacious in models of other cardiovascular diseases. In the mouse transverse aortic constriction model of pressure overload left ventricular heart failure, anti-CD47 mAb mitigated cardiac myocyte hypertrophy, decreased left ventricular fibrosis, prevented an increase in left ventricular weight, decreased ventricular stiffness, and normalized changes in the pressure volume loop profile (Sharifi-Sanjani et al. *J Am Heart Assoc.*, 2014). An anti-CD47 mAb ameliorated atherosclerosis in multiple mouse models (Kojima et al. Nature., 2016).

Cancer Indications

Presently disclosed are anti-CD47 mAbs and antigen binding fragments thereof effective as cancer therapeutics which can be administered to patients, preferably parenterally, with susceptible hematologic cancers and solid tumors including, but not limited to, leukemias, including systemic mastocytosis, acute lymphocytic (lymphoblastic) leukemia (ALL), T cell—ALL, acute myeloid leukemia (AML), myelogenous leukemia, chronic lymphocytic leukemia (CLL), chronic myeloid leukemia (CML), myeloproliferative disorder/neoplasm, monocytic cell leukemia, and plasma cell leukemia; multiple myeloma (MM); Waldenstrom's Macroglobulinemia; lymphomas, including histiocytic lymphoma and T cell lymphoma, B cell lymphomas, including Hodgkin's lymphoma and non-Hodgkin's lymphoma, such as low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL; solid tumors, including ovarian cancer, breast cancer, endometrial cancer, colon cancer (colorectal cancer), rectal cancer, bladder cancer, urothelial cancer, lung cancer (non-small cell lung cancer, adenocarcinoma of the lung, squamous cell carcinoma of the lung), bronchial cancer, bone cancer, prostate cancer, pancreatic cancer, gastric cancer, hepatocellular carcinoma (liver cancer, hepatoma), gall bladder cancer, bile duct cancer, esophageal cancer, renal cell carcinoma, thyroid cancer, squamous cell carcinoma of the head and neck (head and neck cancer), testicular cancer, cancer of the endocrine gland, cancer of the adrenal gland, cancer of the pituitary gland, cancer of the skin, cancer of soft tissues, cancer of blood vessels, cancer of brain, cancer of nerves, cancer of eyes, cancer of meninges, cancer of oropharynx, cancer of hypopharynx, cancer of cervix, and cancer of uterus, glioblastoma, meduloblastoma, astrocytoma, glioma, meningioma, gastrinoma, neuroblastoma, myelodysplastic syndrome, and sarcomas including, but not limited to, osteosarcoma, Ewing's sarcoma, leiomyosarcoma, synovial sarcoma, alveolar soft part sarcoma, angiosarcoma, liposarcoma, fibrosarcoma, rhabdomyosarcoma, and chrondrosarcoma; and melanoma.

Treatment of Cancer

As is well known to those of ordinary skill in the art, combination therapies are often employed in cancer treatment as single-agent therapies or procedures may not be sufficient to treat or cure the disease or condition. Conventional cancer treatments often involve surgery, radiation treatment, the administration of a combination of cytotoxic drugs to achieve additive or synergistic effects, and combinations of any or all of these approaches. Especially useful chemotherapeutic and biologic therapy combinations employ drugs that work via different mechanisms of action, increasing cancer cell control or killing, increasing the ability of the immune system to control cancer cell growth, reducing the likelihood of drug resistance during therapy, and minimizing possible overlapping toxicities by permitting the use of reduced doses of individual drugs.

Classes of conventional anti-tumor/anti-neoplastic agents useful in the combination therapies encompassed by the present methods are disclosed, for example, in *Goodman & Gilman's The Pharmacological Basis of Therapeutics*, Twelfth Edition (2010) L. L. Brunton, B. A. Chabner, and B. C. Knollmann Eds., Section VIII, "Chemotherapy of Neoplastic Diseases", Chapters 60-63, pp. 1665-1770, McGraw-Hill, NY, and include, for example, alkylating agents, antimetabolites, natural products, a variety of miscellaneous agents, hormones and antagonists, targeted drugs, monoclonal antibodies and other protein therapeutics.

In addition to the foregoing, the methods of the present disclosure are related to treatment of cancer indications and further comprises treating the patient via surgery, radiation, and/or administering to a patient in need thereof an effective amount of a chemical small molecule or biologic drug including, but not limited to, a peptide, polypeptide, protein, nucleic acid therapeutic, conventionally used or currently being developed, to treat tumorous conditions. This includes antibodies and antigen-binding fragments, other than those disclosed herein, cytokines, antisense oligonucleotides, siRNAs, and miRNAs.

The therapeutic methods disclosed and claimed herein include the use of the antibodies disclosed herein alone, and/or in combinations with one another, and/or with antigen-binding fragments thereof of the present disclosure that bind to CD47, and/or with competing antibodies exhibiting appropriate biological/therapeutic activity, as well, for example, all possible combinations of these antibody compounds to achieve the greatest treatment efficacy.

In addition, the present therapeutic methods also encompass the use of these antibodies, antigen-binding fragments thereof, competing antibodies and combinations thereof further in combination with: (1) any one or more anti-tumor therapeutic treatments selected from surgery, radiation, anti-tumor, anti-neoplastic agents, and combinations of any of these, or (2) any one or more of anti-tumor biological agents, or (3) equivalents of any of the foregoing of (1) or (2) as would be apparent to one of ordinary skill in the art, in appropriate combination(s) to achieve the desired therapeutic treatment effect for the particular indication.

Antibody and small molecule drugs that increase the immune response to cancer by modulating co-stimulatory or inhibitory interactions that influence the T cell response to tumor antigens, including inhibitors of immune checkpoints and modulators of co-stimulatory molecules, are also of particular interest in the context of the combination therapeutic methods encompassed herein and include, but are not limited to, other anti-CD47 antibodies. Administration of therapeutic agents that bind to the CD47 protein, for example, antibodies or small molecules that bind to CD47 and prevent interaction between CD47 and SIRPα, are administered to a patient, causing the clearance of cancer cells via phagocytosis. The therapeutic agent that binds to the CD47 protein is combined with a therapeutic agent such as an antibody, a chemical small molecule or biologic drug disclosed herein, directed against one or more additional cellular targets of CD70 (Cluster of Differentiation 70), CD200 (OX-2 membrane glycoprotein, Cluster of Differentiation 200), CD154 (Cluster of Differentiation 154, CD40L, CD40 ligand, Cluster of Differentiation 40 ligand), CD223 (Lymphocyte-activation gene 3, LAG3, Cluster of Differentiation 223), KIR (Killer-cell immunoglobulin-like receptors), GITR (TNFRSF18, glucocorticoid-induced TNFR-related protein, activation-inducible TNFR family receptor, AITR, Tumor necrosis factor receptor superfamily member 18), CD28 (Cluster of Differentiation 28), CD40 (Cluster of Differentiation 40, Bp50, CDW40, TNFRSF5, Tumor necrosis factor receptor superfamily member 5, p50), CD86 (B7-2, Cluster of Differentiation 86), CD160 (Cluster of Differentiation 160, BY55, NK1, NK28), CD258 (LIGHT, Cluster of Differentiation 258, Tumor necrosis factor ligand superfamily member 14, TNFSF14, HVEML, HVEM ligand, herpesvirus entry mediator ligand, LTg), CD270 (HVEM, Tumor necrosis factor receptor superfamily member 14, herpesvirus entry mediator, Cluster of Differentiation 270, LIGHTR, HVEA), CD275 (ICOSL, ICOS ligand, Inducible T-cell co-stimulator ligand, Cluster of Differentiation 275), CD276 (B7-H3, B7 homolog 3, Cluster of Differentiation 276), OX40L (OX40 Ligand), B7-H4 (B7 homolog 4, VTCN1, V-set domain-containing T-cell activation inhibitor 1), GITRL (Glucocorticoid-induced tumor necrosis factor receptor-ligand, glucocorticoid-induced TNFR-ligand), 4-1BBL (4-1BB ligand), CD3 (Cluster of Differentiation 3, T3D), CD25 (IL2Rα, Cluster of Differentiation 25, Interleukin-2 Receptor α chain, IL-2 Receptor α chain), CD48 (Cluster of Differentiation 48, B-lymphocyte activation marker, BLAST-1, signaling lymphocytic activation molecule 2, SLAMF2), CD66a (Ceacam-1, Carcinoembryonic antigen-related cell adhesion molecule 1, biliary glycoprotein, BGP, BGP1, BGPI, Cluster of Differentiation 66a), CD80 (B7-1, Cluster of Differentiation 80), CD94 (Cluster of Differentiation 94), NKG2A (Natural killer group 2A, killer cell lectin-like receptor subfamily D member 1, KLRD1), CD96 (Cluster of Differentiation 96, TActILE, T cell activation increased late expression), CD112 (PVRL2, nectin, Poliovirus receptor-related 2, herpesvirus entry mediator B, HVEB, nectin-2, Cluster of Differentiation 112), CD115 (CSF1R, Colony stimulating factor 1 receptor, macrophage colony-stimulating factor receptor, M-CSFR, Cluster of Differentiation 115), CD205 (DEC-205, LY75, Lymphocyte antigen 75, Cluster of Differentiation 205), CD226 (DNAM1, Cluster of Differentiation 226, DNAX Accessory Molecule-1, PTA1, platelet and T cell activation antigen 1), CD244 (Cluster of Differentiation 244, Natural killer cell receptor 2B4), CD262 (DRS, TrailR2, TRAIL-R2, Tumor necrosis factor receptor superfamily member 10b, TNFRSF10B, Cluster of Differentiation 262, KILLER, TRICK2, TRICKB, ZTNFR9, TRICK2A, TRICK2B), CD284 (Toll-like Receptor-4, TLR4, Cluster of Differentiation 284), CD288 (Toll-like Receptor-8, TLR8, Cluster of Differentiation 288), TNFSF15 (Tumor necrosis factor superfamily member 15, Vascular endothelial growth inhibitor, VEGI, TL1A), TDO2 (Tryptophan 2,3-dioxygenase, TPH2, TRPO), IGF-1R (Type 1 Insulin-like Growth Factor), GD2 (Disialoganglioside 2), TMIGD2 (Transmembrane and immunoglobulin domain-containing protein 2), RGMB (RGM domain family, member B), VISTA (V-domain immunoglobulin-containing suppressor of T-cell activation, B7-H5, B7 homolog 5), BTNL2 (Butyrophilin-like protein 2), Btn (Butyrophilin family), TIGIT (T cell Immunoreceptor with Ig and ITIM domains, Vstm3, WUCAM), Siglecs (Sialic acid binding Ig-like lectins), Neurophilin, VEGFR (Vascular endothelial growth factor receptor), ILT family (LIRs, immunoglobulin-like transcript family, leukocyte immunoglobulin-like receptors), NKG families (Natural killer group families, C-type lectin transmembrane receptors), MICA (MHC class I polypeptide-related sequence A), TGFβ (Transforming growth factor β), STING pathway (Stimulator of interferon gene pathway), Arginase (Arginine amidinase, canavanase, L-arginase, arginine transamidinase), EGFRvIII (Epidermal growth factor receptor variant III), and HHLA2 (B7-H7, B7y, HERV-H LTR-associating protein 2, B7 homolog 7), inhibitors of PD-1 (Programmed cell death protein 1, PD-1, CD279, Cluster of Differentiation 279), PD-L1 (B7-H1, B7 homolog 1, Programmed death-ligand 1, CD274, cluster of Differentiation 274), PD-L2 (B7-DC, Programmed cell death 1 ligand 2, PDCD1LG2, CD273, Cluster of Differentiation 273), CTLA-4 (Cytotoxic T-lymphocyte-associated protein 4, CD152, Cluster of Differentiation 152), BTLA (B- and T-lymphocyte attenuator, CD272, Cluster of Differentiation 272), Indoleamine 2,3-dioxygenase (IDO, IDO1), TIM3 (HAVCR2, Hepatitis A virus cellular receptor 2, T cell immunoglobulin mucin-3, KIM-3, Kidney injury molecule 3, TIMD-3, T cell immunoglobulin mucin-domain 3), A2A adenosine receptor (ADO receptor), CD39 (ectonucleoside triphosphate diphosphohydrolase-1, Cluster of Differentiation 39, ENTPD1), and CD73 (Ecto-5'-nucleotidase, 5'-nucleotidase, 5'-NT, Cluster of Differentiation 73), CD27 (Cluster of Differentiation 27), ICOS (CD278, Cluster of Differentiation 278, Inducible T-cell Co-stimulator), CD137 (4-1BB, Cluster of Differentiation 137, tumor necrosis factor receptor superfamily member 9, TNFRSF9), OX40 (CD134, Cluster of Differentiation 134), and TNFSF25 (Tumor necrosis factor receptor superfamily member 25), including antibodies, small molecules, and agonists, are also specifically contemplated herein. Additional agents include IL-10 (Interleukin-10, human cytokine synthesis inhibitory factor, CSIF) and Galectins.

YERVOY® (ipilimumab; Bristol-Meyers Squibb) is an example of an approved anti-CTLA-4 antibody.

KEYTRUDA® (pembrolizumab; Merck) and OPDIVO® (nivolumab; Bristol-Meyers Squibb Company) are examples of approved anti-PD-1 antibodies.

TECENTRIQ™ (atezolizumab; Roche) is an example of an approved anti-PD-L1 antibody.

Ischemia-Reperfusion Injury (IRI)-Related, Autoimmune, Autoinflammatory, Inflammatory, Cardiovascular Conditions and Diseases Administration of a CD47 mAb or antigen binding fragment thereof disclosed herein can be used to treat a number of diseases and conditions in which IRI is a contributing feature, and to treat various autoimmune, autoinflammatory, inflammatory and cardiovascular diseases. These include: organ transplantation in which a mAb or antigen binding fragment thereof of the present invention is administered to the donor prior to organ harvest, to the harvested donor organ in the organ preservation solution, to the recipient patient, or to any combination thereof; skin grafting; surgical resections or tissue reconstruction in which such mAb or fragment is administered either locally by injection to the affected tissue or parenterally to the patient; reattachment of body parts; treatment of traumatic injury; pulmonary hypertension; pulmonary arterial hypertension; sickle cell disease (crisis); myocardial infarction; cerebrovascular disease; stroke; surgically-induced ischemia; acute kidney disease/kidney failure; any other condition in which IRI occurs and contributes to the pathogenesis of disease; autoimmune and inflammatory diseases, including arthritis, rheumatoid arthritis, multiple sclerosis, psoriasis, psoriatic arthritis, Crohn's disease, inflammatory bowel disease, ulcerative colitis, lupus, systemic lupus erythematous, juvenile rheumatoid arthritis, juvenile idiopathic arthritis, Grave's disease, Hashimoto's thyroiditis, Addison's disease, celiac disease, dermatomyositis, multiple sclerosis, myasthenia gravis, pernicious anemia, Sjogren syndrome, type I diabetes, vasculitis, uveitis and ankylosing spondylitis; autoinflammatory diseases, including familial Mediterranean fever, neonatal onset multisystem inflammatory disease, tumor necrosis factor (TNF) receptor-associated periodic syndrome, deficiency of the interleukin-1 receptor antagonist, Behcet's disease; cardiovascular diseases, including coronary heart disease, coronary artery disease, atherosclerosis, myocardial infarction, heart failure, and left ventricular heart failure.

Anti-CD47 mAbs and antigen binding fragments thereof of the present invention can also be used to increase tissue perfusion in a subject in need of such treatment. Such subjects can be identified by diagnostic procedures indicating a need for increased tissue perfusion. In addition, the need for increased tissue perfusion may arise because the subject has had, is having, or will have, a surgery selected from integument surgery, soft tissue surgery, composite tissue surgery, skin graft surgery, resection of a solid organ, organ transplant surgery, or reattachment or an appendage or other body part.

Treatment of Ischemia-Reperfusion Injury (IRI)-Related Indications

The methods of the present disclosure, for example those related to treatment of IRI-related indications, can further comprise administering to a patient in need thereof an effective amount of therapeutic agent that binds to the CD47 protein and a nitric oxide donor, precursor, or both; a nitric oxide generating topical agent; an agent that activates soluble guanylyl cyclase; an agent that inhibits cyclic nucleotide phosphodiesterases; or any combination of any of the foregoing.

In these methods, the nitric oxide donor or precursor can be selected from NO gas, isosorbide dinitrate, nitrite, nitroprusside, nitroglycerin, 3-Morpholinosydnonimine (SIN-1), S-nitroso-N-acetylpenicillamine (SNAP), Diethylenetriamine/NO (DETA/NO), S-nitrosothiols, Bidil®, and arginine.

The agent that activates soluble guanylyl cyclase can be a non-NO (nitric oxide)-based chemical activator of soluble guanylyl cyclase that increases cGMP levels in vascular cells. Such agents bind soluble guanylyl cyclase in a region other than the NO binding motif, and activate the enzyme regardless of local NO or reactive oxygen stress (ROS). Non-limiting examples of chemical activators of soluble guanylyl cyclase include organic nitrates (Artz et al. (2002) *J. Biol. Chem.* 277:18253-18256); protoporphyrin IX (Ignarro et al. (1982) *Proc. Natl. Acad. Sci. USA* 79:2870-2873); YC-1 (Ko et al. (1994) *Blood* 84:4226-4233); BAY 41-2272 and BAY 41-8543 (Stasch et al. (2001 *Nature* 410 (6825): 212-5), CMF-1571, and A-350619 (reviewed in Evgenov et al. (2006) *Nat. Rev. Drug. Discov.* 5:755-768); BAY 58-2667 (Cinaciguat; Frey et al. (2008) *Journal of Clinical Pharmacology* 48 (12): 1400-10); BAY 63-2521 (Riociguat; Mittendorf et al. (2009) *Chemmedchem* 4 (5): 853-65). Additional soluble guanylyl cyclase activators are disclosed in Stasch et al. (2011) *Circulation* 123:2263-2273; Derbyshire and Marletta (2012) *Ann. Rev. Biochem.* 81:533-559, and Nossaman et al. (2012) *Critical Care Research and Practice*, Volume 2012, Article ID 290805, pages 1-12.

The agent that inhibits cyclic nucleotide phosphodiesterases can be selected from, tadalafil, vardenafil, udenafil, sildenafil and avanafil.

Treatment of Autoimmune, Autoinflammatory, Inflammatory Diseases and Cardiovascular Diseases A therapeutic agent that binds to the CD47 protein for the treatment of an autoimmune, autoinflammatory, inflammatory disease and/or cardiovascular disease can be combined with one or more therapeutic agent(s) such as an antibody, a chemical small molecule, or biologic or a medical or surgical procedure which include, but are not limited to the following. For the treatment of autoimmune, autoinflammatory and inflammatory diseases, the combined therapeutic agents are: hydroxychloroquine, leflunomide, methotrexate, minocycline, sulfasalazine, abatacept, rituximab, tocilizumab, anti-TNF inhibitors or blockers (adalimumab, etanercept, infliximab, certolizumab pegol, golimumab), non-steroidal anti-inflammatory drugs, glucocorticoids, corticosteroids, intravenous immunoglobulin, anakinra, canakinumab, rilonacept, cyclophosphamide, mycophenolate mofetil, azathioprine, 6-mercaptopurine, belimumab, beta interferons, glatiramer acetate, dimethyl fumarate, fingolimod, teriflunomide, natalizumab, 5-aminosalicylic acid, mesalamine, cyclosporine, tacrolimus, pimecrolimus, vedolizumab, ustekinumab, secukinumab, ixekizumab, apremilast, budesonide and tofacitinib. For the treatment of atherosclerosis, the combined therapeutic agents or procedures are: medical procedures and/or surgery, including percutaneous coronary intervention (coronary angioplasty and stenting), coronary artery bypass grafting, and carotid endarterectomy; therapeutic agents, including angiotensin-converting enzyme (ACE) inhibitors (including ramipril, quinapril, captopril, and enalapril), calcium channel blockers (including amiodipine, nifedipine, verapamil, felodipine and diltiazem), angiotensin-receptor blockers (including eposartan, olmesarten, azilsartan, valsartan, telmisartan, losartan, candesartan, and irbesartan), the combination of ezetimibe and simvastatin, PCSK9 inhibitors (including alirocumab and evolocumab), anacetrapib, and HMG-CoA inhibitors (including atorvastatin, pravastatin, simvastatin, rosuvastatin, pitavastatin, lovastatin and fluvastatin). For the treatment of heart failure, the combined therapeutic agents are: ACE inhibitors, angiotensin receptor blockers, angiotensin receptor neprilsyn inhibitors (including the combination of sacubitril and valsartan), diuretics, digoxin, inotropes, beta blockers and aldosterone antagonists. For the treatment of pumonary hypertension the combined therapeutic agents are: sildenafil, tadalafil, ambrisentan, bosentan, macitentan, riociguat, treprostinil, epoprostenol, iloprost, and selexipag.

As disclosed herein, the anti-CD47 mAb is administered before, at the same time or after the combined therapeutic agents or medical or surgical procedures.

Another useful class of compounds for the combination therapies contemplated herein includes modulators of SIRPα/CD47 binding such as antibodies to SIRPα, as well as soluble protein fragments of this ligand, or CD47 itself, inhibiting binding of, or interfering with binding of, SIRPα to CD47. It should be noted that the therapeutic methods encompassed herein include the use of the antibodies disclosed herein alone, in combination with one another, and/or with antigen-binding fragments thereof as well, for example, all possible combinations of these antibody compounds.

The examples illustrate various embodiments of the present disclosure, but should not be considered as limiting the disclosure to only these particularly disclosed embodiments.

Diagnostics for CD47 Expression

Diagnostics (including complementary and companion) have been an area of focus in the field of oncology. A number of diagnostic assays have been developed for targeted therapeutics such as Herceptin (Genentech), Tarceva (OSI Pharmaceuticals/Genentech), Iressa (Astra Zeneca), and Erbitux (Imclone/Bristol Myers Squibb). The anti-CD47 mAbs antibodies of the disclosure are particularly well-suited to use in diagnostic applications. Accordingly, the disclosure provides a method to measure CD47 expression in tumor and/or immune cells, using an anti-CD47 mAb of the disclosure.

The anti-CD47 mAbs of the disclosure may be used in a diagnostic assay and/or in vitro method to measure CD47 expression in tumor and/or immune cells present in a patient's tumor sample. In particular, the anti-CD47 mAbs of the disclosure may bind CD47 on approximately 1% or more of tumor and/or immune cells present in a patient's sample as compared to a reference level. In another embodiment, the anti-CD47 mAbs may bind CD47 on approximately 5% or more of tumor and/or immune cells in a patient's sample as compared to a reference level, for example, or binding at least 10%, or at least 20%, or at least 30%, or at least about 40%, or at least about 50%, or at least about 60%, or at least about 70%, or at least about 80%, or at least about 90%, or between 10-100% as compared to a reference level. In yet another embodiment, the anti-CD47 mAbs may bind CD47 on tumor and/or immune cells in a patient's sample to at least about a 2-fold increase as compared to a reference level, or at least about 3-fold, or at least about a 4-fold, or at least about a 5-fold or at least about a 10-fold increase, or between 2-fold and 10-fold or greater as compared to a reference level. As described herein, the measurement of CD47 expression in a patient's sample provides biological and/or clinical information that enables decision making about the development and use of a potential drug therapy, notably the use of anti-CD47 antibodies for treating solid and hematological cancers, autoimmune disease, inflammatory disease, atherosclerosis, heart failure, in which the CD47 receptor plays a role.

In one embodiment, the in vitro method comprises, obtaining a patient sample, contacting the patient sample with a monoclonal antibody, or antigen-binding fragment thereof, which specifically binds to an epitope within the sequence of SEQ ID NO:6566, and assaying for binding of the antibody to the patient sample, wherein binding of the antibody to the patient sample is diagnostic of CD47 expression in a patient sample.

In another embodiment, the preferred CD47 antibodies, or antigen binding fragments thereof, for the in vitro method, are those comprising a combination of a heavy chain (HC) and a light chain (LC), listed from the combination of:
  (i) a heavy chain comprising the amino acid sequence of SEQ ID NO:102 and a light chain comprising the amino acid sequence SEQ ID NO:101;
  (ii) a heavy chain comprising the amino acid sequence of SEQ ID NO:104 and a light chain comprising the amino acid sequence SEQ ID NO:103;
  wherein the $V_H$ amino acid sequence is at least 90%, 95%, 97%, 98% or 99% identical thereto and the a $V_L$ amino acid sequence is at least 90%, 95%, 97%, 98% or 99% identical thereto.

Accordingly, a diagnostic assay in accordance with the disclosure may comprise contacting tumor and/or immune cells in a patient's sample with an anti-CD47 mAb, or an antigen binding fragment thereof, and assaying for binding of the anti-CD47 mAb to a patient's tumor sample, wherein binding of the anti-CD47 mAb to the patient sample is diagnostic of CD47 expression. Preferably, the patient's sample is a sample containing tumor cells. In this case, binding of the anti-CD47 mAb of the disclosure, or antigen binding fragment thereof, to the tumor cells may be assessed for CD47 expression. The levels of CD47 expression by tumor cells and/or immune cells of a patient's tumor sample may be predictive of clinical outcome in a patient.

Increased binding of anti-CD47 mAbs binding to cells in a patient's sample is associated with increased CD47 expression. In one embodiment, the anti-CD47 mAbs of the disclosure may bind to approximately 5% or more of tumor cells in a patient's sample and this may indicate that the patient would benefit from rapid intervention to a solid and hematological cancer. A diagnostic assay of this sort may be used to determine suitable therapeutic regimes for solid and hematological cancers with relatively high binding of anti-CD47 mAbs of the disclosure, i.e., increased CD47 expression.

It will be appreciated that the diagnostic assay disclosed herein has a number of advantages. The most important of these advantages is that the diagnostic assay of the disclosure may allow the user a greater deal of confidence in the CD47 expression in tumor and/or immune cells. The increased sensitivity of the diagnostic assay of the disclosure allows detection of CD47 in a patient's sample at lower levels than has previously been the case.

The anti-CD47 mAbs of the disclosure may be used as a diagnostic assay in relation to many forms of cancer. Particular forms of cancer that may advantageously be investigated for CD47 expression include susceptible hematologic cancers and solid tumors including, but not limited to, leukemias, lymphomas, and solid tumors.

The diagnostic assays of the disclosure may utilize any suitable means for detecting binding of an anti-CD47 mAb to measure CD47 expression. Suitable methods may be selected with reference to the nature of any reporter moiety used to label the anti-CD47 mAbs of the disclosure. Suitable techniques include, but are by no means limited to, flow cytometry, and enzyme linked immunosorbent assays (ELISA) and assays utilizing nanoparticles. It is particularly preferred that a diagnostic assay of the invention be one involving immunohistochemistry in which a tumor sample is exposed to an anti-CD47 mAb of the disclosure, and the level of cell labelling is assessed by immunohistochemistry.

EXAMPLES

Example 1

Amino Acid Sequences
Light Chain CDRs

| LCDR1 | LCDR2 | LCDR3 |
|---|---|---|
| Vx4-LCDR1 RSRQSIVHTNGNTYLG (SEQ ID NO: 11) | Vx4-LCDR2 KVSNRFS (SEQ ID NO: 15) | Vx4-LCDR3 FQGSHVPYT (SEQ ID NO: 18) |
| Vx8-LCDR1 RASQDISNYLN (SEQ ID NO: 12) | Vx8-LCDR2 YTSRLYS (SEQ ID NO: 16) | Vx8-LCDR3 QQGNTLPWT (SEQ ID NO: 19) |
| Vx8-LCDR1 RASQSISNYLN (SEQ ID NO: 13) | | |
| Vx9-LCDR1 RSSQNIVQSNGNTYLE (SEQ ID NO: 14) | Vx9-LCDR2 KVFHRFS (SEQ ID NO: 17) | Vx9-LCDR3 FQGSHVPWT (SEQ ID NO: 20) |

| HCDR1 | HCDR2 | HCDR3 |
|---|---|---|
| Vx4-HCDR1 GYTFTNYVIH (SEQ ID NO: 1) | Vx4-HCDR2 YIYPYNDGILYNEKFKG (SEQ ID NO: 4) | Vx4-HCDR3 GGYYVPDY (SEQ ID NO: 7) |
| | | Vx4-HCDR3 GGYYVYDY (SEQ ID NO: 8) |

| HCDR1 | HCDR2 | HCDR3 |
|---|---|---|
| Vx8-HCDR1<br>GYSFTNYYIH<br>(SEQ ID NO: 2) | Vx8-HCDR2<br>YIDPLNGDTTYNQKFKG<br>(SEQ ID NO: 5) | Vx8-HCDR3<br>GGKRAMDY<br>(SEQ ID NO: 9) |
| Vx9-HCDR1<br>GYTFTNYWIH<br>(SEQ ID NO: 3) | Vx9-HCDR2<br>YTDPRTDYTEYNQKFKD<br>(SEQ ID NO: 6) | Vx9-HCDR3<br>GGRVGLGY<br>(SEQ ID NO: 10) |

Murine Light Chain Variable Domains

>Vx4murL01
(SEQ ID NO: 41)
DVLMTQTPLSLPVNLGDQASISCRSRQSIVHTNGNTYLGWFLQKPGQS
PKLLIYKVSNRFSGVPDRFSGSGSGTDFTLTISRVEAEDLGVYYCFQG
SHVPYTFGGGTKLEIK.

>Vx4murL02
(SEQ ID NO: 42)
DVLMTQTPLSLPVNLGDQASISCRSRQSIVHTNGNTYLGWFLQKPGQS
PKLLIYKVSNRFSGVPDRFSGSGSGTDFTLTISRVEAEDLGVYYCFQG
SHVPYTFGQGTKVEIK.

>Vx8murL03
(SEQ ID NO: 46)
DIQMTQTTSSLSASLGDRVTISCRASQDISNYLNWYQQKPDGTVKLLI
YYTSRLYSGVPSRFSGSGSGTDYSLTISNLEQEDIATYFCQQGNTLPW
TFGGGTKLEIK.

>Vx9murL04
(SEQ ID NO: 50)
DVFMTQTPLSLPVSLGDQASISCRSSQNIVQSNGNTYLEWYLQKPGQS
PKLLIYKVFHRFSGVPDRFSGSGSGTDFTLKISRVEAEDLGVYYCFQG
SHVPWTFGGGTKVEIK Murine Heavy Chain Variable Domains >Vx4murH01
(SEQ ID NO: 21)
EVQLQQSGPELVKPGASVKMSCKASGYTFTNYVIHWVKRRPGQGLEWI
GYIYPYNDGILYNEKFKGKATVTSDKSSTAYMDLSSLTSEDSAVYYC
TRGGYYVPDYWGQGTTLTVSS.

>Vx4mur-H02
(SEQ ID NO: 22)
EVQLQQSGPELVKPGASVKMSCKASGYTFTNYVIHWVKRRPGQGLEWI
GYIYPYNDGILYNEKFKGKATVTSDKSSTAYMDLSSLTSEDSAVYYC
TRGGYYVPDYWGQGTLVTVSS.

>Vx8murH03
(SEQ ID NO: 28)
EVQLQQSGPELMKPGASVKISCKASGYSFTNYYIHWVNQSHGKSLEWI
GYIDPLNGDTTYNQKFKGKATLTVDKSSTAYMRLSSLTSADSAVYYC
ARGGKRAMDYWGQGTSVTVSS.

>Vx9murH04
(SEQ ID NO: 35)
QVQLQQFGAELAKPGASVQMSCKASGYTFTNYWIHWVKQRPGQGLEWI
GYTDPRTDYTEYNQKFKDKATLAADRSSTAYMRLSSLTSEDSAVYYC
AGGGRVGLGYWGHGSSVTVSS Human Light Chain Variable Domains >Vx4humL01
(SEQ ID NO: 43)
DIVMTQSPLSLPVTPGEPASISCRSRQSIVHTNGNTYLGWYLQKPGQS
PRLLIYKVSNRFSGVPDRFSGSGSGTDFTLKISRVEADDVGIYYCFQG
SHVPYTFGQGTKLEIK >Vx4humL02
(SEQ ID NO: 44)
DVVMTQSPLSLPVTLGQPASISCRSRQSIVHTNGNTYLGWFQQRPGQS
PRRLIYKVSNRFSGVPDRFSGSGSGTDFTLKISRVEAEDVGVYYCFQG
SHVPYTFGQGTKLEIK >Vx4humL03
(SEQ ID NO: 45)
DIVMTQSPDSLAVSLGERATINCRSRQSIVHTNGNTYLGWYQQKPGQP
PKLLIYKVSNRFSGVPDRFSGSGSGTDFTLTISSLQAEDVAVYYCFQG
SHVPYTFGQGTKLEIK >Vx8humL04
(SEQ ID NO: 47)
DIQMTQSPSSLSASVGDRVTITCRASQDISNYLNWYQQKPGKAPKLLI
YYTSRLYSGVPSRFSGSGSGTDFTFTISSLQPEDIATYYCQQGNTLPW
TFGQGTKVEIK.

>Vx8humL05
(SEQ ID NO: 48)
DIQMTQSPSSLSASVGDRVTITCRASQSISNYLNWYQQKPGKAPKLLI
YYTSRLYSGVPSRFSGSGSGTDFTLTISSLQPEDFATYYCQQGNTLPW
TFGQGTKVEIK.

>Vx8humL06
(SEQ ID NO: 49)
DIVMTQSPLSLPVTPGEPASISCRASQDISNYLNWYLQKPGQSPRLLI
YYTSRLYSGVPDRFSGSGSGTDFTLKISRVEADDVGIYYCQQGNTLPW
TFGQGTKLEIK >Vx9humL07
(SEQ ID NO: 51)
DVVMTQSPLSLPVTLGQPASISCRSSQNIVQSNGNTYLEWFQQRPGQS
PRRLIYKVFHRFSGVPDRFSGSGSGTDFTLKISRVEAEDVGVYYCFQG
SHVPYTFGQGTKLEIK.

>Vx9humL08
(SEQ ID NO: 52)
DIVMTQSPDSLAVSLGERATINCRSSQNIVQSNGNTYLEWYQQKPGQP
PKLLIYKVFHRFSGVPDRFSGSGSGTDFTLTISSLQAEDVAVYYCFQG
SHVPYTFGQGTKLEIK.

Human Heavy Chain Variable Domains

>Vx4humH01
(SEQ ID NO: 23)
QVQLVQSGAEVKKPGASVQVSCKASGYTFTNYVIHWLRQAPGQGLEWM
GYIYPYNDGILYNEKFKGRVTMTSDTSISTAYMELSSLRSDDTAVYYC
ARGGYYVPDYWGQATLVTVSS.

>Vx4humH02
(SEQ ID NO: 24)
QVQLVQSGAEVKKPGASVQVSCKASGYTFTNYVIHWLRQAPGQGLEWM
GYIYPYNDGILYNEKFKGRVTMTSDTSISTAYMELSSLRSDDTAVYYC
ARGGYYVYDYWGQATLVTVSS.

>Vx4humH03
(SEQ ID NO: 25)
EVQLVQSGAEVKKPGATVKISCKVSGYTFTNYVIHWVQQAPGKGLEWM
GYIYPYNDGILYNEKFKGRVTITADTSTDTAYMELSSLRSEDTAVYYC
ATGGYYVPDYWGQGTTVTVSS >Vx4humH04
(SEQ ID NO: 26)
EVQLVQSGAEVKKPGESLKISCKGSGYTFTNYVIHWVRQMPGKGLEWM
GYIYPYNDGILYNEKFKGQVTISADKSISTAYLQWSSLKASDTAMYYC
ARGGYYVPDYWGQGTTVTVSS >Vx4humH05
(SEQ ID NO: 27)
QVQLVQSGAEVKKPGASVKVSCKASGYTFTNYVIHWVRQAPGQGLEWM
GYIYPYNDGILYNEKFKGRVTMTTDTSTSTAYMELRSLRSDDTAVYYC
ARGGYYVPDYWGQGTTVTVSS >Vx8humH06
(SEQ ID NO: 29)
QVQLVQSGAEVKKPGASVKVSCKASGYSFTNYYIHWVRQAPGQGLEWM
GYIDPLNGDTTYNQKFKGRVTMTRDTSTSTVYMELSSLRSEDTAVYYC
ARGGKRAMDYWGQGTLVTVSS.

>Vx8humH07
(SEQ ID NO: 30)
QVQLVQSGAEVKKPGSSVKVSCKASGYSFTNYYIHWVRQAPGQGLEWM
GYIDPLNGDTTYNQKFKGRVTITADESTSTAYMELSSLRSEDTAVYYC
ARGGKRAMDYWGQGTLVTVSS.

>Vx8humH08
(SEQ ID NO: 31)
EVQLVQSGAEVKKPGESLKISCKGSGYSFTNYYIHWVRQMPGKGLEWM
GYIDPLNGDTTYNQKFKGQVTISADKSISTAYLQWSSLKASDTAMYYC
ARGGKRAMDYWGQGTLVTVSS.

>Vx8humH09
(SEQ ID NO: 32)
QVQLVQSGAEVKKPGSSVKVSCKASGYSFTNYYIHWVRQAPGQGLEWM
GYIDPLNGDTTYAQKFQGRVTITADESTSTAYMELSSLRSEDTAVYYC
ARGGKRAMDYWGQGTLVTVSS.

>Vx8humH10
(SEQ ID NO: 33)
EVQLVQSGAEVKKPGESLKISCKGSGYSFTNYYIHWVRQMPGKGLEWM
GYIDPLNGDTTYSPSFQGQVTISADKSISTAYLQWSSLKASDTAMYYC
ARGGKRAMDYWGRGTLVTVSS.

>Vx8humH11
(SEQ ID NO: 34)
QVQLVQSGAEVKKPGASVQVSCKASGYSFTNYYIHWLRQAPGQGLEWM
GYIDPLNGDTTYNQKFKGRVTMTSDTSISTAYMELSSLRSDDTAVYYC
ARGGKRAMDYWGQATLVTVSS >Vx9humH12
(SEQ ID NO: 36)
QVQLVQSGAEVKKPGASVKVSCKASGYTFTNYWIHWVRQAPGQGLEWM
GYTDPRTDYTEYNQKFKDRVTMTRDTSTSTVYMELSSLRSEDTAVYYC
ARGGRVGLGYWGQGTLVTVSS.

>Vx9humH13
(SEQ ID NO: 37)
QVQLVQSGAEVKKPGSSVKVSCKASGYTFTNYWIHWVRQAPGQGLEWM
GYTDPRTDYTEYNQKFKDRVTITADESTSTAYMELSSLRSEDTAVYYC
ARGGRVGLGYWGQGTLVTVSS.

>Vx9humH14
(SEQ ID NO: 38)
EVQLVQSGAEVKKPGESLKISCKGSGYTFTNYWIHWVRQMPGKGLEWM
GYTDPRTDYTEYNQKFKDQVTISADKSISTAYLQWSSLKASDTAMYYC
ARGGRVGLGYWGQGTLVTVSS.

>Vx9humH15
(SEQ ID NO: 39)
QVQLVQSGAEVKKPGSSVKVSCKASGYTFTNYWIHWVRQAPGQGLEWM
GYTDPRTDYTEYAQKFQGRVTITADESTSTAYMELSSLRSEDTAVYYC
ARGGRVGLGYWGQGTLVTVSS.

>Vx9humH16
(SEQ ID NO: 40)
EVQLVQSGAEVKKPGESLKISCKGSGYTFTNYWIHWVRQMPGKGLEWM
GYTDPRTDYTEYSPSFQGQVTISADKSISTAYLQWSSLKASDTAMYYC
ARGGRVGLGYWGQGTLVTVSS.

Human IgG-Fc

>Human Fc IgG1
(SEQ ID NO: 53)
ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFF
LYSKLTVDKSRWQQGNVFSCSVMHEALHNHYTQKSLSLSPGK.

>Human Fc IgG1-N297Q
(SEQ ID NO: 54)
ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTC

VVVDVSHEDPEVKFNWYVDGVEVHNAKTKPREEQYQSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK.

>Human Fc-IgG2
(SEQ ID NO: 55)
ASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDK

TVERKCCVECPPCPAPPVAGPSVFLFPPKPKDTLMISRTPEVTCVVVD

VSHEDPEVQFNWYVDGVEVHNAKTKPREEQFNSTFRVVSVLTVVHQDW

LNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSK

LTVDKSRWQQGNVFSCSVMHEALHNHYTQKSLSLSPGK.

>Human Fc-IgG3
(SEQ ID NO: 56)
ASTKGPSVFPLAPCSRSTSGGTAALGCLVKDYFPEPVTVSWNSGALTS

GVHTFPAVLQSSGLYSLSSVVTVPSSSLGTQTYTCNVNHKPSNTKVDK

RVELKTPLGDTTHTCPRCPEPKSCDTPPPCPRCPEPKSCDTPPPCPRC

PEPKSCDTPPPCPRCPAPELLGGPSVFLFPPKPKDTLMISRTPEVTCV

VVDVSHEDPEVQFKWYVDGVEVHNAKTKPREEQYNSTFRVVSVLTVLH

QDWLNGKEYKCKVSNKALPAPIEKTISKTKGQPREPQVYTLPPSREEM

TKNQVSLTCLVKGFYPSDIAVEWESSGQPENNYNTTPPMLDSDGSFFL

YSKLTVDKSRWQQGNIFSCSVMHEALHNRFTQKSLSLSPGK

>Human Fc-IgG4
(SEQ ID NO: 57)
ASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDK

RVESKYGPPCPSCPAPEFLGGPSVFLFPPKPKDTLMISRTPEVTCVVV

DVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYS

RLTVDKSRWQEGNVFSCSVMHEALHNHYTQKSLSLSLG.

>Human Fc-IgG4 S228P
(SEQ ID NO: 58)
ASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDK

RVESKYGPPCPPCPAPEFLGGPSVFLFPPKPKDTLMISRTPEVTCVVV

DVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYS

RLTVDKSRWQEGNVFSCSVMHEALHNHYTQKSLSLSLG.

>Human Fc-IgG4 PE
(SEQ ID NO: 59)
ASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDK

RVESKYGPPCPPCPAPEFEGGPSVFLFPPKPKDTLMISRTPEVTCVVV

DVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYS

RLTVDKSRWQEGNVFSCSVMHEALHNHYTQKSLSLSLGK

>Human Fc-IgG4 PE'
(SEQ ID NO: 99)
ASTKGPSVFPLAPCSRSTSESTAALGCLVKDYFPEPVTVSWNSGALTS

GVHTFPAVLQSSGLYSLSSVVTVPSSSLGTKTYTCNVDHKPSNTKVDK

RVESKYGPPCPPCPAPEFEGGPSVFLFPPKPKDTLMISRTPEVTCVVV

DVSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYS

RLTVDKSRWQEGNVFSCSVMHEALHNHYTQKSLSLSLG

>Human kappa LC
(SEQ ID NO: 60)
RTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSS

PVTKSFNRGEC.

>Rat Fc-IgG2c
(SEQ ID NO: 61)
ARTTAPSVYPLVPGCSGTSGSLVTLGCLVKGYFPEPVTVKWNSGALSS

GVHTFPAVLQSGLYTLSSSVTVPSSTWSSQTVTCSVAHPATKSNLIKR

IEPRRPKPRPPTDICSCDDNLGRPSVFIFPPKPKDILMITLTPKVTCV

VVDVSEEEPDVQFSWFVDNVRVFTAQTQPHEEQLNGTFRVVSTLHIQH

QDWMSGKEFKCKVNNKDLPSPIEKTISKPRGKARTPQVYTIPPPREQM

SKNKVSLTCMVTSFYPASISVEWERNGELEQDYKNTLPVLDSDESYFL

YSKLSVDTDSWMRGDIYTCSVVHEALHNHHTQKNLSRSPGK.

>Rat kappa LC
(SEQ ID NO: 62)
RADAAPTVSIFPPSMEQLTSGGATVVCFVNNFYPRDISVKWKIDGSEQ

RDGVLDSVTDQDSKDSTYSMSSTLSLTKVEYERHNLYTCEVVHKTSSS

PVVKSFNRNEC.

Rabbit IgG-Fc

>Rabbit IgG
(SEQ ID NO: 63)
GQPKAPSVFPLAPCCGDTPSSTVTLGCLVKGYLPEPVTVTWNSGTLTN

GVRTFPSVRQSSGLYSLSSVVSVTSSSQPVTCNVAHPATNTKVDKTVA

PSTCSKPTCPPPELLGGPSVFIFPPKPKDTLMISRTPEVTCVVVDVSQ

DDPEVQFTWYINTNEQVRTARPPLREQQFNSTIRVVSTLPIAHQDWLR
GKEFKCKVHNKALPAPIEKTISKARGQPLEPKVYTMGPPREELSSRSV
SLTCMINTGFYPSDISVEWEKNGKAEDNYKTTPAVLDSDGSYFLYSKL
SVPTSEWQRGDVFTCSVMHEALHNHYTQKSISRSPGK.

>Rabbit kappa LC (SEQ ID NO: 64)
RDPVAPTVLIFPPAADQVATGTVTIVCVANKYFPDVTVTWEVDGTTQT
TGIENSKTPQNSADCTYNLSSTLTLTSTQYNSHKEYTCKVTQGTTSVV
QSFNRGDC.

>CD47

(SEQ ID NO: 65)
MWPLVAALLLGSACCGSAQLLFNKTKSVEFTFCNDTVVIPCFVTNMEA
QNTTEVYVKWKFKGRDIYTFDGALNKSTVPTDFSSAKIEVSQLLKGDA
SLKMDKSDAVSHTGNYTCEVTELTREGETIIELKYRVVSWFSPNENIL
IVIFPIFAILLFWGQFGIKTLKYRSGGMDEKTIALLVAGLVITVIVIV
GAILFVPGEYSLKNATGLGLIVTSTGILILLHYYVFSTAIGLTSFVIA
ILVIQVIAYILAVVGLSLCIAACIPMHGPLLISGLSILALAQLLGLVY
MKFVE.

Chimera and Human Light Chains

>Vx4murL01 Full length (SEQ ID NO: 66)
DVLMTQTPLSLPVNLGDQASISCRSRQSIVHTNGNTYLGWFLQKPGQS
PKLLIYKVSNRFSGVPDRFSGSGSGTDFTLTISRVEAEDLGVYYCFQG
SHVPYTFGGGTKLEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC.

>Vx4murL01 Full length (SEQ ID NO: 67)
DVLMTQTPLSLPVNLGDQASISCRSRQSIVHTNGNTYLGWFLQKPGQS
PKLLIYKVSNRFSGVPDRFSGSGSGTDFTLTISRVEAEDLGVYYCFQG
SHVPYTFGQGTKVEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC.

>Vx4humL01 Full length LC (SEQ ID NO: 68)
DIVMTQSPLSLPVTPGEPASISCRSRQSIVHTNGNTYLGWYLQKPGQS
PRLLIYKVSNRFSGVPDRFSGSGSGTDFTLKISRVEADDVGIYYCFQG
SHVPYTFGQGTKLEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC.

>Vx8humL03 Full length LC (SEQ ID NO: 69)
DIVMTQSPLSLPVTPGEPASISCRASQDISNYLNWYLQKPGQSPRLLI
YYTSRLYSGVPDRFSGSGSGTDFTLKISRVEADDVGIYYCQQGNTLPW
TFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC.

>Vx9humL02 Full length LC (SEQ ID NO: 70)
DIVMTQSPDSLAVSLGERATINCRSSQNIVQSNGNTYLEWYQQKPGQP
PKLLIYKVFHRFSGVPDRFSGSGSGTDFTLTISSLQAEDVAVYYCFQG
SHVPYTFGQGTKLEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC.

>Vx8humL02 Full length LC (SEQ ID NO: 71)
DIQMTQSPSSLSASVGDRVTITCRASQSISNYLNWYQQKPGKAPKLLI
YYTSRLYSGVPSRFSGSGSGTDFTLTISSLQPEDFATYYCQQGNTLPW
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC.

>Vx4humL02 Full length LC (SEQ ID NO: 72)
DVVMTQSPLSLPVTLGQPASISCRSRQSIVHTNGNTYLGWFQQRPGQS
PRRLIYKVSNRFSGVPDRFSGSGSGTDFTLKISRVEAEDVGVYYCFQG
SHVPYTFGQGTKLEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC.

>Vx9humL07 Full length LC (SEQ ID NO: 73)
DVVMTQSPLSLPVTLGQPASISCRSSQNIVQSNGNTYLEWFQQRPGQS
PRRLIYKVFHRFSGVPDRFSGSGSGTDFTLKISRVEAEDVGVYYCFQG
SHVPYTFGQGTKLEIKRTVAAPSVFIFPPSDEQLKSGTASVVCLLNNF
YPREAKVQWKVDNALQSGNSQESVTEQDSKDSTYSLSSTLTLSKADYE
KHKVYACEVTHQGLSSPVTKSFNRGEC.

>Vx8humL01 Full length LC (SEQ ID NO: 74)
DIQMTQSPSSLSASVGDRVTITCRASQDISNYLNWYQQKPGKAPKLLI
YYTSRLYSGVPSRFSGSGSGTDFTFTISSLQPEDIATYYCQQGNTLPW
TFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC.

>Vx8murL03 Full length LC (SEQ ID NO: 100)
DIQMTQTTSSLSASLGDRVTISCRASQDISNYLNWYQQKPDGTVKLLI
YYTSRLYSGVPSRFSGSGSGTDYSLTISNLEQEDIATYFCQQGNTLPW
TFGGGTKLEIKRTVAAPSVFIFPPSDEQLKSGTASVVCLLNNFYPREA
KVQWKVDNALQSGNSQESVTEQDSKDSTYSLSSTLTLSKADYEKHKVY
ACEVTHQGLSSPVTKSFNRGEC.

>Vx9mur L04 Full length LC
(SEQ ID NO: 75)
DVFMTQTPLSLPVSLGDQASISCRSSQNIVQSNGNTYLEWYLQKPGQS

PKLLIYKVFHRFSGVPDRFSGSGSGTDFTLKISRVEAEDLGVYYCFQG

SHVPWTFGGGTKVEIKRTVAAPSVFIFPPSDEQLKSGTASVVCLLNNF

YPREAKVQWKVDNALQSGNSQESVTEQDSKDSTYSLSSTLTLSKADYE

KHKVYACEVTHQGLSSPVTKSFNRGEC.

Chimera and Human Heavy Chains

>Vx4murH01 Full length HC
(SEQ ID NO: 76)
EVQLQQSGPELVKPGASVKMSCKASGYTFTNYVIHWVKRRPGQGLEWI

GYIYPYNDGILYNEKFKGKATVTSDKSSTAYMDLSSLTSEDSAVYYC

TRGGYYVPDYWGQGTTLTVSSASTKGPSVFPLAPCSRSTSESTAALGC

LVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLF

PPKPKDTLMISRTPEVTCVVVDVSQEDPEVQFNWYVDGVEVHNAKTKP

REEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNH

YTQKSLSLSLGK.

>Vx4humH01 Full length HC
(SEQ ID NO: 77)
QVQLVQSGAEVKKPGASVQVSCKASGYTFTNYVIHWLRQAPGQGLEWM

GYIYPYNDGILYNEKFKGRVTMTSDTSISTAYMELSSLRSDDTAVYYC

ARGGYYVPDYWGQATLVTSSASTKGPSVFPLAPCSRSTSESTAALGC

LVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLF

PPKPKDTLMISRTPEVTCVVVDVSQEDPEVQFNWYVDGVEVHNAKTKP

REEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNH

YTQKSLSLSLGK.

>Vx8humH11 Full length HC
(SEQ ID NO: 78)
QVQLVQSGAEVKKPGASVQVSCKASGYSFTNYYIHWLRQAPGQGLEWM

GYIDPLNGDTTYNQKFKGRVTMTSDTSISTAYMELSSLRSDDTAVYYC

ARGGKRAMDYWGQATLVTSSASTKGPSVFPLAPCSRSTSESTAALGC

LVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLF

PPKPKDTLMISRTPEVTCVVVDVSQEDPEVQFNWYVDGVEVHNAKTKP

REEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQP

ENNYKTTPPVLDSDGSFFLYSRLTVDKSRWQEGNVFSCSVMHEALHNH

YTQKSLSLSLGK.

>Vx9humH12 Full length HC
(SEQ ID NO: 79)
QVQLVQSGAEVKKPGASVKVSCKASGYTFTNYWIHWVRQAPGQGLEWM

GYTDPRTDYTEYNQKFKDRVTMTRDTSTSTVYMELSSLRSEDTAVYYC

ARGGRVGLGYWGQGTLVTVSSASTKGPSVFPLAPCSRSTSESTAALGC

LVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTK

GQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHY

TQKSLSLSPGK.

>Vx9humH14 Full length HC
(SEQ ID NO: 80)
EVQLVQSGAEVKKPGESLKISCKGSGYTFTNYWIHWVRQMPGKGLEWM

GYTDPRTDYTEYNQKFKDQVTISADKSISTAYLQWSSLKASDTAMYYC

ARGGRVGLGYWGQGTLVTVSSASTKGPSVFPLAPCSRSTSESTAALGC

LVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTK

GQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHY

TQKSLSLSPGK.

>Vx9humH15 Full length HC
(SEQ ID NO: 81)
QVQLVQSGAEVKKPGSSVKVSCKASGYTFTNYWIHWVRQAPGQGLEWM

GYTDPRTDYTEYAQKFQGRVTITADESTSTAYMELSSLRSEDTAVYYC

ARGGRVGLGYWGQGTLVTVSSASTKGPSVFPLAPCSRSTSESTAALGC

LVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTK

GQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHY

TQKSLSLSPGK.

>Vx4humH02 Full length HC
(SEQ ID NO: 82)
QVQLVQSGAEVKKPGASVQVSCKASGYTFTNYVIHWLRQAPGQGLEWM

GYIYPYNDGILYNEKFKGRVTMTSDTSISTAYMELSSLRSDDTAVYYC

ARGGYYVYDYWGQATLVTSSASTKGPSVFPLAPCSRSTSESTAALGC

LVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx9humH13 Full length HC
(SEQ ID NO: 83)
QVQLVQSGAEVKKPGSSVKVSCKASGYTFTNYWIHWVRQAPGQGLEWM
GYTDPRTDYTEYNQKFKDRVTITADESTSTAYMELSSLRSEDTAVYYC
ARGGRVGLGYWGQGTLVTVSSASTKGPSVFPLAPCSRSTSESTAALGC
LVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTK
GQPREPQVYTLPPSREEMTKNQVSLTCLVKGFYPSDIAVEWESNGQPE
NNYKTTPPMLDSDGSFFLYSKLTVDKSRWQQGNVFSCSVMHEALHNHY
TQKSLSLSPGK.

>Vx8humH10 Full length HC
(SEQ ID NO: 84)
EVQLVQSGAEVKKPGESLKISCKGSGYSFTNYYIHWVRQMPGKGLEWM
GYIDPLNGDTTYSPSFQGQVTISADKSISTAYLQWSSLKASDTAMYYC
ARGGKRAMDYWGRGTLVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx4humH04 Full length HC
(SEQ ID NO: 85)
EVQLVQSGAEVKKPGESLKISCKGSGYTFTNYVIHWVRQMPGKGLEWM
GYIYPYNDGILYNEKFKGQVTISADKSISTAYLQWSSLKASDTAMYYC
ARGGYYVPDYWGQGTTVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx4humH05 Full length HC
(SEQ ID NO: 86)
QVQLVQSGAEVKKPGASVKVSCKASGYTFTNYVIHWVRQAPGQGLEWM
GYIYPYNDGILYNEKFKGRVTMTTDTSTSTAYMELRSLRSDDTAVYYC
ARGGYYVPDYWGQGTTVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx9humH16 Full length HC
(SEQ ID NO: 87)
EVQLVQSGAEVKKPGESLKISCKGSGYTFTNYWIHWVRQMPGKGLEWM
GYTDPRTDYTEYSPSFQGQVTISADKSISTAYLQWSSLKASDTAMYYC
ARGGRVGLGYWGQGTLVTVSSASTKGPSVFPLAPCSRSTSESTAALGC
LVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTK
GQPREPQVYTLPPSREEMTKNQVSLTCLVKGFYPSDIAVEWESNGQPE
NNYKTTPPMLDSDGSFFLYSKLTVDKSRWQQGNVFSCSVMHEALHNHY
TQKSLSLSPGK.

>Vx8humH06 Full length HC
(SEQ ID NO: 88)
QVQLVQSGAEVKKPGASVKVSCKASGYSFTNYYIHWVRQAPGQGLEWM
GYIDPLNGDTTYNQKFKGRVTMTRDTSTSTVYMELSSLRSEDTAVYYC
ARGGKRAMDYWGQGTLVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx8humH07 Full length HC
(SEQ ID NO: 89)
QVQLVQSGAEVKKPGSSVKVSCKASGYSFTNYYIHWVRQAPGQGLEWM
GYIDPLNGDTTYNQKFKGRVTITADESTSTAYMELSSLRSEDTAVYYC
ARGGKRAMDYWGQGTLVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx8humH08 Full length HC
(SEQ ID NO: 90)
EVQLVQSGAEVKKPGESLKISCKGSGYSFTNYYIHWVRQMPGKGLEWM
GYIDPLNGDTTYNQKFKGQVTISADKSISTAYLQWSSLKASDTAMYYC
ARGGKRAMDYWGQGTLVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx8humH09 Full length HC
(SEQ ID NO: 91)
QVQLVQSGAEVKKPGSSVKVSCKASGYSFTNYYIHWVRQAPGQGLEWM
GYIDPLNGDTTYAQKFQGRVTITADESTSTAYMELSSLRSEDTAVYYC
ARGGKRAMDYWGQGTLVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx8humH06 Full length HC
(SEQ ID NO: 92)
QVQLVQSGAEVKKPGASVKVSCKASGYSFTNYYIHWVRQAPGQGLEWM
GYIDPLNGDTTYNQKFKGRVTMTRDTSTSTVYMELSSLRSEDTAVYYC
ARGGKRAMDYWGQGTLVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx8mur-H03 Full length HC
(SEQ ID NO: 93)
EVQLQQSGPELMKPGASVKISCKASGYSFTNYYIHWVNQSHGKSLEWI
GYIDPLNGDTTYNQKFKGKATLTVDKSSSTAYMRLSSLTSADSAVYYC
ARGGKRAMDYWGQGTSVTVSSASTKGPSVFPLAPCSRSTSESTAALGC
LVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLF
PPKPKDTLMISRTPEVTCVVVDVSQEDPEVQFNWYVDGVEVHNAKTKP
REEQFNSTYRVVSVLTVLHQDWLNGKEYKCKVSNKGLPSSIEKTISKA
KGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNH
YTQKSLSLSLGK.

>Vx9mur-H04 Full length HC
(SEQ ID NO: 94)
QVQLQQFGAELAKPGASVQMSCKASGYTFTNYWIHWVKQRPGQGLEWI
GYTDPRTDYTEYNQKFKDKATLAADRSSSTAYMRLSSLTSEDSAVYYC
AGGGRVGLGYWGHGSSVTVSSASTKGPSVFPLAPCSRSTSESTAALGC
LVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTK
GQPREPQVYTLPPSREEMTKNQVSLTCLVKGFYPSDIAVEWESNGQPE
NNYKTTPPMLDSDGSFFLYSKLTVDKSRWQQGNVFSCSVMHEALHNHY
TQKSLSLSPGK.

>Vx8humH06 Full length HC
(SEQ ID NO: 95)
QVQLVQSGAEVKKPGASVKVSCKASGYSFTNYYIHWVRQAPGQGLEWM
GYIDPLNGDTTYNQKFKGRVTMTRDTSTSTVYMELSSLRSEDTAVYYC
ARGGKRAMDYWGQGTLVTVSSASTKGPSVFPLAPCSRSTSESTAALGC
LVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTK
GQPREPQVYTLPPSREEMTKNQVSLTCLVKGFYPSDIAVEWESNGQPE
NNYKTTPPMLDSDGSFFLYSKLTVDKSRWQQGNVFSCSVMHEALHNHY
TQKSLSLSPGK.

>Vx8humH07 Full length HC
(SEQ ID NO: 96)
QVQLVQSGAEVKKPGSSVKVSCKASGYSFTNYYIHWVRQAPGQGLEWM
GYIDPLNGDTTYNQKFKGRVTITADESTSTAYMELSSLRSEDTAVYYC
ARGGKRAMDYWGQGTLVTVSSASTKGPSVFPLAPCSRSTSESTAALGC
LVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFP
PKPKDTLMISRTPEVTCVVVDVSHEDPEVQFNWYVDGVEVHNAKTKPR
EEQFNSTFRVVSVLTVVHQDWLNGKEYKCKVSNKGLPAPIEKTISKTK
GQPREPQVYTLPPSREEMTKNQVSLTCLVKGFYPSDIAVEWESNGQPE
NNYKTTPPMLDSDGSFFLYSKLTVDKSRWQQGNVFSCSVMHEALHNHY
TQKSLSLSPGK.

>Vx8humH08 Full length HC (SEQ ID NO: 97)
EVQLVQSGAEVKKPGESLKISCKGSGYSFTNYYIHWVRQMPGKGLEWM

GYIDPLNGDTTYNQKFKGQVTISADKSISTAYLQWSSLKASDTAMYYC

ARGGKRAMDYWGQGTLVTVSSASTKGPSVFPLAPCSRSTSESTAALGC

LVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTK

GQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHY

TQKSLSLSPGK.

>Vx8humH09 Full length HC (SEQ ID NO: 98)
QVQLVQSGAEVKKPGSSVKVSCKASGYSFTNYYIHWVRQAPGQGLEWM

GYIDPLNGDTTYAQKFQGRVTITADESTSTAYMELSSLRSEDTAVYYC

ARGGKRAMDYWGQGTLVTVSSASTKGPSVFPLAPCSRSTSESTAALGC

LVKDYFPEPVTVSWNSGALTSGVHTFPAVLQSSGLYSLSSVVTVPSSN

FGTQTYTCNVDHKPSNTKVDKTVERKCCVECPPCPAPPVAGPSVFLFP

PKPKDTLMISRTPEVTCVVVDVSHEDPEVQFNWYVDGVEVHNAKTKPR

EEQFNSTFRVVSVLTVVHQDWLNGKEYKCKVSNKGLPAPIEKTISKTK

GQPREPQVYTLPPSREEMTKNQVSLTCLVKGFYPSDIAVEWESNGQPE

NNYKTTPPMLDSDGSFFLYSKLTVDKSRWQQGNVFSCSVMHEALHNHY

TQKSLSLSPGK.

>Vx4mur-ratL01 Full length LC (SEQ ID NO: 101)
DVLMTQTPLSLPVNLGDQASISCRSRQSIVHTNGNTYLGWFLQKPGQS

PKLLIYKVSNRFSGVPDRFSGSGSGTDFTLTISRVEAEDLGVYYCFQG

SHVPYTFGGGTKLEIKRADAAPTVSIFPPSMEQLTSGGATVVCFVNNF

YPRDISVKWKIDGSEQRDGVLDSVTDQDSKDSTYSMSSTLSLTKVEYE

RHNLYTCEVVHKTSSSPVVKSFNRNEC.

>Vx4mur-ratH01 Full length HC (SEQ ID NO: 102)
EVQLQQSGPELVKPGASVKMSCKASGYTFTNYVIHWVKRRPGQGLEWI

GYIYPYNDGILYNEKFKGKATVTSDKSSSTAYMDLSSLTSEDSAVYYC

TRGGYYVPDYWGQGTTLTVSSARTTAPSVYPLVPGCSGTSGSLVTLGC

LVKGYFPEPVTVKWNSGALSSGVHTFPAVLQSGLYTLSSSVTVPSSTW

SSQTVTCSVAHPATKSNLIKRIEPRRPKPRPPTDICSCDDNLGRPSVF

IFPPKPKDILMITLTPKVTCVVVDVSEEEPDVQFSWFVDNVRVFTAQT

QPHEEQLNGTFRVVSTLHIQHQDWMSGKEFKCKVNNKDLPSPIEKTIS

KPRGKARTPQVYTIPPPREQMSKNKVSLTCMVTSFYPASISVEWERNG

ELEQDYKNTLPVLDSDESYFLYSKLSVDTDSWMRGDIYTCSVVHEALH

NHHTQKNLSRSPGK.

>Vx4mur-rabL01 Full length LC (SEQ ID NO: 103)
DVLMTQTPLSLPVNLGDQASISCRSRQSIVHTNGNTYLGWFLQKPGQS

PKLLIYKVSNRFSGVPDRFSGSGSGTDFTLTISRVEAEDLGVYYCFQG

SHVPYTFGGGTKLEIKRDPVAPTVLIFPPAADQVATGTVTIVCVANKY

FPDVTVTWEVDGTTQTTGIENSKTPQNSADCTYNLSSTLTLTSTQYNS

HKEYTCKVTQGTTSVVQSFNRGDC.

>Vx4mur-rabH01 Full length HC (SEQ ID NO: 104)
EVQLQQSGPELVKPGASVKMSCKASGYTFTNYVIHWVKRRPGQGLEWI

GYIYPYNDGILYNEKFKGKATVTSDKSSSTAYMDLSSLTSEDSAVYYC

TRGGYYVPDYWGQGTTLTVSSGQPKAPSVFPLAPCCGDTPSSTVTLGC

LVKGYLPEPVTVTWNSGTLTNGVRTFPSVRQSSGLYSLSSVVSVTSSS

QPVTCNVAHPATNTKVDKTVAPSTCSKPTCPPPELLGGPSVFIFPPKP

KDTLMISRTPEVTCVVVDVSQDDPEVQFTWYINTNEQVRTARPPLREQ

QFNSTIRVVSTLPIAHQDWLRGKEFKCKVHNKALPAPIEKTISKARGQ

PLEPKVYTMGPPREELSSRSVSLTCMINGFYPSDISVEWEKNGKAEDN

YKTTPAVLDSDGSYFLYSKLSVPTSEWQRGDVFTCSVMHEALHNHYTQ

KSISRSPGK.

Example 2

Production of CD47 Antibodies

Chimeric antibodies disclosed herein comprise a mouse heavy chain variable domain and a light chain variable domain combined with a human kappa or human Fc IgG1, IgG1-N297Q, IgG2, IgG4, IgG4 S228P, and IgG4 PE constant domains, respectively. These were designed to incorporate a secretion signal and cloned into a mammalian expression system, and transfected into CHO cells to generate chimeric (murine-human) antibodies. The chimeric variants were expressed as full length IgG molecules, secreted into the medium, and purified using protein A.

As such, the humanized antibodies disclosed herein comprise frameworks derived from the human genome. The collection covers the diversity found in the human germ line sequences, yielding functionally expressed antibodies in vivo. The complementarity determining regions (CDRs) in the light and heavy chain variable regions of the murine and chimeric (murine-human) are described herein and were determined by following commonly accepted rules disclosed in "Protein Sequence and Structure Analysis of Antibody Variable Domains", In: *Antibody Engineering Lab Manual*, eds. S. Duebel and R. Kontermann, Springer-Verlag, Heidelberg (2001)). The human light chain variable domains were then designed. The humanized variable domains were then combined with a secretion signal and human kappa and human Fc IgG1, IgG1-N297Q, IgG2, IgG3, IgG4 S228P and IgG4 PE constant domains, cloned into a mammalian expression system, and transfected into CHO cells to generate humanized mAbs. The humanized variants were expressed as full length IgG molecules, secreted into the medium and purified using protein A.

A non-glycosylated version (IgG1-N297Q) was created by site directed mutagenesis of heavy chain position 297 to change the asparagine to glutamine (Human Fc IgG1-

N297Q, SEQ ID NO:54). An IgG4 variant was created by site-directed mutagenesis at position 228 to change the serine to proline thereby preventing in vivo Fab arm exchange. An IgG4 double mutant was created by site-directed mutagenesis at positions 228 (serine to proline) and 235 (leucine to glutamate) to prevent Fab arm exchange and to further reduce Fc effector function. IgG2, IgG3, IgG4 S228P, and IgG4 PE isotypes were constructed by cloning the heavy chain variable domain in frame with the human IgG2, IgG3, IgG4 S228P, and IgG4PE constant domains (Human Fc-IgG2, SEQ ID NO:55 Human Fc-IgG3, SEQ ID NO:56; Human Fc-IgG4 S228P, SEQ ID NO:58; and Human Fc-IgG4 PE, SEQ ID NO:59).

Example 3

Binding of CD47 Monoclonal Antibodies (mAbs)

The binding of chimeric (murine-human) and humanized antibodies of the present disclosure was determined by ELISA using OV10 cells transfected with human CD47 (OV10 hCD47) or using freshly isolated human red blood cells (hRBCs), which display CD47 on their surface (Kamel et al. (2010) *Blood. Transfus.* 8(4):260-266).

Binding activities of VLX4, VLX8, and VLX9 chimeric (murine-human) and humanized mAbs were determined using a cell-based ELISA assay with human OV10 hCD47 cells expressing cell surface human CD47. OV10 hCD47 cells were grown in IMDM medium containing 10% heat inactivated fetal bovine serum (BioWest; S01520). One day before assay, 3×10⁴ cells were plated in 96 well cell bind plates (Corning #3300, VWR #66025-626) and were 95-100% confluent at the time of assay. Cells were washed and various concentrations of purified antibodies added in IMDM 37° C. for 1 hr in 95% $O_2$/5% $CO_2$. Cells were then washed with media and incubated for an additional hour at 37° C. with HRP labeled secondary anti-human antibody (Promega) diluted 1/2500 in media. Cells were washed three times with PBS, and the peroxidase substrate 3,3',5,5'-tetramethylbenzidine is added (Sigma; Catalog #T4444). Reactions were terminated by the addition of HCl to 0.7N, and absorbance at 450 nM is determined using a Tecan model Infinite M200 plate reader. The apparent binding affinities of these clones to human OV10 hCD47 cells was determined by non-linear fit (Prism GraphPad software).

Binding activities of chimeric (murine-human) and humanized VLX4, VLX8, and VLX9 mAbs to human CD47 on hRBCs were also determined using flow cytometry. hRBCs were incubated for 60 min on at 37° C. with various concentrations of the chimeric or humanized antibodies in a solution of phosphate buffered saline, pH 7.2, 2.5 mM EDTA (PBS+E). Cells were then washed with cold PBS+E, and incubated for an additional hour on ice with FITC labeled donkey anti-human antibody (Jackson Immuno Research Labs, West Grove, Pa.; Catalogue #709-096-149) in PBS+E. Cells were washed with PBS+E, antibody binding analyzed using a C6 Accuri Flow Cytometer (Becton Dickinson) and apparent binding affinities determined by non-linear fit (Prism GraphPad software) of the median fluorescence intensities at the various antibody concentrations.

All of the VLX4 chimeric (murine-human) mAbs bound to human OV10 hCD47 tumor cells with apparent affinities in the picomolar (pM) range (Table 1).

Figure 1A:
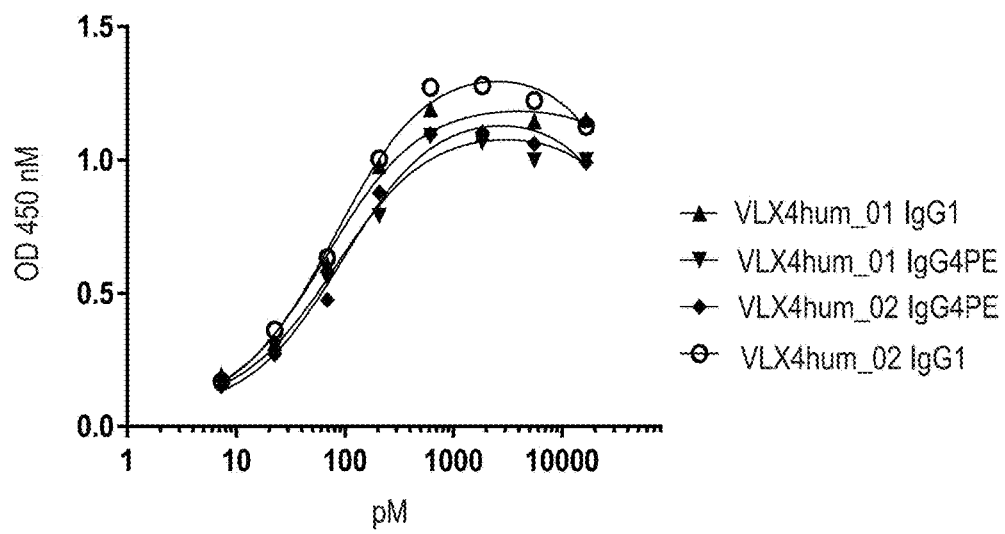
FIG. 1A. Binding of VLX4 Humanized mAbs to Human OV10 Cells Expressing human CD47. Binding of VLX4 humanized mAbs (VLX4hum_01 IgG1, VLX4hum_02 IgG1, VLX4hum_01 IgG4 PE, and VLX4hum_02 IgG4 PE) to human CD47 was determined using a OV10 cell line expressing human CD47 (OV10 hCD47) cell-based ELISA. OV10 hCD47 cells were plated into 96 well plates and were confluent at the time of assay. Various concentrations of mAbs were added to the cells for 1 hr. Cells were washed and then incubated with HRP-labelled secondary antibody for 1 hr followed by addition of peroxidase substrate.
Figure 1B:
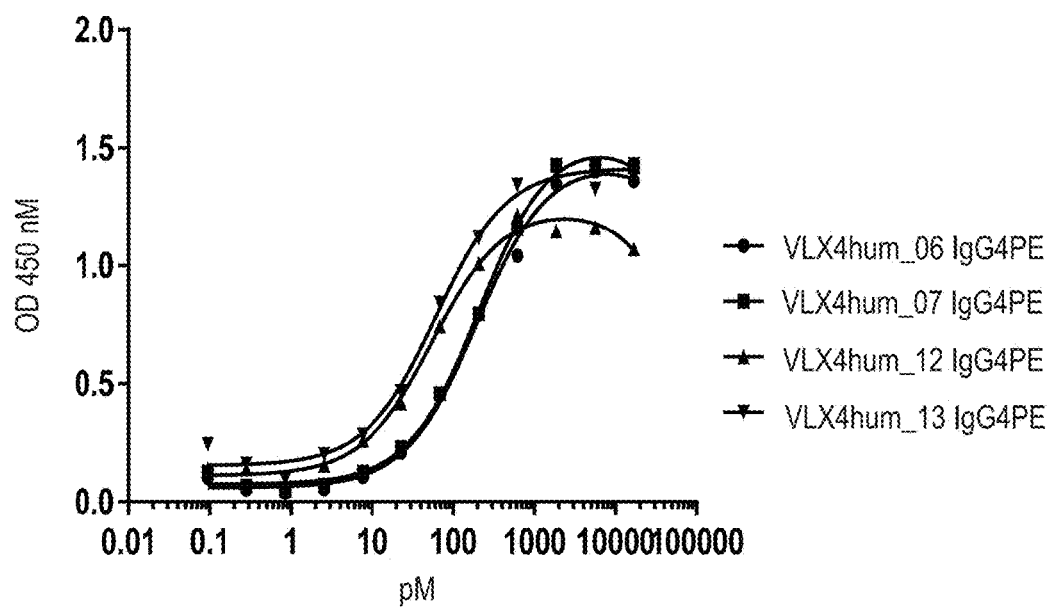
FIG. 1B. Binding of VLX4 Humanized mAbs to Human OV10 Cells Expressing human CD47. Binding of VLX4 humanized mAbs (VLX4hum_06 IgG4 PE, VLX4hum_07 IgG4 PE, VLX4hum_12 IgG4 PE, and VLX4hum_13 IgG4 PE) to human CD47 was determined using an OV10 CD47 cell-based ELISA. OV10 hCD47 cells were plated into 96 well plates and were confluent at the time of assay. Various concentrations of VLX4 representative mAbs were added to the cells for 1 hr. Cells were washed and then incubated with HRP-labelled secondary antibody for 1 hr followed by addition of peroxidase substrate.

Similarly, the humanized VLX4 mAbs bound to human OV10 hCD47 tumor cells in a concentration-dependent manner (FIG. 1A and FIG. 1B) with apparent affinities ranging from the picomolar to low nanomolar range (Table 2).

All of the chimeric VLX4 mAbs bound to human RBCs with apparent Kd values in the picomolar range and these were similar to the $K_d$ values obtained for OV10 hCD47 tumor cells by ELISA (Table 1).

Figure 2A:
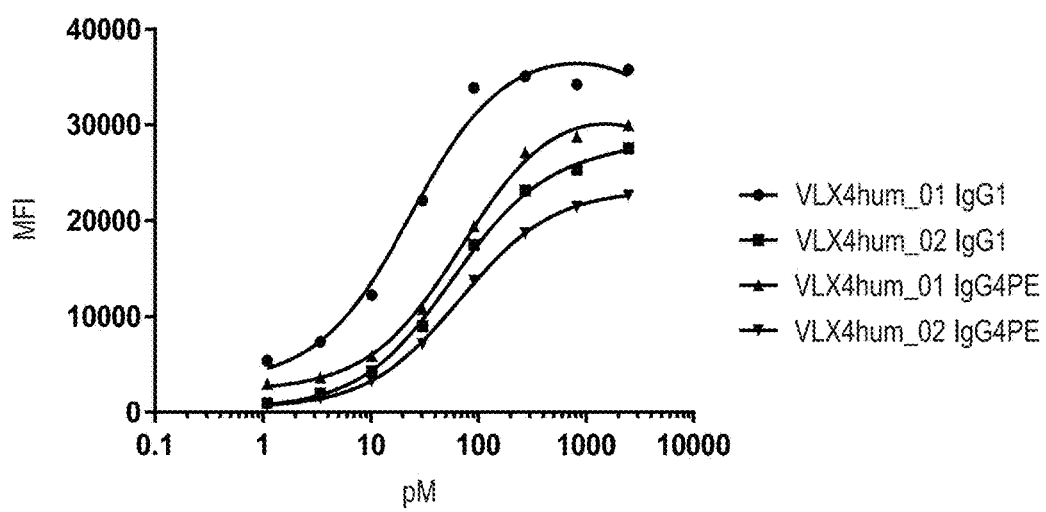
FIG. 2A. Binding of VLX4 Humanized mAbs to Human RBCs (hRBCs). Binding of VLX4 humanized mAbs (VLX4hum_01 IgG1, VLX4hum_02 IgG1, VLX4hum_01 IgG4 PE, and VLX4hum_02 IgG4PE) to human CD47 was determined using freshly isolated hRBCs. hRBCs were incubated for 60 minutes at 37° C. with various concentrations of VLX4 mAbs, washed and incubated for 1 hr with FITC-labeled donkey anti-human antibody. Cells were washed and antibody binding measured using flow cytometry.
Figure 2B:
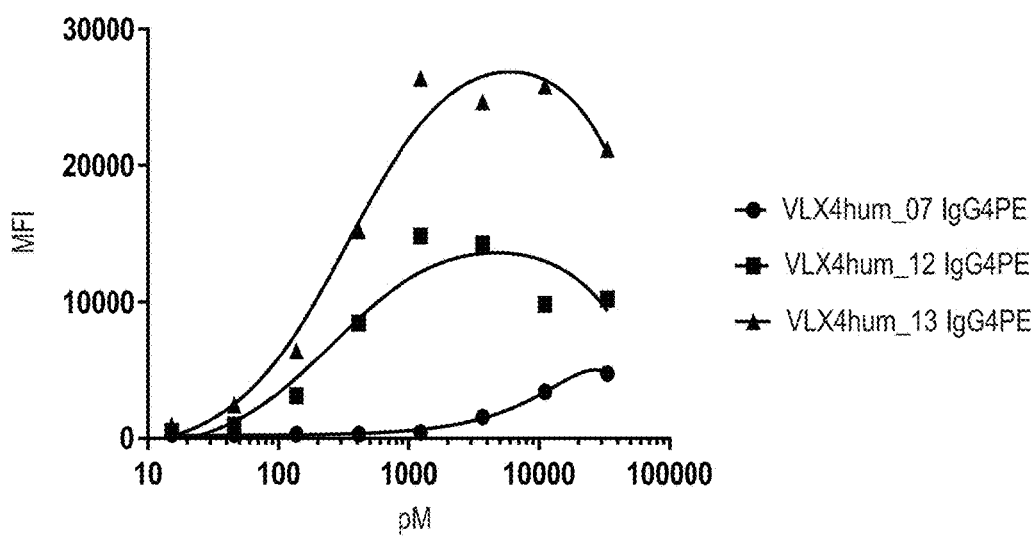
FIG. 2B. Binding of VLX4 Humanized mAbs to Human RBCs. Binding of VLX4 humanized mAbs (VLX4hum_07 IgG4 PE, VLX4hum_12 IgG4 PE, and VLX4hum_13 IgG4 PE) to human CD47 was determined using freshly isolated hRBCs. hRBCs were incubated for 60 minutes at 37° C. with various concentrations of VLX4 mAbs, washed and incubated for 1 hr with FITC-labeled donkey anti-human antibody. Cells were washed and antibody binding measured using flow cytometry.

The humanized VLX4 mAbs VLX4hum_01 IgG1 N297Q, VLX4hum_02 IgG1 N297Q, VLX4hum_01 IgG4 PE, VLX4hum_02 IgG4 PE, VLX4hum_12 IgG4 PE, and VLX4hum_13 IgG4 bound to human RBCs with Kd values similar to the values obtained for OV10 hCD47 tumor cells whereas VLX4hum_06 IgG4 PE and VLX4hum_07 IgG4 PE exhibited reduced binding to hRBCs (FIG. 2A, FIG. 2B, and Table 2). This differential binding of the humanized mAbs to tumor cells and RBCs was unexpected as the VLX4 IgG4PE chimeric mAb bound with similar apparent Kd values to both tumor and RBC CD47 (Table 1).

As shown in Table 1, all of the VLX8 chimeric (murine-human) mAbs bound to human OV10 hCD47 tumor cells in a concentration-dependent manner with apparent affinities in the picomolar (pM) range.

Figure 3A:
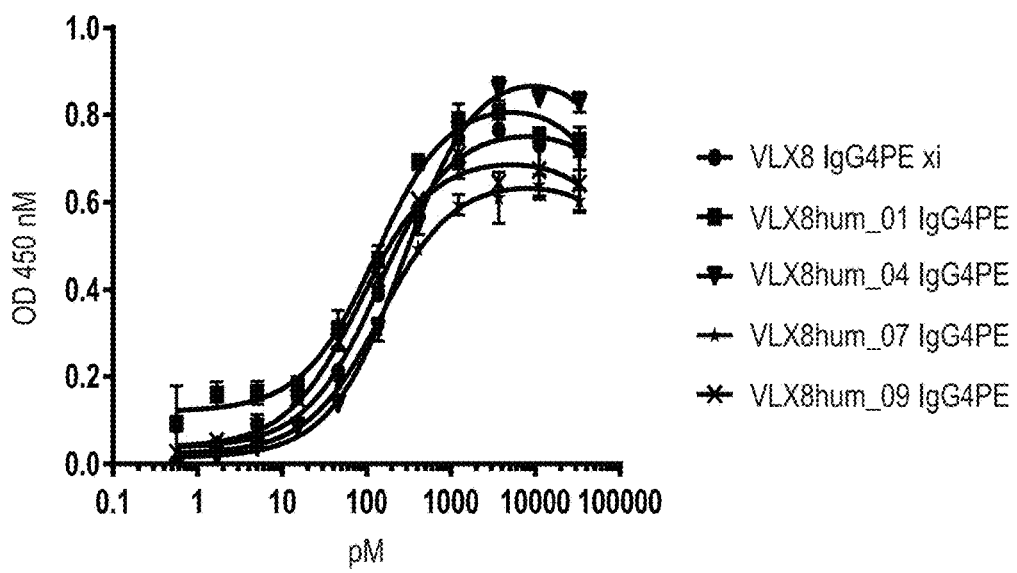
FIG. 3A. Binding of VLX8 Humanized mAbs to Human OV10 hCD47 Cells. Binding of VLX8 IgG4PE chimera (xi) or humanized mAbs (VLX8hum_01 IgG4PE, VLX8hum_04 IgG4 PE, VLX8hum_07 IgG4 PE, and VLX8hum_09 IgG4 PE) to human CD47 was determined using an OV10 hCD47 cell-based ELISA. OV10 hCD47 cells were plated into 96 well plates and were confluent at the time of assay. Various concentrations of VLX8 representative mAbs were added to the cells for 1 hr. Cells were washed and then incubated with HRP-labelled secondary antibody for 1 hr followed by addition of peroxidase substrate.
Figure 3B:
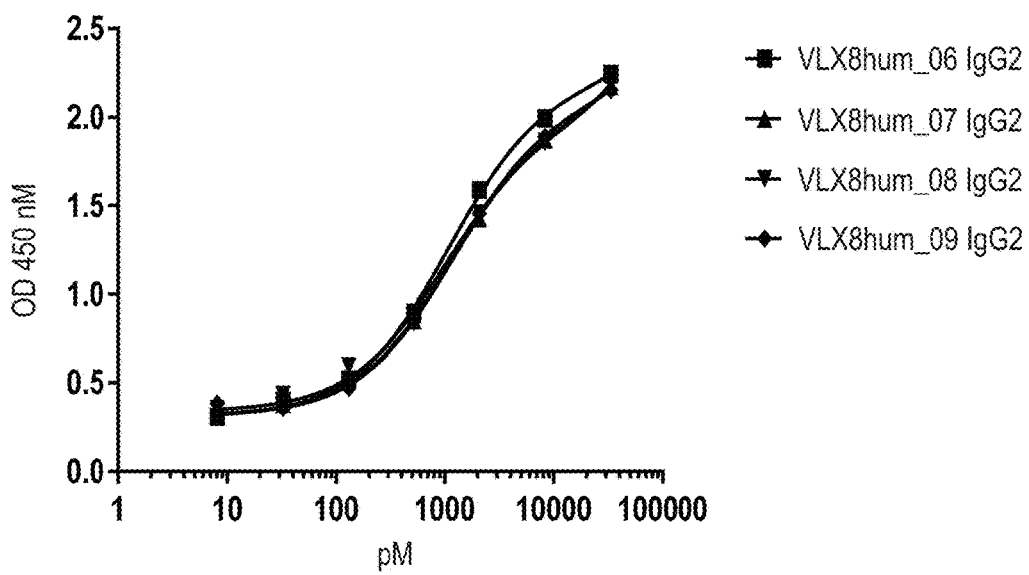
FIG. 3B. Binding of VLX8 Humanized mAbs to Human OV10 hCD47 Cells. Binding of VLX8 chimera or humanized mAbs (VLX8hum_06 IgG2, VLX8hum_07 IgG2, VLX8hum_08 IgG2, and VLX8hum_09 IgG2) to human CD47 was determined using an OV10 hCD47 cell-based ELISA. OV10 hCD47 cells were plated into 96 well plates and were confluent at the time of assay. Various concentrations of VLX8 representative mAbs were added to the cells for 1 hr. Cells were washed and then incubated with HRP-labelled secondary antibody for 1 hr followed by addition of peroxidase substrate.

Similarly, the humanized VLX8 mAbs bound to human OV10 hCD47 tumor cells in a concentration-dependent manner (FIG. 3A and FIG. 3B) with apparent affinities in the picomolar range (Table 2).

All of the VLX8 chimeric mAbs bound to hRBCs with apparent $K_d$ values in the picomolar range and these were similar to the $K_d$ values obtained for OV10 hCD47 tumor cells by ELISA (Table 1).

The VLX8 humanized mAbs VLX8hum_01 IgG4 PE, VLX8hum_02 IgG4 PE, VLX8hum_03 IgG4 PE, VLX8hum_04 IgG4 PE, VLX8hum_05 IgG4 PE, and VLX8hum_06 IgG4 PE, VLX8hum_07 IgG4 PE, VLX8hum_08 IgG4 PE, VLX8hum_09 IgG4 PE, VLX8hum_11 IgG4 PE, VLX8hum_06 IgG2, VLX8hum_07 IgG2, VLX8hum_08 and VLX8hum_09 IgG2 IgG2 bound to human RBCs with Kd values similar to the values obtained for OV10 hCD47 tumor cells whereas VLX8hum_10 IgG4 PE exhibited reduced, but measurable binding to hRBCs (FIG. 4A, FIG. 4B, and Table 2). This differential binding of the humanized mAbs to tumor cells and RBCs was unexpected as the VLX8 IgG4PE chimeric mAb bound with similar apparent Kd values to both tumor and RBC CD47 (Table 1).

Table 1 shows the apparent binding affinities of VLX9 murine-human chimeric mAbs to human OV10 hCD47 cells and to human RBCs. All of the chimeric mAbs bound to OV10 hCD47 tumor cells with apparent Kd values in the picomolar range. Similarly, the humanized VLX9 mAbs bound to human OV10 hCD47 tumor cells in a concentration-dependent manner (FIG. 5A and FIG. 5B) with apparent affinities in the picomolar to nanomolar range (Table 2).

All of the VLX9 chimeric mAbs bound to hRBCs with apparent $K_d$ values in the picomolar range and these were similar to the $K_d$ values obtained for OV10 hCD47 tumor cells by ELISA (Table 1). In contrast to the chimeric mAbs, the VLX9 humanized mAbs VLX9hum_01 IgG2, VLX9hum_02 IgG2 and VLX9hum_07 IgG2 exhibited reduced but measurable binding to human RBCs (FIG. 6, Table 2). Humanized mAbs VLX9hum_03, 04, 05, 06, 08, 09 and 10 IgG2 exhibited no measurable binding to RBCs (Table 2). This differential binding of the humanized mAbs to tumor cells and RBCs was unexpected as the VLX9 IgG2 chimeric mAbs all bound with similar apparent Kd values to both tumor and RBC CD47 (Table 1).

TABLE 1

Binding of VLX4, VLX8, and VLX9 Chimeric (xi) mAbs to OV10 hCD47 Cells and Human Red Blood Cells (hRBCs).

| | $V_H$ (SEQ ID NO:) | $V_L$ (SEQ ID NO:) | Kd (pM) OV10 hCD47 Cell-based ELISA | Kd (pM) hRBC | HA hRBC |
|---|---|---|---|---|---|
| VLX4 IgG1 (xi) | 21 | 41 | 315 | 104 | Yes |
| VLX4 IgG1 N297Q (xi) | 21 | 41 | 258 | 92 | Yes |
| VLX4 IgG2 (xi) | 21 | 41 | 431 | 184 | Yes |
| VLX4 IgG4 S228P (xi) | 21 | 41 | 214 | 99 | No |
| VLX4 IgG4 PE (xi) | 21 | 41 | 225 | 303 | No |
| VLX8 IgG1 N297Q (xi) | 28 | 46 | 42 | 91 | Yes |
| VLX8 IgG4 PE (xi) | 28 | 46 | 56 | 77 | Yes |
| VLX9 IgG1 (xi) | 35 | 50 | 280 | 381 | Yes |
| VLX9 IgG1 N297Q (xi) | 35 | 50 | 275 | 190 | Yes |
| VLX9 IgG2 (xi) | 35 | 50 | 880 | 742 | Yes |
| VLX9 IgG4 PE (xi) | 35 | 50 | 293 | 126 | Yes |

TABLE 2

Binding of VLX4, VLX8, and VLX9 Humanized mAbs to Human OV10 hCD47 and Human Red Blood Cells (hRBCs).

| | Kd (pM) OV10 hCD47 Cell-based ELISA | Kd (pM) hRBC | HA hRBC |
|---|---|---|---|
| VLX4hum_01 IgG1 | 73 | 23 | Yes |
| VLX4hum_02 IgG1 | 80 | 70 | Yes |
| VLX4hum_01 IgG4 PE | 82 | 63 | No |
| VLX4hum_02 IgG4 PE | 95 | 75 | R*** |
| VLX4hum_06 IgG4 PE | 196 | >66,000** | Yes |
| VLX4hum_07 IgG4 PE | 209 | >66,000** | Yes |
| VLX4hum_12 IgG4 PE | 56 | 263 | Yes |
| VLX4hum_13 IgG4 PE | 62 | 340 | Yes |
| VLX8hum_01 IgG4 PE | 54 | 209 | No |
| VLX8hum_02 IgG4 PE | 50 | 221 | No |
| VLX8hum_03 IgG4 PE | 67 | 183 | No |
| VLX8hum_04 IgG4 PE | 49 | 119 | No |
| VLX8hum_05 IgG4 PE | 68 | 264 | No |
| VLX8hum_06 IgG4 PE | 61 | 274 | Yes |
| VLX8hum_07 IgG4 PE | 24 | 241 | Yes |
| VLX8hum_08 IgG4 PE | 97 | 217 | Yes |
| VLX8hum_09 IgG4 PE | 82 | 336 | Yes |
| VLX8hum_10 IgG4 PE | 183 | >33,000** | Yes |
| VLX8hum_11 IgG4 PE | 90 | 18 | No |
| VLX8hum_06 IgG2 | 403 | 246 | Yes |
| VLX8hum_07 IgG2 | 460 | 671 | Yes |
| VLX8hum_08 IgG2 | 464 | 820 | Yes |
| VLX8hum_09 IgG2 | 680 | 1739 | Yes |
| VLX9hum_01 IgG2 | 162 | 1653** | N |
| VLX9hum_02 IgG2 | 227 | 4103** | N |
| VLX9hum_03 IgG2 | 606 | *NB | N |
| VLX9hum_04 IgG2 | 823 | *NB | N |
| VLX9hum_05 IgG2 | 6372 | *NB | N |
| VLX9hum_06 IgG2 | 547 | *NB | N |
| VLX9hum_07 IgG2 | 341 | >66,000** | ***R |
| VLX9hum_08 IgG2 | 688 | *NB | N |
| VLX9hum_09 IgG2 | 8340 | *NB | N |
| VLX9hum_10 IgG2 | 12232 | *NB | N |

*NB—No binding detected at mAb concentration up to 100 µg/mL.
**Reduced RBC binding.
***R—Reduced hemagglutination.

Cross-species binding of humanized VLX4, VLX8, and VLX9 mAbs was determined using flow cytometry. Mouse, rat, rabbit or cynomolgus monkey RBCs were incubated for 60 min on at 37° C. with various concentrations of the humanized antibodies in a solution of phosphate buffered saline, pH 7.2, 2.5 mM EDTA (PBS+E). Cells were then washed with cold PBS+E, and incubated for an additional hr on ice with FITC labeled donkey anti-human antibody (Jackson Immuno Research Labs, West Grove, Pa.; Catalogue #709-096-149) in PBS+E. Cells were washed with PBS+E, and antibody binding analyzed using a C6 Accuri Flow Cytometer (Becton Dickinson).

Table 3 shows the apparent binding affinities of the humanized VLX4 and VLX8 mAbs to RBCs from mouse, rat, and cynomolgus monkey determined by non-linear fit (Prism GraphPad software) of the median fluorescence intensities at various antibody concentrations. This data demonstrates that humanized VLX4 and VLX8 mAbs bind to mouse, rat, rabbit (data not shown) and cynomolgus monkey RBCs with apparent Kd values in the picomolar to nanomolar range (Table 4).

TABLE 3

Binding of VLX4 and VLX8 Humanized mAbs to mouse and rat RBCs.

| | Kd (pM) Mouse RBC | Kd (pM) Rat RBC | Kd (pM) Cynomolgus Monkey RBC |
|---|---|---|---|
| VLX4hum_01 IgG4 PE | 16166 | 29917 | 23 |
| VLX4hum_07 IgG4 PE | 21340 | 17610 | 4313 |
| VLX8hum_11 IgG4PE | 2473 | 10921 | 76 |

Example 4

CD47 Antibodies Block CD47/SIRPα Binding

To assess the effect of humanized CD47 mAbs on binding of CD47 to SIRPα in vitro the following method is employed using the binding of fluorescently-labelled SIRPα-Fc fusion protein to CD47 expressing Jurkat T cells.

SIRPα-Fc fusion protein (R&D Systems, cat #4546-SA) was labelled using an Alexa Fluor® antibody labelling kit (Invitrogen Cat No. A20186) according to the manufacturers specifications. $1.5 \times 10^6$ Jurkat T cells were incubated with humanized mAbs (5 µg/ml), a human control antibody in RPMI containing 10% media or media alone for 30 min at 37° C. An equal volume of fluorescently labeled SIRPα-Fc fusion protein was added and incubated for an additional 30 min at 37° C. Cells were washed once with PBS and the amount of labelled SIRPα-Fc bound to the Jurkat T cells analyzed by flow cytometry.

As shown in FIG. 7, the humanized VLX4, VLX8 and VLX9 mAbs, blocked the interaction of CD47 expressed on the Jurkat T cells with SIPRα, while the human control antibody (which does not bind to CD47) or media alone, did not block the CD47/SIRPα interaction.

Example 5

CD47 Antibodies Increase Phagocytosis

To assess the effect of chimeric (murine-human) and humanized VLX4, VLX8, and VLX9 CD47 mAbs on phagocytosis of tumor cells by macrophages in vitro the following method is employed using flow cytometry (Willingham et al. (2012) *Proc Natl Acad Sci USA* 109(17): 6662-7 and Tseng et al. (2013) *Proc Natl Acad Sci USA* 110(27):11103-8).

Human derived macrophages were derived from leukapheresis of healthy human peripheral blood and incubated in AIM-V media (Life Technologies) for 7-10 days. For the in vitro phagocytosis assay, macrophages were re-plated at a concentration of 1×10⁴ cells per well in 100 ul of AIM-V media in a 96-well plate and allowed to adhere for 24 hrs. Once the effector macrophages adhered to the culture dish, the target human cancer cells (Jurkat) were labeled with 1 µM 5(6)-Carboxyfluorescein diacetate N-succinimidyl ester (CFSE; Sigma Aldrich) and added to the macrophage cultures at a concentration of 5×10⁴ cells in 1 ml of AIM-V media (5:1 target to effector ratio). VLX4, VLX8, and VLX9 CD47 mAbs (1 µg/ml) were added immediately upon mixture of target and effector cells and allowed to incubate at 37° C. for 2-3 hours. After 2-3 hrs, all non-phagocytosed cells were removed and the remaining cells washed three times with phosphate buffered saline (PBS; Sigma Aldrich). Cells were then trypsinized, collected into microcentrifuge tubes, and incubated in 100 ng of allophycocyanin (APC) labeled CD14 antibodies (BD Biosciences) for 30 minutes, washed once, and analyzed by flow cytometry (Accuri C6; BD Biosciences) for the percentage of CD14⁺ cells that were also CFSE indicating complete phagocytosis.

As shown in FIG. 8, the VLX4 chimeric (murine-human) mAbs VLX4 IgG1, VLX4 IgG1 N297Q, VLX4 IgG4 PE, and VLX4 IgG4 S228P increased phagocytosis of Jurkat cells by human macrophages by blocking the CD47/SIRPα interaction and this enhanced phagocytosis is independent of Fc function.

Similarly, as shown in FIG. 9A and FIG. 9B, VLX4hum_01 IgG1, VLX4hum_01 IgG4 PE, VLX4hum_06 IgG4 PE, VLX4hum_07 IgG4 PE, VLX4hum_12 IgG4 PE, and VLX4hum_13 IgG4 PE increased phagocytosis of Jurkat cells by human macrophages by blocking the CD47/SIRPα interaction.

As shown in FIG. 10A, the VLX8 chimeric (murine-human) mAbs VLX8 IgG1 N297Q and VLX8 IgG4 PE increase phagocytosis of Jurkat T cells by human macrophages via blocking the CD47/SIRPα interaction and this enhanced phagocytosis is independent of Fc function.

Similarly, as shown in FIG. 10B, VLX8hum_01 IgG4 PE, VLX8hum_03 IgG4 PE, VLX8hum_07 IgG4 PE, VLX8hum_08 IgG4 PE, and VLX8hum_09 IgG4 PE increased phagocytosis of Jurkat cells by human macrophage by blocking the CD47/SIRPα interaction and this enhanced phagocytosis is independent of Fc function As shown in FIG. 11A, the VLX9 IgG1N297Q, VLX9 IgG2 and VLX9 IgG4 PE chimeric mAbs all increased phagocytosis of Jurkat T cells by human macrophages by blocking the CD47/SIRPα interaction and this enhanced phagocytosis is independent of Fc effector function. Similarly as shown in FIG. 11B, all of the humanized VLX9 IgG2 mAbs increased phagocytosis of Jurkat T cells.

Example 6

Induction of Cell Death by Soluble CD47 Antibodies

Some soluble CD47 antibodies have been shown to induce selective cell death of tumor cells. This additional property of selective toxicity to cancer cells is expected to have advantages compared to mAbs that only block SIRPα binding to CD47.

Induction of cell death by soluble anti-CD47 mAbs is measured in vitro (Manna et al. (2003) *J. Immunol.* 107 (7): 3544-53). For the in vitro cell death assay, 1×10⁵ transformed human T cells (Jurkat T cells) were incubated with soluble humanized VLX4, VLX8, and VLX9 CD47 mAbs (1 µg/ml) for 24 hrs at 37° C. As cell death occurs, mitochondrial membrane potential is decreased, the inner leaflet of the cell membrane is inverted, exposing phosphatidylserines (PS), and propidium iodide (PI) is able to incorporate into nuclear DNA. In order to detect these cellular changes, cells were then stained with fluorescently labeled annexin V and PI or 7-aminoactinomycin D (7-AAD) (BD Biosciences) and the signal detected using an Accuri C6 flow cytometer (BD Biosciences). The increase in PS exposure is determined by measuring the percent increase in annexin V signal and the percent of dead cells by measuring the percent increase in PI or 7-AAD signal. Importantly for therapeutic purposes, these mAbs induce cell death of tumor cells directly and do not require complement or the intervention of other cells (e.g., NK cells, T cells, or macrophages) to kill. Thus, the mechanism is independent of both other cells and of Fc effector function. Therefore, therapeutic antibodies developed from these mAbs can be engineered to reduce Fc effector functions such as ADCC and CDC and thereby limit the potential for side effects common to humanized mAbs with intact Fc effector functions.

As shown in FIG. 12A and FIG. 12B, the soluble VLX4 humanized mAbs induced cell death of Jurkat T ALL cells as measured by increased annexin V staining and 7-AAD staining (not shown). The humanized mAbs VLX4hum_01 IgG1, VLX4hum_01 IgG4 PE, VLX4hum_02 IgG1, VLX4hum_02 IgG4 PE, VLX4hum_06 IgG4 PE, VLX4hum_07 IgG4 PE, VLX4hum_12 IgG4 PE, and VLX4hum_13 IgG4 PE caused cell death. In contrast, the humanized mAbs VLX4hum_08 IgG4 PE and VLX4hum_11 IgG4 PE did not cause cell death of Jurkat T cells. Induction of cell death and the promotion of phagocytosis of susceptible cancer cells imparts an additional desirable antibody property and therapeutic benefit in the treatment of cancer.

As shown in FIG. 13A and FIG. 13B, the soluble VLX8 chimeric and humanized mAbs induced cell death of Jurkat T ALL cells as measured as measured by increased annexin V staining and 7-AAD staining (not shown). The chimeric mAbs, VLX8 IgG1 N297Q (xi) and VLX8 IgG4 PE, and the humanized mAbs, VLX8hum_07 IgG4 PE and VLX8hum_08 IgG4 PE, induced cell death of Jurkat T ALL cells. In contrast, the humanized mAbs VLX8hum_02 IgG4 PE and VLX8hum_04 IgG4 PE did not cause cell death of Jurkat T cells. Induction of cell death and the promotion of phagocytosis of susceptible cancer cells imparts an additional desirable antibody property and therapeutic benefit in the treatment of cancer.

As shown in FIG. 14A, the soluble VLX9 chimeric antibodies induced cell death of Jurkat cells as measured by increased annexin V and 7-AAD staining (not shown). In addition as shown in FIG. 14B, the chimeric VLX9 IgG2xi mAb and the humanized mAbs VLX9hum_06 IgG2, VLX9hum_07 IgG2, VLX9hum_08 IgG2, and VLX9hum_09 IgG2 induced cell death of Jurkat cells (greater than 2-fold increase in annexin V staining). In contrast, the humanized mAbs VLX9hum_01 IgG2, VLX9hum_02 IgG2, VLX9hum_03 IgG2, VLX9hum_04 IgG2, VLX9hum_05 IgG2 and VLX9hum_010 IgG2 did not cause cell death of Jurkat cells. Induction of cell death and the promotion of phagocytosis of susceptible cancer cells imparts an additional desirable antibody property and therapeutic benefit in the treatment of cancer.

Example 7

Hemagglutination of Human Red Blood Cells (hRBCs)

Many CD47 antibodies, including B6H12, BRIC126, MABL1, MABL2, CC2C6, 5F9, have been shown to cause hemagglutination (HA) of washed RBCs in vitro or in vivo (Petrova P. et al. *Cancer Res* 2015; 75(15 Suppl): Abstract nr 4271; U.S. Pat. No. 9,045,541; Uno et al. *Oncol Rep*. 17: 1189-94, 2007; Kikuchi et al. *Biochem Biophys Res. Commun*. 315: 912-8, 2004; Sikic B. et al. *J Clin Oncol* 2016; 34 (suppl; abstract 3019)). Hemagglutination of hRBCs was assessed following incubation of hRBCs with various concentrations of chimeric and humanized VLX4, VLX8, and VLX9 mAbs in vitro essentially as described by Kikuchi et al. *Biochem Biophys Res. Commun* (2004) 315:912-918. Blood was obtained from healthy donors, diluted (1:50) in PBS/1 mM EDTA/BSA and washed 3 times with PBS/EDTA/BSA. hRBCs were added to U-bottomed 96 well plates with equal volumes of the antibodies (75 µl of each) and incubated for 3 hrs at 37° C. and overnight at 4° C.

As shown in FIG. 15A and Tables 1 and 2, The VLX4hum_01 IgG1 N297Q caused hemagglutination of hRBCs, whereas the humanized VLX4hum_01 IgG4 PE mAb did not (mAb concentrations 50 µg/ml to 0.3 ng/ml). The lack of hemagglutination by VLX4hum_01 IgG4 PE imparts an additional desirable antibody property and therapeutic benefit in the treatment of cancer.

As shown in FIG. 15B and Tables 1 and 2, the chimeric antibody VLX8 IgG4 PE (xi) and the humanized antibodies VLX8hum_08 IgG4 PE, VLX8hum_09 IgG4 PE, and VLX8hum_010 IgG4 PE caused hemagglutination of hRBCs, whereas the VLX8 humanized Abs VLX8hum_01 IgG4 PE, VLX8hum_02 IgG4 PE, VLX8hum_03 IgG4 PE and VLX8hum_11 IgG4 PE did not (mAb concentrations 50 µg/ml to 0.3 ng/ml).

The lack of hemagglutination by humanized antibodies VLX4hum_01 IgG4 PE, VLX8hum_01 IgG4 PE, VLX8hum_02 IgG4 PE, VLX8hum_03 IgG4 PE and VLX8hum_11 IgG4 PE imparts an additional desirable antibody property and a therapeutic benefit in the treatment of cancer.

As shown in FIG. 16A and FIG. 16B, The chimeric antibody VLX9 IgG2 caused hemagglutination of hRBCs, whereas all of the humanized VLX9 mAbs except for VLX9hum_07 IgG2, did not (at concentrations from 50 ug/ml to 0.3 pg/ml). However, the amount of hemagglutination caused by VLX9hum_07 was reduced compared to the VLX9 IgG2 chimeric mAb. Again, the lack of hemagglutination by the VLX9 humanized mAbs imparts an additional desirable antibody property and a therapeutic benefit in the treatment of cancer.

Example 8

Anti-Tumor Activity In Vivo

The purpose of this experiment was to demonstrate that VLX4, VLX8 and VLX9 humanized antibodies, exemplified by VLX4_07 IgG4PE, VLX8_10 IgG4PE and VLX9hum_08 IgG2, reduce tumor burden in vivo in a mouse xenograft model of lymphoma.

Raji human Burkitt's lymphoma cells (ATCC #CCL-86, Manassas, Va.) were maintained in RPMI-1640 (Lonza; Walkersville, Md.) supplemented with 10% Fetal Bovine Serum (FBS; Omega Scientific; Tarzana, Calif.) within a 5% $CO_2$ atmosphere. Cultures were expanded in tissue culture flasks.

Female NSG (NOD-Cg-Prkdc$^{scid}$Il2rg$^{tm1Wjl}$/SzJ) were obtained from Jackson Laboratory (Bar Harbor, Me.) at 5-6 weeks of age. Mice were acclimated prior to handling and housed in microisolator cages (Lab Products, Seaford, Del.) under specific pathogen-free conditions. Mice were fed Teklad Global Diet® 2920x irradiated laboratory animal diet (Envigo, Formerly Harlan; Indianapolis, Ind.) and provided autoclaved water ad libitum. All procedures were carried out under Institutional Animal Care and Use guidelines.

Female NSG mice were inoculated subcutaneously in the right flank with 0.1 mL of a 30% RPMI/70% Matrigel™ (BD Biosciences; Bedford, Mass.) mixture containing a suspension of 5×10$^6$ Raji tumor cells. Five days following inoculation, digital calipers were used to measure width and length diameters of the tumor. Tumor volumes were calculated utilizing the formula: tumor volume $(mm^3)=(a \times b^2/2)$ where 'b' is the smallest diameter and 'a' is the largest diameter. Mice with palpable tumor volumes of 31-74 mm$^3$ were randomized into 8-10/group and VLX9hum_08 or PBS (control) administration was initiated at this time. Mice were treated with 5 mg/kg of antibody 5×/week for 4 weeks by intraperitoneal injection. Tumor volumes and body weights were recorded twice weekly.

As shown in FIG. 17, treatment with the humanized VLX4hum_07 IgG4 PE significantly reduced tumor growth of the Raji tumors (p<0.05, two-way ANOVA), demonstrating anti-tumor efficacy in vivo.

As shown in FIG. 18, treatment with the humanized anti-CD47 mAb, VLX8hum_10 IgG4

PE significantly reduced (p<0.0001, two-way ANOVA) tumor growth of the Raji tumors, demonstrating anti-tumor efficacy in vivo.

As shown in FIG. 19, treatment with the humanized anti-CD47 mAb, VLX9hum_08 IgG2 significantly reduced (p<0.05, ANOVA) tumor growth of the Raji tumors, demonstrating anti-tumor efficacy in vivo.

Example 9

Effect on Circulating Red Blood Cell Parameters

The purpose of this experiment is to demonstrate that VLX9 humanized antibodies that do not bind to human RBC in vitro (Table 2), exemplified by hum1017_08 IgG2, do not cause a reduction in either hemoglobin (Hg) or circulating RBCs following administration to cynomolgus monkeys.

Female Chinese cynomolgus monkeys (Charles River Laboratories, Houston, Tex.) 2.5-3 kg were used in accordance with the Institutional Animal Care and Use guidelines. VLX9hum_08 IgG2 or vehicle (PBS) was administered as a 1 hour intravenous infusion on day 1 at a dose of 5 mg/kg and on day 18 at a dose of 15 mg/kg (3 animals/group). Hematological parameters were measured throughout the study on days −7, −3, 3, 8, 12, 18 (pre-dose), 20, 25, 29, 35 and 41 and compared/normalized to the means values of control animals. The pre-treatment RBC and Hg values on day 0 in the VLX9hum_08 IgG2 group were lower than the control group. Following treatment with either dose of VLX9hum_08 IgG2, there were minimal changes (<10%) in Hg (FIG. 20A) or RBC counts (FIG. 20B) compared to the control demonstrating that antibodies that do not bind to human RBCs in vitro do not cause a reduction in RBC hematological parameters when administered to cynomolgus monkeys.

Example 10

Immunohistochemical Staining of CD47

Localization of CD47 expression was determined in formalin-fixed, paraffin embedded (FFPE) blocks from patients with a number of types of cancer (obtained from commercial sources) using mouse/rabbit chimeric anti-CD47 mAbs. 3-4 micron sections were cut from FFPE blocks, deparaffinized and treated with antigen retrieval solution. Sections were then incubated with 4 µg/ml of the primary anti-CD47 mouse/rabbit chimeric mAbs for 1 hr and with an anti-rabbit HRP labeled secondary antibody for 20 minutes. The anti-CD47 antibody bound to human CD47 was visualized using the peroxidase substrate, 3,3',5,5'-tetramethylbenzidene. Sections were counterstained with hematoxylin and evaluated using standard light microscopy. As shown in FIG. 21, high CD47 expression was detected in human breast cancer tissue, as shown by dark areas denoted by arrows, using CD47 mouse/rabbit chimeric mAbs, exemplified by the VLX4 mouse/rabbit chimeric mAb. This demonstrates that these mAbs can be used for immunohistochemical localization of human CD47 in tumor tissue sections obtained from FFPE blocks in diagnostic assays.

Example 11

Antibodies to CD47 Regulate Nitric Oxide Signaling

TSP1 binding to CD47 activates the heterotrimeric G protein Gi, which leads to suppression of intracellular cyclic AMP (cAMP) levels. In addition, the TSP1/CD47 pathway opposes the beneficial effects of the nitric oxide (NO) pathway in all vascular cells. The NO pathway consists of any of three nitric oxide synthase enzymes (NOS I, NOS II and NOS III) that generate bioactive gas NO using arginine as a substrate. NO can act within the cell in which it is produced or in neighboring cells, to activate the enzyme soluble guanylyl cyclase that produces the messenger molecule cyclic GMP (cGMP). The proper functioning of the NO/cGMP pathway is essential for protecting the cardiovascular system against stresses including, but not limited to, those resulting from wounding, inflammation, hypertension, metabolic syndrome, ischemia, and ischemia-reperfusion injury (IRI). In the context of these cellular stresses, the inhibition of the NO/cGMP pathway by the TSP1/CD47 system exacerbates the effects of stress. This is a particular problem in the cardiovascular system where both cGMP and cAMP play important protective roles. There are many cases in which ischemia and reperfusion injury cause or contribute to disease, trauma, and poor outcomes of surgical procedures.

The purpose of these experiment will be to demonstrate that humanized anti-CD47 mAbs of the present disclosure exhibit the ability to reverse TSP1-mediated inhibition of NO-stimulated cGMP synthesis as, for example, described previously using mouse monoclonal antibodies to CD47 as disclosed by Isenberg et al. (2006) J. Biol. Chem. 281: 26069-80, or alternatively other downstream markers of or effects resulting from NO signaling, for example smooth muscle cell relaxation or platelet aggregation as described previously by Miller et al. (2010) Br J. Pharmacol. 159: 1542-1547.

The method employed that will be to measure cGMP as described by the manufacturer (CatchPoint Cyclic-GMP Fluorescent Assay Kit, Molecular Devices, Sunnyvale, Calif.). Jurkat JE6.1 cells (ATCC, Manassas, Va.; Catalog # TIB-152) or other cells types that retain the NO/cGMP signaling pathway when grown in culture and exhibit a robust and reproducible inhibitory response to TSP1 ligation of CD47 will be used. Cells will be grown in Iscove's modified Dulbeccco's medium containing 5% (v/v) heat inactivated fetal bovine serum (BioWest; Catalogue # S01520), 100 units/mL penicillin, 100 µg mL streptomycin (Sigma; Catalogue # P4222) at densities less than $1 \times 10^6$ cells/mL. For the cGMP assay, cells will be plated in 96 well tissue culture plates at a density of $1 \times 10^5$ cells/ml in Iscoves modified Dulbecco's medium containing 5% (v/v) heat inactivated fetal bovine serum (BioWest; Catalog # S01520), 100 units/mL penicillin, 100 µg/mL streptomycin (Sigma; #P4222) for 24 hours and then transferred to serum free medium overnight.

The humanized antibodies as disclosed herein, purified from transient transfections in CHO cells as described above in Example 3, as well as the control chimeric antibody, will then be added at a final concentration of 20 ng/ml, followed 15 minutes later by 0 or 1 µg/ml human TSP1 (Athens Research and Technology, Athens, Ga., Catalogue #16-20-201319). After an additional 15 minutes, the NO donor, diethylamine (DEA) NONOate (Cayman Chemical, Ann Arbor, Mich., Catalog #82100), will be added to half the wells at a final concentration of 1 µM. Five minutes later, the cells will be lysed with buffer supplied in the cGMP kit, and aliquots of each well assayed for cGMP content.

It is anticipated that some of the chimeric or humanized antibodies will reverse TSP1 inhibition of cGMP. Reversal will be complete (>80%) or intermediate (20%-80%). This reversal of TSP1 inhibition of cGMP will demonstrate that they have the ability to increase NO signaling and suggest utility in protecting the cardiovascular system against stresses including, but not limited to, those resulting from wounding, inflammation, hypertension, metabolic syndrome, ischemia, and ischemia-reperfusion injury (IRI). Additional assay systems, for example smooth muscle cell contraction, will also be expected to show that some of the chimeric or humanized antibody clones reverse the inhibitory actions of TSP on downstream effects resulting from the activation of NO signaling.

What is claimed is:

1. A monoclonal antibody or antigen-binding fragment thereof that specifically binds CD47 and comprises:
   a variable heavy chain CDR1 amino acid sequence (HCDR1) amino acid sequence set forth in SEQ ID NO:3;
   a variable heavy chain CDR2 amino acid sequence (HCDR2) amino acid sequence set forth in SEQ ID NO:6;
   a variable heavy chain CDR3 amino acid sequence (HCDR3) amino acid sequence set forth in SEQ ID NO:10;
   a variable light chain CDR1 amino acid sequence (LCDR1) amino acid sequence set forth in SEQ ID NO:14;
   a variable light chain CDR2 amino acid sequence (LCDR2) amino acid sequence set forth in SEQ ID NO:17; and
   a variable light chain CDR3 amino acid sequence (LCDR3) amino acid sequence set forth in SEQ ID NO:18.

2. The monoclonal antibody or antigen-binding fragment thereof of claim 1, wherein the monoclonal antibody, or antigen-binding fragment thereof is chimeric or humanized.

3. The monoclonal antibody or antigen-binding fragment thereof of claim 1, wherein the monoclonal antibody, or antigen-binding fragment thereof specifically binds human CD47.

4. The monoclonal antibody or antigen-binding fragment thereof of claim 3, wherein the monoclonal antibody, or antigen-binding fragment thereof specifically binds at least one of cynomolgus monkey, rat, or mouse CD47.

5. The monoclonal antibody or antigen-binding fragment thereof of claim 1, further comprising a heavy chain variable domain ($V_H$) and a light chain variable domain ($V_L$), selected from:
   (i) a heavy chain variable domain comprising the amino acid sequence of SEQ ID NO:36 and a light chain variable domain comprising the amino acid sequence SEQ ID NO:51;
   (ii) a heavy chain variable domain comprising the amino acid sequence of SEQ ID NO:36 and a light chain variable domain comprising the amino acid sequence SEQ ID NO:52;
   (iii) a heavy chain variable domain comprising the amino acid sequence of SEQ ID NO:37 and a light chain variable domain comprising the amino acid sequence SEQ ID NO:51;
   (iv) a heavy chain variable domain comprising the amino acid sequence SEQ ID NO:37 and a light chain variable domain comprising the amino acid sequence SEQ ID NO:52;
   (v) a heavy chain variable domain comprising the amino acid sequence of SEQ ID NO:38 and a light chain variable domain comprising the amino acid sequence SEQ ID NO:51; and
   (vi) a heavy chain variable domain comprising the amino acid sequence of SEQ ID NO:38 and a light chain variable domain comprising the amino acid sequence SEQ ID NO:52.

6. The monoclonal antibody or antigen-binding fragment thereof of claim 5, wherein the monoclonal antibody or antigen-binding fragment thereof further comprises an IgG isotype selected from IgG1, IgG1-N297Q, IgG2, IgG4, IgG4 S228P, and IgG4 PE.

7. The monoclonal antibody or antigen binding fragment thereof of claim 5, comprising one heavy chain and one light chain selected from:
   (i) a heavy chain comprising the amino acid sequence of SEQ ID NO:81 and a light chain comprising the amino acid sequence SEQ ID NO:73;
   (ii) a heavy chain comprising the amino acid sequence of SEQ ID NO:80 and a light chain comprising the amino acid sequence SEQ ID NO:70;
   (iii) a heavy chain comprising the amino acid sequence of SEQ ID NO:81 and a light chain comprising the amino acid sequence SEQ ID NO:70;
   (iv) a heavy chain comprising the amino acid sequence of SEQ ID NO:79 and a light chain comprising the amino acid sequence SEQ ID NO:70;
   (v) a heavy chain comprising the amino acid sequence of SEQ ID NO:79 and a light chain comprising the amino acid sequence SEQ ID NO:73;
   (vi) a heavy chain comprising the amino acid sequence of SEQ ID NO:80 and a light chain comprising the amino acid sequence SEQ ID NO:73.

8. The monoclonal antibody or antigen binding fragment thereof of claim 7 comprising a heavy chain comprising the amino acid sequence of SEQ ID NO:80 and a light chain comprising the amino acid sequence SEQ ID NO:70.

9. A pharmaceutical composition, comprising the monoclonal antibody, or antigen-binding fragment thereof, of claim 1, and a pharmaceutically or physiologically acceptable carrier, diluent, or excipient.

10. A pharmaceutical composition, comprising the monoclonal antibody, or antigen-binding fragment thereof, of claim 5, and a pharmaceutically or physiologically acceptable carrier, diluent, or excipient.

11. A pharmaceutical composition, comprising the monoclonal antibody, or antigen-binding fragment thereof, of claim 6, and a pharmaceutically or physiologically acceptable carrier, diluent, or excipient.

12. A pharmaceutical composition, comprising the monoclonal antibody, or antigen-binding fragment thereof, of claim 7, and a pharmaceutically or physiologically acceptable carrier, diluent, or excipient.

13. A pharmaceutical composition, comprising the monoclonal antibody, or antigen-binding fragment thereof, of claim 8, and a pharmaceutically or physiologically acceptable carrier, diluent, or excipient.

14. The pharmaceutical composition of claim 13, wherein the pharmaceutical composition is administered intravenously.

* * * * *